(12) United States Patent
Shimura et al.

(10) Patent No.: US 10,189,781 B2
(45) Date of Patent: Jan. 29, 2019

(54) ONIUM SALT AND COMPOSITION COMPRISING THE SAME

(71) Applicant: ASAHI KASEI E-MATERIALS CORPORATION, Tokyo (JP)

(72) Inventors: Tadashi Shimura, Tokyo (JP); Naoya Kamimura, Tokyo (JP); Akira Otani, Tokyo (JP); Hitoshi Shimada, Tokyo (JP)

(73) Assignee: ASAHI KASEI E-MATERIALS CORPORATION, Tokyo (JP)

( * ) Notice: Subject to any disclaimer, the term of this patent is extended or adjusted under 35 U.S.C. 154(b) by 150 days.

(21) Appl. No.: 15/024,712

(22) PCT Filed: Sep. 24, 2014

(86) PCT No.: PCT/JP2014/075331
§ 371 (c)(1),
(2) Date: Mar. 24, 2016

(87) PCT Pub. No.: WO2015/046277
PCT Pub. Date: Apr. 2, 2015

(65) Prior Publication Data
US 2016/0229801 A1    Aug. 11, 2016

(30) Foreign Application Priority Data

Sep. 25, 2013 (JP) ................... 2013-198802
Dec. 4, 2013 (JP) ................... 2013-251153
Jan. 31, 2014 (JP) ................... 2014-017774
Jan. 31, 2014 (JP) ................... 2014-017780

(51) Int. Cl.
| | |
|---|---|
| C08F 2/46 | (2006.01) |
| C08F 2/50 | (2006.01) |
| C08G 61/04 | (2006.01) |
| C07C 381/12 | (2006.01) |
| C08G 59/68 | (2006.01) |
| C07F 5/02 | (2006.01) |
| C07C 309/06 | (2006.01) |
| C08K 3/36 | (2006.01) |
| C09J 7/00 | (2018.01) |
| C09J 9/02 | (2006.01) |
| C09J 163/00 | (2006.01) |

(52) U.S. Cl.
CPC .......... *C07C 381/12* (2013.01); *C07C 309/06* (2013.01); *C07F 5/027* (2013.01); *C08G 59/68* (2013.01); *C08K 3/36* (2013.01); *C09J 7/00* (2013.01); *C09J 9/02* (2013.01); *C09J 163/00* (2013.01); *C09J 2203/326* (2013.01); *C09J 2463/00* (2013.01)

(58) Field of Classification Search
CPC ..... C07C 381/12; C07C 309/06; C07F 5/027; C08K 3/36; C09J 9/02; C09J 163/00; C09J 2203/326; C09J 7/00; C09J 2463/00

USPC ................. 522/31, 6, 71, 189, 184, 1; 520/1
See application file for complete search history.

(56) References Cited

U.S. PATENT DOCUMENTS

| | | | |
|---|---|---|---|
| 2005/0095532 A1* | 5/2005 | Kodama | ............... G03F 7/0045 430/270.1 |
| 2011/0120767 A1 | 5/2011 | Sato et al. | |
| 2011/0192639 A1 | 8/2011 | Shinya et al. | |
| 2014/0005301 A1 | 1/2014 | Kunimoto et al. | |
| 2015/0008022 A1 | 1/2015 | Masui et al. | |

FOREIGN PATENT DOCUMENTS

| | | |
|---|---|---|
| CN | 102762629 A | 10/2012 |
| CN | 103081236 A | 5/2013 |
| EP | 0 846 681 A1 | 6/1998 |
| GB | 1228094 A | 4/1971 |
| JP | 6-345726 A | 12/1994 |
| JP | 9-176112 A | 7/1997 |
| JP | 2013-045986 A | 3/2013 |
| JP | 2013-116892 A | 6/2013 |
| JP | 2013-198802 A | 10/2013 |
| JP | 5320523 B1 | 10/2013 |
| JP | 2015-063624 | 4/2015 |
| TW | 200910488 A | 3/2009 |
| WO | WO 2010/064648 A1 | 6/2010 |
| WO | WO 2011/138868 A1 | 11/2011 |
| WO | WO 2012/018123 A1 | 2/2012 |

(Continued)

OTHER PUBLICATIONS

STN Registry, "Sulfonium,dimethyl[1-phenyl-2-[(2,4,6-trimethylphenyl)thio]ethyl]-(OC-6-22) . . . ," Registration Nos. 79716-93-1, 79716-68-0, 79716-67-9, 79143-62-7, 79143-61-6, 79143-58-1, 79143-57-0, 66022-71-7, 66022-70-6, Entered STN: Nov. 16, 1984, 7 pages.

Feng Shaowei "New Ionic Liquids on Tertiary Sulfoniums and Perfluoroalkyltrifluroborates: Synthesis, Characterization and Properties", Thesis submitted in fulfillment of requirements of Master of Science Degree; Huazhong University of Science & Technology, 2010.

(Continued)

*Primary Examiner* — Jessica Whiteley
(74) *Attorney, Agent, or Firm* — Birch, Stewart, Kolasch & Birch, LLP

(57) ABSTRACT

The onium salt of the present invention contains predetermined compound A represented by the general formula (1). The composition of the present invention contains the onium salt of the present invention, and an onium salt containing predetermined compound B represented by the general formula (2). The onium salt and the composition of the present invention exert well-balanced excellent physical properties in terms of cold curing properties, storage stability, thermal shock resistance after curing, and moisture resistance.

7 Claims, 4 Drawing Sheets

(56) References Cited

FOREIGN PATENT DOCUMENTS

WO WO 2012/042796 A1 4/2012
WO WO 2012/113829 A1 8/2012

OTHER PUBLICATIONS

Kim et al., "Facile Nucleophilic Substitution of α-Alkoxysulfonium salts", Bull. Korean. Chem. Soc., vol. 14, No. 6 (1993) pp. 654-655.
Kim et al., "Photo and Thermal Polymerization of Epoxides and Vinyl Ethers by Novel Sulfonium Salts", Journal of Applied Polymer Science, vol. 108 (2008) pp. 858-862.
International Preliminary Report on Patentability issued in International Application No. PCT/JP2014/075331 dated Dec. 22, 2014, with English translation.
International Search Report, issued in PCT/JP2014/075331, dated Dec. 22, 2014.
Written Opinion of the International Searching Authority, issued in PCT/JP2014/075331, dated Dec. 22, 2014.

* cited by examiner

[Fig. 1]
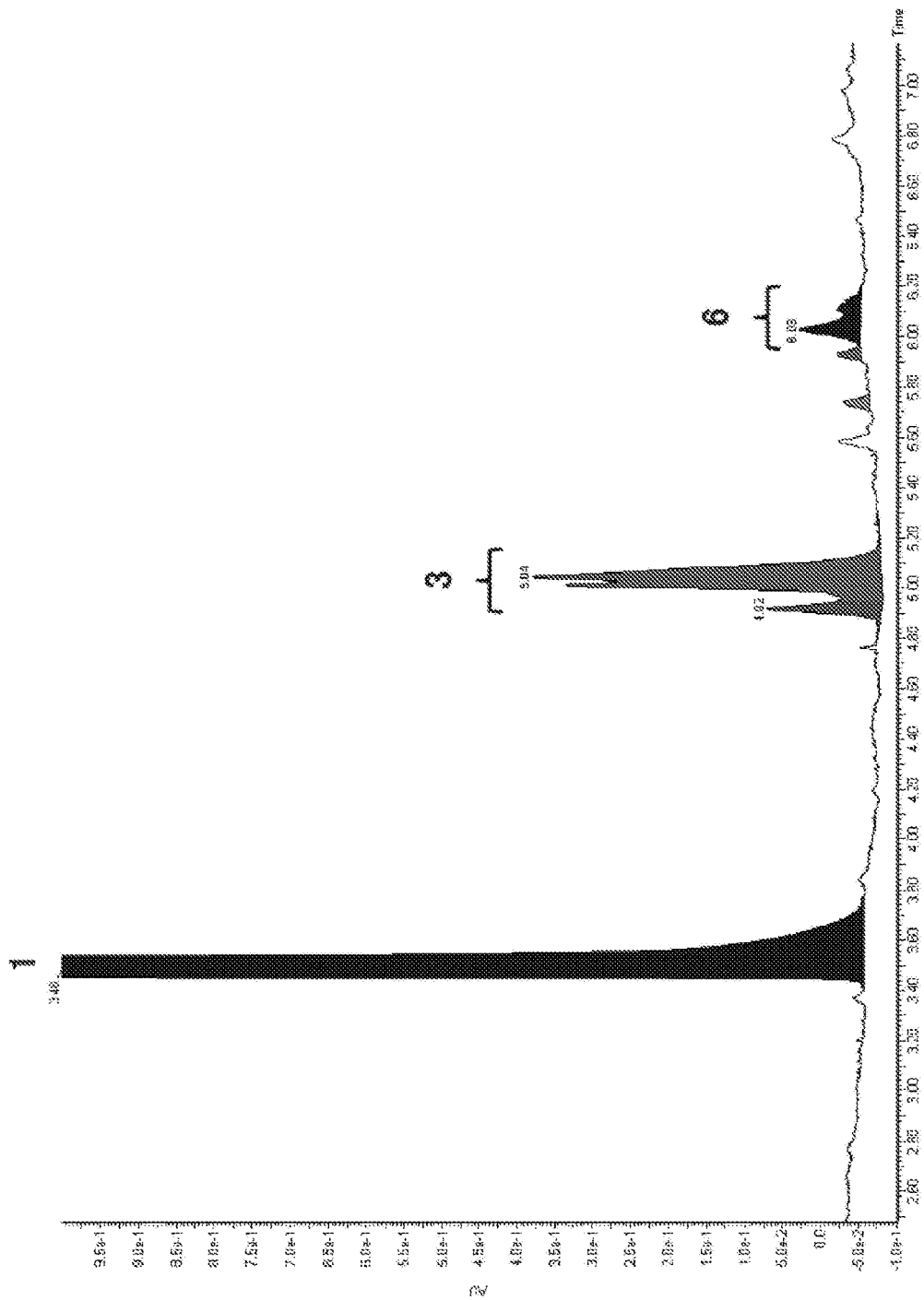

[Fig. 2]
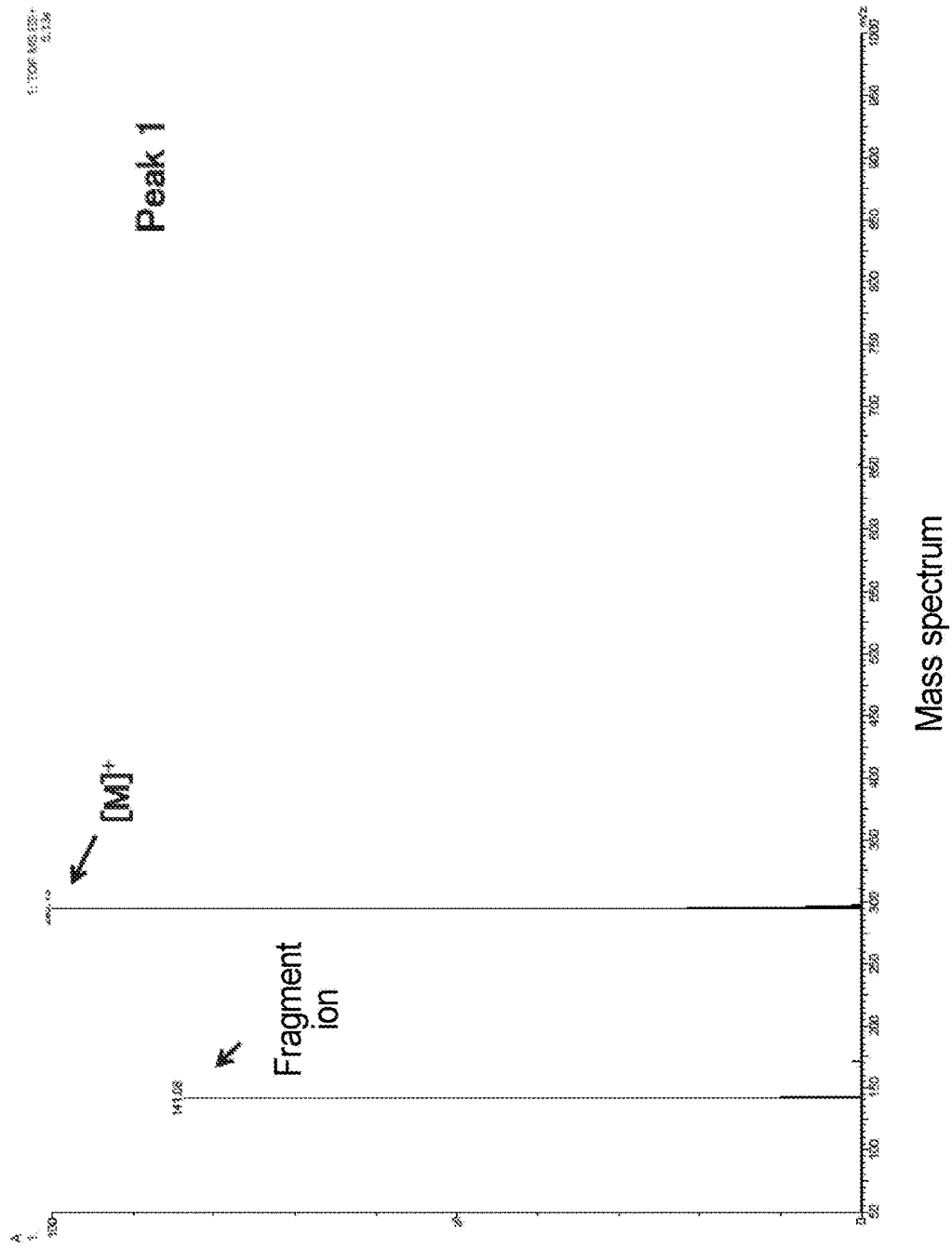

[Fig. 3]
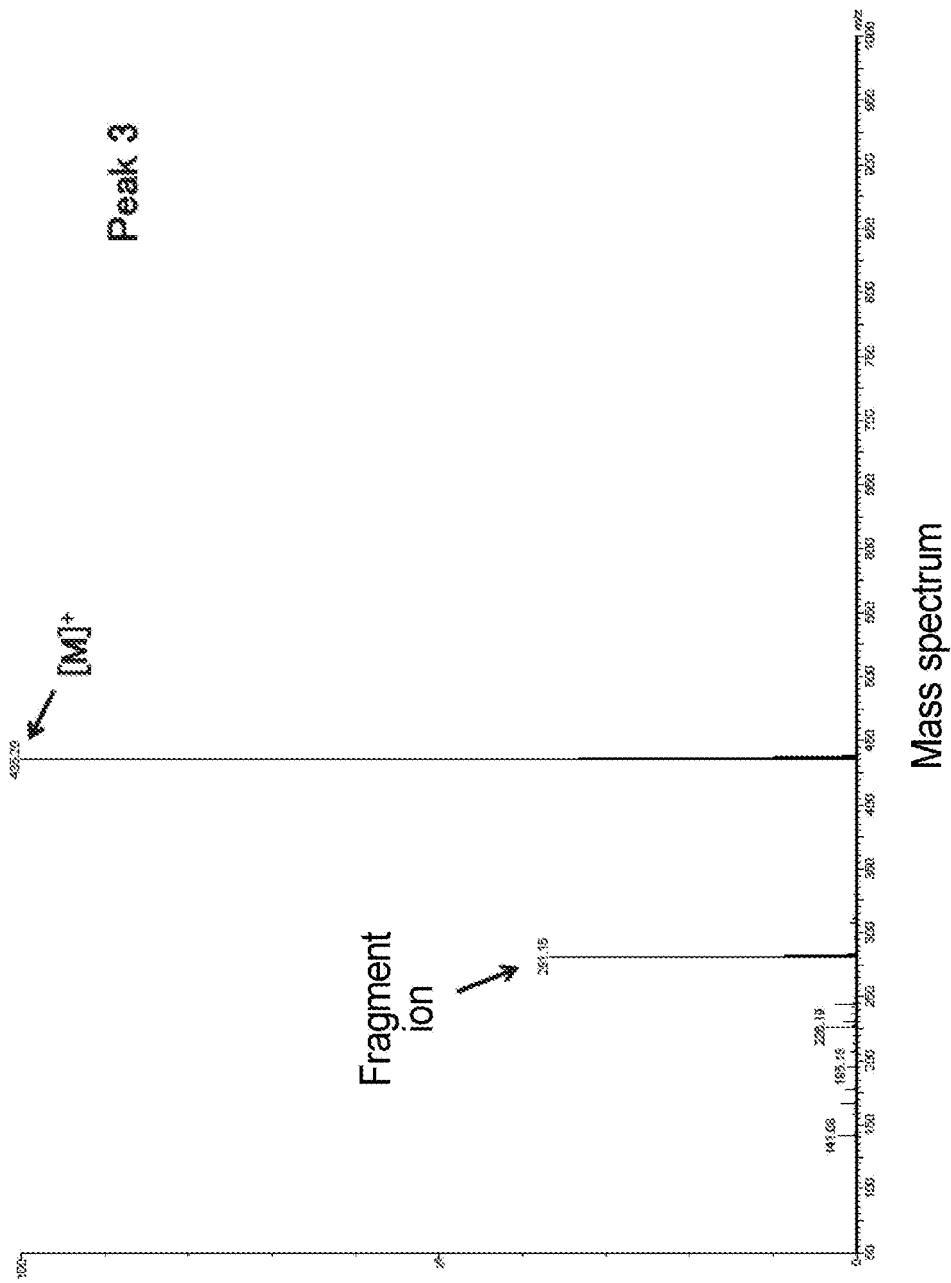

[Fig. 4]
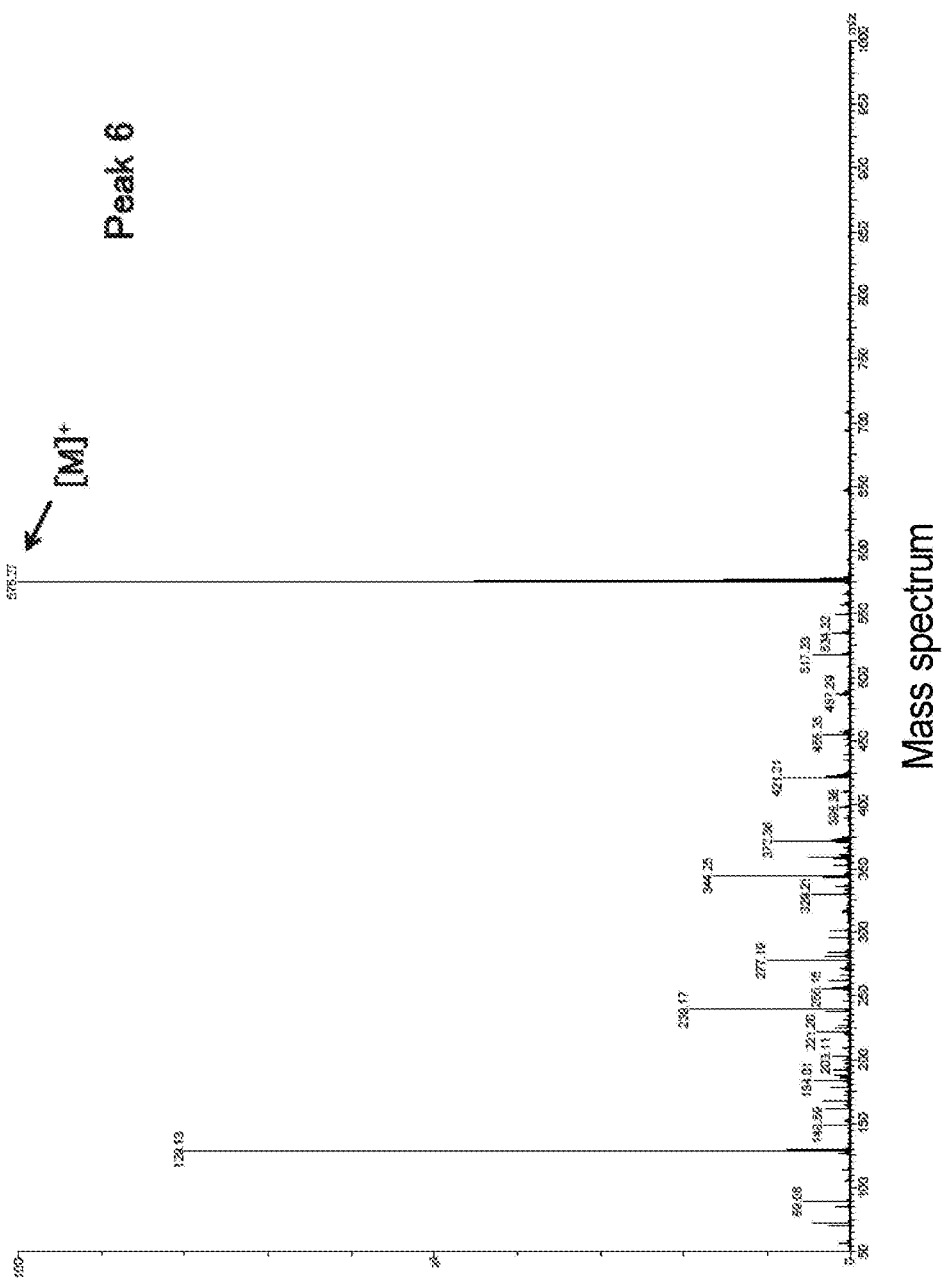

ONIUM SALT AND COMPOSITION COMPRISING THE SAME

TECHNICAL FIELD

The present invention relates to an onium salt and a composition comprising the same.

BACKGROUND ART

Heretofore, photo-cationically polymerizable epoxy resin compositions have been used as one type of adhesive for use in implementing electronic components such as IC chips onto wiring substrates. Such photo-cationically polymerizable epoxy resin compositions are supplemented with photo-cationic polymerization initiators that initiate cationic polymerization by generating protons through light. Sulfonium-antimonate complexes are known as such photo-cationic polymerization initiators.

The sulfonium-antimonate complexes have, as a counter anion, $SbF_6^-$ in which a fluorine atom is bonded to a metal antimony. Therefore, large amounts of fluorine ions are generated during cationic polymerization and induce migration between dissimilar metals, causing undesired corrosion in metal wiring or connection pads. Therefore, a proposition has been made to use, as cationic polymerization initiators, sulfonium-borate complexes having a tetrakis(pentafluorophenyl) borate anion $[(C_6F_5)_4B^-]$ in which a fluorine atom is bonded to a carbon atom, instead of $SbF_6^-$ (see e.g., Patent Document 1).

CITATION LIST

Patent Document

Patent Document 1: Japanese Patent Laid-Open No. 9-176112

SUMMARY OF INVENTION

Technical Problem

In many cases, junction areas cannot be irradiated with light when electronic components are implemented onto wiring substrates. If sulfonium-borate complexes can be diverted to thermal cationic polymerization initiators for thermally cationically polymerizable epoxy resin compositions, the cases mentioned above may not matter. However, the mere diversion of the technique described in Patent Document 1 to thermal cationic polymerization initiators cannot satisfy the following conditions at the same time: (a) to secure the migration resistance of epoxy resin compositions by reducing the generation of fluorine ions; (b) to improve productivity by minimizing the amount of a curing agent (polymerization initiator) used; (c) to improve the cold rapid curing properties and cold curing properties of epoxy resin compositions; and (d) to secure storage stability.

The present invention has been made in light of the problems of the conventional techniques mentioned above. An object of the present invention is to provide an onium salt that exerts well-balanced excellent physical properties in terms of cold curing properties, storage stability, thermal shock resistance after curing, and moisture resistance.

Solution to Problem

The present inventors have conducted diligent studies to solve the problems and consequently completed the present invention by finding out that the problems can be solved by using an onium salt having a predetermined structure.

Specifically, the present invention is as follows:

[1] An onium salt containing a compound A represented by the general formula (1):

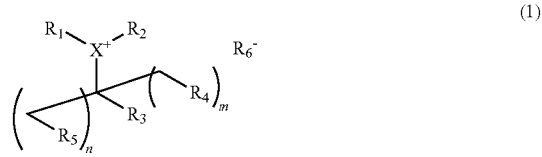

wherein $R_1$, $R_2$, $R_3$, $R_4$, and $R_5$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; X represents an atom that forms a monovalent cation; n represents an integer of 0 to 3; m represents an integer of 1 to 4; n and m satisfy n+m≤4; and $R_6$ represents an atomic group capable of forming a monovalent anion.

[2] The onium salt according to [1], wherein the $R_1$ has an aromatic ring.

[3] The onium salt according to [1] or [2], wherein the X is sulfur.

[4] The onium salt according to any one of [1] to [3], wherein the $R_2$ is an alkyl group.

[5] The onium salt according to any one of [1] to [4], wherein each of the $R_3$, the $R_4$, and the $R_5$ is an aralkyl group or an alkyl group having an unsaturated group at the β position.

[6] The onium salt according to any one of [1] to [5], wherein the $R_6$ is one group selected from the group consisting of $SbY_6^-$, $PY_6^-$, $AsY_6^-BY_4^-$, and $CY_3SO_3^-$ (wherein the Y represents at least one selected from the group consisting of a hydrogen atom, an alkyl group, F, Cl, Br, and I), or is represented by the following general formula (3):

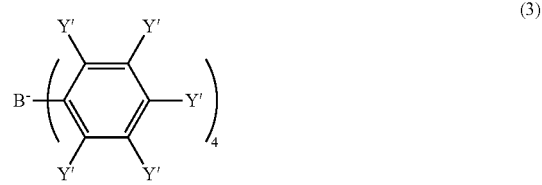

wherein each Y' represents a hydrogen atom, a halogen atom, or an alkyl group, and at least one of the Y' is a halogen atom.

[7] A composition containing
an onium salt according to any one of [1] to [6] in which the X is sulfur; and
an onium salt containing a compound B represented by the general formula (2):

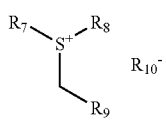

(2)

wherein $R_7$, $R_8$, and $R_9$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; X represents an atom that forms a monovalent cation; and $R_{10}$ represents an atomic group capable of forming a monovalent anion.

[8] The composition according to [7], wherein a ratio of the compound B to a total mass of the compound A and the compound B is 0.005 or more and 0.995 or less.

[9] The composition according to [7] or [8], further containing 5 ppm or higher and 10000 ppm or lower of a solvent having a boiling point of 0° C. to 200° C.

[10] The composition according to any one of [7] to [9], further containing 5 ppm to 5000 ppm of a silver compound.

[11] The composition according to any one of [7] to [10], further containing 5 ppm to 5000 ppm of a compound D represented by the following general formula (4):

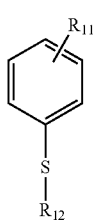

(4)

wherein $R_{11}$ and $R_{12}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other.

[12] The composition according to any one of [7] to [11], further containing 5 ppm to 5000 ppm of a compound C represented by the following general formula (5):

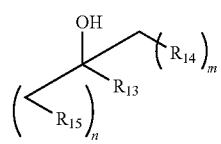

(5)

wherein $R_{13}$, $R_{14}$, and $R_{15}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; n represents an integer of 0 to 3; m represents an integer of 1 to 4; and n and m satisfy n+m≤4.

[13] A cation-generating agent containing the onium salt according to any one of [1] to [6] or containing the composition according to any one of [7] to [12].

[14] A cationically polymerizable composition containing a cationically polymerizable compound, a filler, and the onium salt according to any one of [1] to [6].

[15] An underfill containing the cationically polymerizable composition according to [14].

[16] A method for producing an underfill, containing using a cationically polymerizable composition according to [14].

[17] A connecting structure obtained by the method for producing the underfill according to [16].

[18] A thermally cationically polymerizable composition containing a binder component and the onium salt according to any one of [1] to [6].

[19] An anisotropically conductive adhesive film containing the thermally cationically polymerizable composition according to [18] and conductive particles.

[20] A method for producing a connecting structure having a configuration in which a terminal of a first electronic component is anisotropically conductively connected to a terminal of a second electronic component, the method including the steps of:

(A) temporarily affixing the anisotropically conductive adhesive film according to [19] onto the terminal of the first electronic component;

(B) temporarily disposing the second electronic component onto the anisotropically conductive adhesive film such that the terminal of the second electronic component is opposed to the corresponding terminal of the first electronic component; and (C) anisotropically conductively connecting the terminal of the first electronic component to the terminal of the second electronic component by heating using a heating unit with pressure applied to the second electronic component using a pressing unit.

[21] A connecting structure obtained by the method for producing the connecting structure according to [20].

[22] A film-shaped connecting material containing a cationically polymerizable compound, a binder component, and two or more types of compounds B each represented by the following general formula (2):

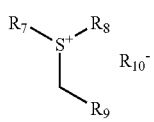
(2)

wherein $R_7$, $R_8$, and $R_9$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; X represents an atom that forms a monovalent cation; and $R_{10}$ represents an atomic group capable of forming a monovalent anion.

[23] The film-shaped connecting material according to [22], further containing a cation scavenger reacting with cation species generated by the compounds B, wherein a content of the cation scavenger is 0.1 to 20 parts by mass with respect to 100 parts by mass of the compounds B.

[24] A method for producing a connecting structure, including the step of interposing the film-shaped connecting material according to [22] or [23] between a pair of opposed circuit boards, followed by heating and application of pressure.

[25] A connecting structure obtained by connecting a pair of opposed circuit boards via the film-shaped connecting material according to [22] or [23].

Advantageous Effects of Invention

The present invention can provide an onium salt that exerts well-balanced excellent physical properties in terms of cold curing properties, storage stability, thermal shock resistance after curing, and moisture resistance.

BRIEF DESCRIPTION OF DRAWINGS

FIG. 1 shows results of subjecting a sample obtained in Example 1 to LC.

FIG. 2 shows a mass spectrum corresponding to peak 1 shown in FIG. 1.

FIG. 3 shows a mass spectrum corresponding to peak 3 shown in FIG. 1.

FIG. 4 shows a mass spectrum corresponding to peak 6 shown in FIG. 1.

DESCRIPTION OF EMBODIMENTS

Hereinafter, an embodiment for carrying out the present invention (hereinafter, also referred to as the "present embodiment") will be described in detail. The present invention is not intended to be limited by the present embodiment, and various changes or modifications can be made therein without departing from the spirit of the present invention.

[Onium Salt]

The onium salt of the present embodiment contains compound A represented by the general formula (1) given below. The onium salt of the present embodiment can exert well-balanced excellent physical properties in terms of cold curing properties, storage stability, thermal shock resistance after curing, and moisture resistance.

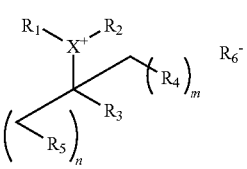
(1)

In the general formula (1), $R_1$, $R_2$, $R_3$, $R_4$, and $R_5$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other. X represents an atom that forms a monovalent cation. n represents an integer of 0 to 3. m represents an integer of 1 to 4. n and m satisfy n+m≤4. $R_6$ represents an atomic group capable of forming a monovalent anion.

$R_1$ preferably has an aromatic ring from the viewpoint of a conjugate system. Specific examples of the aromatic ring include, but are not limited to, benzene, naphthalene, anthracene, chrysene, pyrene, coronene, and kekulene, which may each be substituted. Among them, benzene or naphthalene is more preferably substituted by a group selected from the group consisting of hydrogen, a carboxyl group, an amino group, a hydroxy group, a methoxy group, fluorine, chlorine, bromine, iodine, boronic acid, phosphoric acid, methoxycarbonyl, a hydroxymethyl group, a dimethyl phosphate group, an isobutyro group, an isothiocyanate group, a thiourea group, a nitro group, a trifluoro group, an acetyl group, a carbonyl hydrazide group, a methylamino group, a tetramethyldioxoborane group, and a propionic acid group.

Examples of the X (atom that forms a monovalent cation) include, but are not limited to, sulfur, nitrogen, and phosphorus. X in the general formula (1) is preferably a sulfur atom from the viewpoint of production.

In the present embodiment, the $R_2$ is preferably an alkyl group from the viewpoint of further improving the yield of reaction for forming sulfonium. Examples of the alkyl group include, but are not limited to, a linear alkyl group having 1 to 18 carbon atoms (methyl, ethyl, n-propyl, n-butyl, n-pentyl, n-octyl, n-decyl, n-dodecyl, n-tetradecyl, n-hexadecyl, n-octadecyl, etc.), a branched alkyl group having 1 to 18 carbon atoms (isopropyl, isobutyl, sec-butyl, tert-butyl, isopentyl, neopentyl, tert-pentyl, isohexyl, and isooctadecyl), and a cycloalkyl group having 3 to 18 carbon atoms (cyclopropyl, cyclobutyl, cyclopentyl, cyclohexyl, 4-decylcyclohexyl, etc.). Among those described above, a methyl group, an ethyl group, a n-propyl, or an isopropyl group is more preferred from the viewpoint of steric hindrance.

Each of $R_3$, $R_4$, and $R_5$ according to the present embodiment is preferably an aralkyl group or an alkyl group having an unsaturated group at the β position from the viewpoint of the conjugation of a generated cation. Examples of the aralkyl group include, but are not limited to, a lower alkyl group substituted by an aryl group having 6 to 10 carbon atoms (benzyl, 2-methylbenzyl, 1-naphthylmethyl, 2-naphthylmethyl, etc.). Specific examples of $R_3$, $R_4$, and $R_5$ include, but are not limited to, a triphenylmethyl group, a diphenylmethyl group, a (1,2-diphenylethane)methyl group, a o-/m-/p-nitrobenzyl group, a methoxybenzyl group, a methylbenzyl group, an (ethyl benzoate)methyl group, a (methyl benzoate)ethyl group, a (methyl benzoate)methyl group, an (ethyl benzoate)ethyl group, a (trifluoromethyl)benzyl group, a cyanobenzyl group, a dimethylbenzyl group, a trimethylbenzyl group, a tetramethylbenzyl group, a bis(trifluoromethyl)benzyl group, a 4-methoxy-3-methylbenzyl group, a trimethoxybenzyl group, a dimethoxybenzyl group, a methylsulfonylbenzyl group, a 4-methyl-naphthyl group, an α-naphthylmethyl group, a β-naphthylmethyl group, a methylstyryl group, an anthracenemethyl group, a fluorenemethyl group, a 4-methoxytrityl group, a methylbiphenyl group, and a benzyl group. Among them, an α-naphthylmethyl group, a 2-methylbenzyl group, a propargyl group, or a butene group is more preferred from the viewpoint of steric hindrance.

In the present embodiment, each of the $R_6^-$ and $R_{10}^-$ mentioned later is preferably one group selected from the group consisting of $SbY_6^-$, $PY_6^-$, $AsY_6^-$, $BY_4^-$, and $CY_3SO_3^-$ (wherein the Y is at least one group selected from the group consisting of F, Cl, Br, and I), or is represented by the following general formula (3) from the viewpoint of acidity:

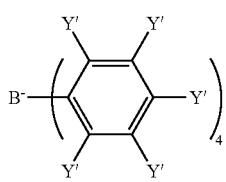
(3)

wherein Y' represents a hydrogen atom, a halogen atom, or an alkyl group.

More specifically, preferred examples of $R_6^-$ and $R_{10}^-$ can include $SbF_6^-$, $PF_6^-$, $AsF_6^-$, $BF_4^-$, $SbCl_6^-$, $ClO_4^-$, $CF_3SO_3^-$, $CH_3SO_3^-$, $FSO_3^-$, $F_2PO_2^-$, p-toluenesulfonate, camphorsulfonate, tetraphenyl borate, tetrakis(pentafluorophenyl) borate, tetrakis(4-fluorophenyl) borate, and tris(pentafluoroethyl)trifluoro group. The cation moiety of the borate compound (borate-containing compound that forms a monovalent anion) is preferably a lithium cation or a sodium cation, more preferably a sodium cation.

The onium salt of the present embodiment is preferably used with an onium salt containing compound B represented by the general formula (2) from the viewpoint of the balance between the curing properties and stability of the resulting composition:

wherein $R_7$, $R_8$, and $R_9$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; X represents an atom that forms a monovalent cation; and $R_{10}$ represents an atomic group capable of forming a monovalent anion.

$R_7$ in the general formula (2) can adopt the same embodiment as that described about $R_1$ in the compound A. $R_8$ in the general formula (2) can adopt the same embodiment as that described about $R_2$ in the compound A. $R_9$ in the general formula (2) can adopt the same embodiment as that described about $R_3$ in the compound A. $R_{10}$ in the general formula (2) can adopt the same embodiment as that described about $R_6$ in the compound A. The compound B mentioned above can exert well-balanced excellent physical properties in terms of cold curing properties, storage stability, thermal shock resistance after curing, and moisture resistance, as well as the onium salt (compound A) of the present embodiment.

More specific examples of the general formula (1) wherein n=1 and m=1 can include, but are not limited to, the following general formulas (6-1) to (6-9):

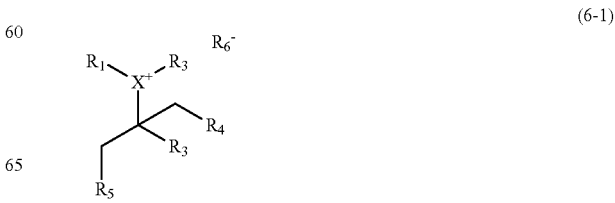

(6-2)
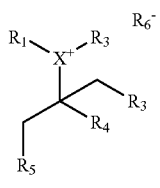

(6-3)
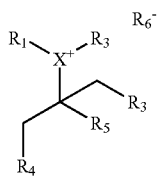

(6-4)
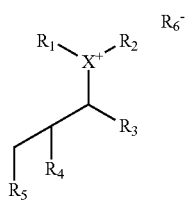

(6-5)
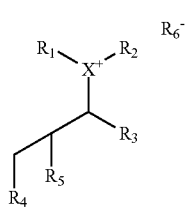

(6-6)
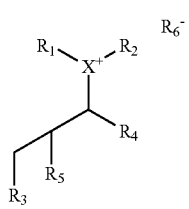

(6-7)
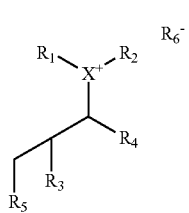

(6-8)
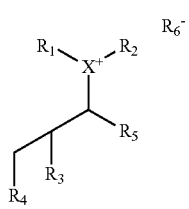

(6-9)
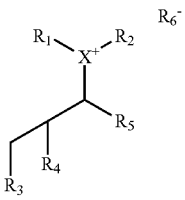

[Method for Producing Onium Salt]

The method for producing the onium salt of the present embodiment is not particularly limited. For example, the onium salt of the present embodiment represented by the general formula (1) wherein n=0 and m=1 can be produced according to reaction schemes 1 to 3 shown below. In the reaction schemes 1 to 3, $R_1$ to $R_4$, m, and n are as defined above. $R_7$, $R_8$, and $R_9$ in the compound B represented by the general formula (2) correspond to $R_1$, $R_2$, and $R_3$, respectively and are indicated by $R_1$, $R_2$, and $R_3$ in the reaction schemes 1 to 3. $R_{16}$ represents an atomic group capable of forming a monovalent anion. Z represents halogen. $R_{17}$ represents an alkali metal ion ($Li^+$, $Na^+$, or $K^+$).

[Reaction scheme 1]

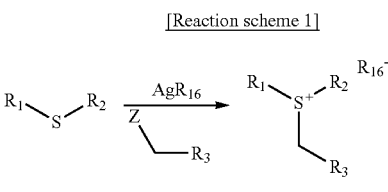

+ AgZ

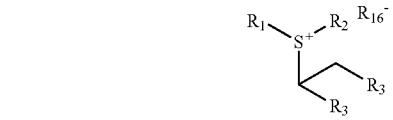

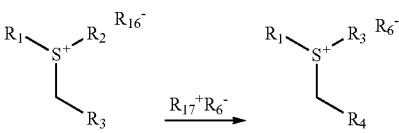

[Reaction scheme 2]

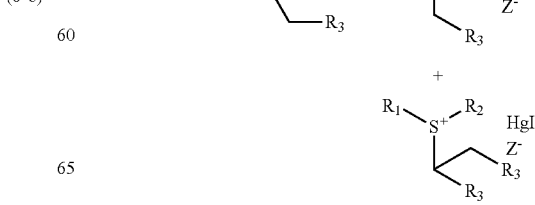

+

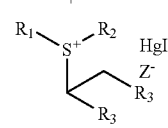

-continued

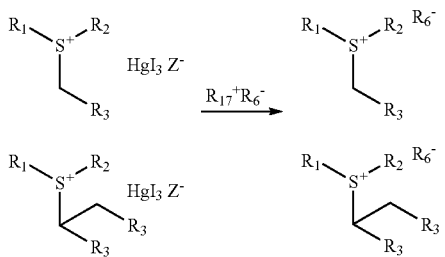

[Reaction scheme 3]

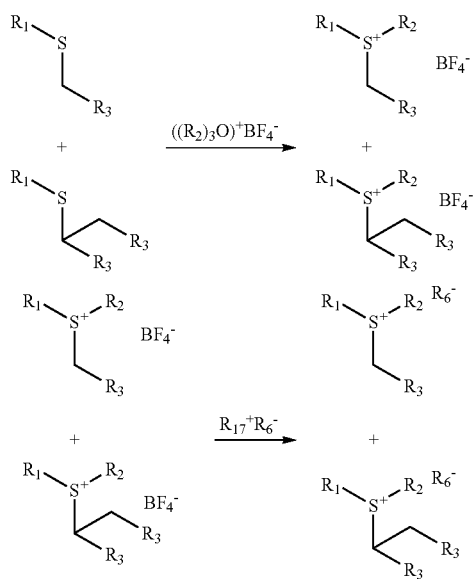

In the reaction scheme 1, AgZ is preferably an Ag compound having an anion with a large ion radius. In the embodiment shown in the reaction scheme 1, a silver compound and a sulfur compound are dissolved or dispersed in a solvent, and this solution is mixed with a compound having a methylene group. Subsequently, AgZ is removed from the obtained mixture, and the resulting product is mixed with $R_{17}{}^+R_6{}^-$. The obtained mixture is desalted, and the organic solvent layer is separated. Then, the organic solvent can be distilled off to obtain the compounds A and B.

In the embodiment shown in the reaction scheme 2, a mercury compound and a sulfur compound are dissolved or dispersed in a solvent, and this solution is mixed with a compound having a methylene group. The obtained mixture is mixed with $R_{17}{}^+R_6{}^-$. The obtained mixture is desalted, and the organic solvent layer is separated. Then, the organic solvent can be distilled off to obtain the compounds A and B.

In the embodiment shown in the reaction scheme 3, sulfide shown in this scheme is dissolved or dispersed in an organic solvent such as dichloromethane, and this solution is mixed with an equimolar amount of an alkylating agent (Meerwein reagent). The obtained two-layer mixture is stirred at a temperature of 20 to 80° C. for 1 to 3 hours. After subsequent reaction with a salt of sulfonium halide, fluorinated alkyl phosphoric acid anion, and an alkali metal cation, the organic solvent layer is separated. Then, the organic solvent can be distilled off to obtain the compounds A and B.

The reactions of the reaction schemes 1 to 3 may be carried out, if necessary, in an organic solvent (hexane, ethyl acetate, methyl ethyl ketone, diethyl ether, acetonitrile, tetrahydrofuran, dioxane, ethanol, acetone, etc.). The reaction temperature can be set to approximately 0 to approximately 120° C. The reaction time can be set to approximately 1 to several tens of hours.

The reaction at the second stage may be carried out subsequently to the reaction at the first stage, or may be carried out after isolation (and, if necessary, purification) of the reaction intermediate. The reaction intermediate is double-decomposed by mixing and stirring, and the deposited solid is filtered off, or the separated oil is subjected to extraction with an organic solvent, followed by the removal of the organic solvent to obtain the onium salt of the present embodiment in a solid or a viscous liquid form. The obtained solid or viscous liquid may be washed with an appropriate organic solvent or purified by recrystallization or column chromatography, according to the need.

[Composition]

The composition of the present embodiment contains the onium salt containing the compound A and the onium salt containing the compound B, wherein X in the compound A is sulfur. The composition of the present embodiment thus constituted secures the migration resistance of the epoxy resin composition, has excellent cold curing properties and storage stability, and exerts curing properties even when used in a small amount.

In the composition of the present embodiment, the lower limit of the ratio of the mass of the compound B to the total mass of the compound A and the compound B is preferably 0.005 or more, more preferably 0.010 or more, further preferably 0.020 or more, still further preferably 0.5 or more, even further preferably 0.6 or more, particularly preferably 0.7 or more. The upper limit of this mass ratio is preferably 0.995 or less, more preferably 0.99 or less, further preferably 0.985 or less. When the mass ratio is 0.995 or less, it tends to be able to effectively prevent the disadvantage that curing properties are reduced due to the reduced diffusibility of sulfonium salts which facilitates remaining of the sulfonium salts in a composition containing a polymerizable compound. When the mass ratio is 0.005 or more, better storage stability can be secured. On the other hand, if the mass ratio exceeds 0.995, reduced diffusibility of sulfonium salts facilitates remaining of unreacted sulfonium salts in a composition containing a polymerizable compound, reducing curing properties. If the mass ratio is less than 0.005, storage stability is reduced. Although this mechanism is not clear, it can be assumed that structures containing a plurality of $R_3$, $R_4$, and $R_5$ in one molecule are increased with increase in the ratio of the compound B, whereby the steric hindrance of the moiety containing $R_3$, $R_4$, and $R_5$ tends to be large for sulfonium groups. The structures containing a plurality of $R_3$, $R_4$, and $R_5$ have large resonance structures and therefore generate stable cations. This probably tends to easily generate cations at a temperature lower than the desired temperature.

The ratio of the mass of the compound A or B to the total mass of the compound A and the compound B according to the present embodiment can be determined on the basis of each peak identified by LC-MS analysis. More specifically, area ratios in LC can be determined according to JIS K0124. More specifically, in the case of taking $R_3$=a naphthyl group as an example, the respective peaks of the compound A and the compound B can be identified from peaks differing in detected ion m/z by 140 in the MS spectra.

(LC measurement)

Ratio X of the mass of the compound A to the total mass of the compound A and the compound B can be determined according to the expression give below from the area ratio (%) of peaks observed in HPLC. The LC peaks of the compound A and the compound B can be obtained by measuring their respective mass spectra. The area of each peak can be approximated by an area surrounded by each peak and a straight baseline drawn with respect to the peak. Specifically, X can be determined according to the following expression:

$$X = \text{(Ratio \% of the area of the compound } A\text{)}/\text{(Ratio \% of the area of the compound } A + \text{Ratio \% of the area of the compound } B\text{)}$$

The LC measurement can be conducted using high-performance liquid chromatography UPLC H Class manufactured by Waters Corp. [column: CSH C18 manufactured by Waters Corp. (column size: 2.1 mm I.D.×50 mm), eluent: acetonitrile/0.1% by mass of aqueous formic acid solution=0/100→100/0 in 20 minutes, gradient analysis, flow rate: 0.2 mL/min, detector: PDA (UV 280 nm), temperature: 40° C., sample concentration: 0.5% by mass, injection volume: 1 μL, peak area analysis software: Empower manufactured by Waters Corp.].

The chemical structures of the compound A and the compound B of the present embodiment can each be identified by a general analysis approach (e.g., $^1$H-nuclear magnetic resonance spectra, infrared absorption spectra, and/or element analysis).

The composition of the present embodiment preferably contains a particular impurity at a particular ratio. The composition of the present embodiment preferably contains, for example, 5 ppm or higher and 10000 ppm or lower of a solvent having a boiling point of 0° C. to 200° C. Specific examples of the solvent as the impurity include, but are not limited to, diethyl ether, pentane, dichloromethane, carbon disulfide, acetone, 1,1-dichloroethane, dichloromethane, chloroform, methanol, tetrahydrofuran, hexane, trifluoroacetic acid, 1,1,1-trichloroethane, carbon tetrachloride, ethyl acetate, ethanol, methyl ethyl ketone, benzene, cyclohexane, acetonitrile, 2-propanol, 1,2-dichloroethane, 1,2-dimethoxyethane, trichloroethylene, propionitrile, heptane, water, nitromethane, dioxane, toluene, nitroethane, pyridine, methyl isobutyl ketone, ethylenediamine, 1-butanol, acetic acid, 2-methoxyethanol, octane, butyl acetate, morpholine, chlorobenzene, 2-ethoxyethanol, p-xylene, m-xylene, acetic anhydride, and o-xylene. Diethyl ether, dichloromethane, acetone, toluene, or methyl ethyl ketone is preferred from the viewpoint of the solubility of the compound A and the compound B in the solvent. When the content of the solvent is 5 ppm or higher, the compound A and the compound B tend to be able to make a sufficient contribution to curing properties. When the content of the solvent is 10000 ppm or lower, the composition containing the compound A and the compound B tends to be able to reduce voids that may be caused in cured products. Although this mechanism is not clear, it can be assumed that the composition of the present embodiment containing the solvent as described above, in addition to the compound A and the compound B, has improved diffusibility of each compound in the composition and favorable curing properties.

Also, the composition of the present embodiment preferably contains 5 ppm or higher and 10000 ppm or lower of a silver compound. Specific examples of the silver compound include, but are not limited to: silver halides such as silver bromide, silver chloride, silver iodide, and silver fluoride; and silver borofluoride, silver oxide, silver sulfide, silver nitride, silver hydroxide, silver cyanide, silver nitrate, silver carbonate, silver hexafluorophosphate, and silver tetrafluoroborate. When the content of the silver compound is 5 ppm or more, stability tends to be sufficiently improved. When the content of the silver compound is 10000 ppm or lower, adequate curing properties tend to be able to be secured. Although this mechanism is not clear, it can be assumed that the silver compound contained at the content described above can form a complex with a generated cation, thereby improving latency.

Also, the composition of the present embodiment preferably contains 5 ppm to 5000 ppm of compound D represented by the following general formula (4):

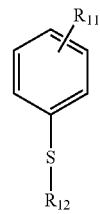

(4)

wherein $R_{11}$ and $R_{12}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other.

Specific examples of the alkyl group represented by $R_{12}$ include, but are not limited to, a linear alkyl group having 1 to 18 carbon atoms (methyl, ethyl, n-propyl, n-butyl, n-pentyl, n-octyl, n-decyl, n-dodecyl, n-tetradecyl, n-hexadecyl, and n-octadecyl, etc.), a branched alkyl group having 1 to 18 carbon atoms (isopropyl, isobutyl, sec-butyl, tert-butyl, isopentyl, neopentyl, tert-pentyl, isohexyl, and isooctadecyl), and a cycloalkyl group having 3 to 18 carbon atoms (cyclopropyl, cyclobutyl, cyclopentyl, cyclohexyl, and 4-decylcyclohexyl, etc.). Among those described above, a methyl group, an ethyl group, a n-propyl, or an isopropyl group is more preferred from the viewpoint of steric hindrance.

$R_{11}$ is specifically, preferably, hydrogen, a hydroxy group, a methoxy group, a carbonyl group, a methoxy carbonate group, a carboxy group, fluorine, chlorine, or bromine.

When the content of the compound D is 5 ppm or higher, the compound D tends to produce an adequate effect of storage stability. When the content of the compound D is 5000 ppm or lower, adequate curing properties tend to be able to be secured. Although this mechanism is not clear, it can be assumed that a carbo cation generated from the compound A or B is temporarily trapped by the nucleophilicity of the sulfur atom, thereby suppressing polymerization reaction and improving the storage stability of the composition.

Also, the composition of the present embodiment preferably contains 5 ppm to 5000 ppm of compound C represented by the following general formula (5):

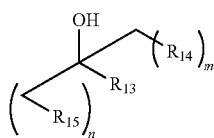

(5)

wherein $R_{13}$, $R_{14}$, and $R_{15}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; n represents an integer of 0 to 3; m represents an integer of 1 to 4; and n and m satisfy n+m≤4.

Each of $R_{13}$, $R_{14}$, and $R_{15}$ is specifically, preferably, an aralkyl group or an alkyl group having an unsaturated group at the β position from the viewpoint of the conjugation of a generated cation. Examples of the aralkyl group include a lower alkyl group substituted by an aryl group having 6 to 10 carbon atoms (benzyl, 2-methylbenzyl, 1-naphthylmethyl, 2-naphthylmethyl, etc.). Specific examples of $R_{14}$ include, but are not limited to, a triphenylmethyl group, a diphenylmethyl group, a (1,2-diphenylethane)methyl group, a o-/m-/p-nitrobenzyl group, a methoxybenzyl group, a methylbenzyl group, an (ethyl benzoate)methyl group, a (methyl benzoate)ethyl group, a (methyl benzoate)methyl group, an (ethyl benzoate)ethyl group, a (trifluoromethyl)benzyl group, a cyanobenzyl group, a dimethylbenzyl group, a trimethylbenzyl group, a tetramethylbenzyl group, a bis(trifluoromethyl)benzyl group, a 4-methoxy-3-methylbenzyl group, a trimethoxybenzyl group, a dimethoxybenzyl group, a methylsulfonylbenzyl group, a 4-methyl-naphthyl group, an α-naphthylmethyl group, a β-naphthylmethyl group, a methylstyryl group, an anthracenemethyl group, a fluorenemethyl group, a 4-methoxytrityl group, a methylbiphenyl group, and a benzyl group. Among them, an α-naphthylmethyl group, a 2-methylbenzyl group, a propargyl group, or a butene group is more preferred from the viewpoint of steric hindrance.

When the content of the compound C is 5 ppm or higher, curing properties tend to be improved. When the content of the compound C is 5000 ppm or lower, adequate storage stability tends to be able to be secured. Although this mechanism is not clear, it can be assumed that a carbo cation generated from the compound A or B attracts the proton of a hydroxy group in the compound C, thereby promoting polymerization reaction.

The aforementioned impurity according to the present embodiment can be qualitatively and quantitatively determined by appropriately using GC, GC-MS, LC, LC-MS, ion chromatography, or $^1$H-NMR. More specifically, the qualitative and quantitative determination can be conducted by a method described in Examples mentioned later.

The aforementioned impurity according to the present embodiment may be contained not only in the composition of the present embodiment but in a cation-generating agent, a cationically polymerizable composition, an underfill, a thermally cationically polymerizable composition, an anisotropically conductive adhesive film, a film-shaped connecting material, and a connecting structure obtained therefrom according to the present embodiment as mentioned later. In this case, the solvent is preferably contained at 5 ppm or higher and 10000 ppm or lower; the silver compound is preferably contained at 5 ppm or higher and 5000 ppm or lower; the compound D is preferably contained at 5 ppm or higher and 5000 ppm or lower; and the compound C is preferably contained at 5 ppm or higher and 5000 ppm or lower, from the viewpoints mentioned above.

The compound A (onium salt) and the compound B (onium salt) according to the present embodiment and the composition of the present embodiment containing these compounds are suitable as cation (acid)-generating agents. In the present specification, the "cation-generating agent (acid-generating agent)" refers to an agent that generates a cation (acid) through the decomposition of its chemical structure by heating and/or energy beam irradiation. The generated acid can be used as a catalyst for the curing reaction or the like of a polymerizable compound. The energy beam can be any beam as long as the beam has energy that induces the decomposition of the cation-generating agent of the present embodiment. The energy beam is preferably energy beam in ultraviolet to visible light regions (wavelength: approximately 100 to approximately 800 nm) obtained from, for example, a low-pressure, medium-pressure, high-pressure, or ultrahigh-pressure mercury lamp, a metal halide lamp, a LED lamp, a xenon lamp, a carbon arc lamp, a fluorescent lamp, semiconductor solid laser, argon laser, He—Cd laser, KrF excimer laser, ArF excimer laser, or F2 laser. In addition to those described above, radiation having high energy, such as electron beam or X rays may be used as the energy beam.

The cation-generating agent according to the present embodiment may employ the compound A or B according to the present embodiment as it is or may further contain an additional acid-generating agent. When the cation-generating agent contains an additional acid-generating agent, the content (part by mass) of the additional acid-generating agent is preferably 1 to 100 parts by mass, more preferably 5 to 50 parts by mass, with respect to the total number of moles of the onium salt according to the present embodiment. The additional acid-generating agent includes those conventionally known in the art, such as onium salts (sulfonium, iodonium, selenium, ammonium, phosphonium, etc.) and salts of transition metal complex ions and anions.

Thus, the cation-generating agent according to the present embodiment has functions as an acid-generating agent. The acid-generating agent may be dissolved in a solvent and/or a cationically polymerizable compound in advance in order to facilitate its dissolution in a cationically polymerizable compound mentioned later.

Examples of the solvent include, but are not limited to: carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and 2-heptanone; polyhydric alcohols and derivatives thereof such as monomethyl ether, monoethyl ether, monopropyl ether, monobutyl ether, or monophenyl ether of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

In the case of using a solvent, the ratio of the solvent used is preferably 15 to 1000 parts by mass, more preferably 30 to 500 parts by mass, with respect to 100 parts by mass of the cation-generating agent (acid-generating agent) according to the present embodiment. These solvents may be used alone, or two or more thereof may be used in combination.

[Cationically Polymerizable Composition]

The cationically polymerizable composition of the present embodiment contains a cationically polymerizable compound, a filler, and the onium salt of the present embodiment. The cationically polymerizable composition of the present embodiment thus constituted is excellent in cold curing properties and storage stability, and the balance between thermal shock resistance exerted after curing and moisture resistance.

The content of the onium salt of the present embodiment in the cationically polymerizable composition can be appropriately set according to the purpose and is preferably 5 to 30 parts by mass, more preferably 5 to 20 parts by mass, with respect to 100 parts by mass of the cationically polymerizable composition from the viewpoint of securing an adequate curing rate and securing adequate curing properties.

(Cationically Polymerizable Compound)

The cationically polymerizable composition of the present embodiment also contains a cationically polymerizable compound, in addition to the onium salt according to the present embodiment mentioned above. One type of or a mixture of two or more type of the cationically polymerizable compounds according to the present embodiment are used.

Typical examples of the cationically polymerizable compound include, but are not limited to, epoxy compounds and oxetane compounds. These compounds are preferred because of easy availability and convenient handling.

The epoxy compounds are not particularly limited, and alicyclic epoxy resins, aromatic epoxy resins, aliphatic epoxy resins, and the like are suitable.

Specific examples of the alicyclic epoxy resins include, but are not limited to, polyglycidyl ether of a polyhydric alcohol having at least one alicyclic ring, and cyclohexene oxide- and cyclopentene oxide-containing compounds obtained by the epoxidation of cyclohexene ring- or cyclopentene ring-containing compound using an oxidizing agent. More specific examples thereof include hydrogenated bisphenol A diglycidyl ether, 3,4-epoxycyclohexylmethyl-3,4-epoxycyclohexane carboxylate, 3,4-epoxy-1-methylcyclohexyl-3,4-epoxy-1-methylcyclohexane carboxylate, 6-methyl-3,4-epoxycyclohexylmethyl-6-methyl-3,4-epoxycyclohexane carboxylate, 3,4-epoxy-3-methylcyclohexylmethyl-3,4-epoxy-3-methylcyclohexane carboxylate, 3,4-epoxy-5-methylcyclohexylmethyl-3,4-epoxy-5-methylcyclohexane carboxylate, 2-(3,4-epoxycyclohexyl-5,5-spiro-3,4-epoxy)cyclohexane-m-dioxane, bis(3,4-epoxycyclohexylmethyl) adipate, 3,4-epoxy-6-methylcyclohexyl carboxylate, methylene bis(3,4-epoxycyclohexane), dicyclopentadiene diepoxide, ethylene bis(3,4-epoxycyclohexane carboxylate), dioctyl epoxyhexahydrophthalate, and di-2-ethylhexyl epoxyhexahydrophthalate.

Examples of commercially available products that can be preferably used as the alicyclic epoxy resins can include UVR-6100, UVR-6105, UVR-6110, UVR-6128, and UVR-6200 (all manufactured by Union Carbide Corp.), Celloxide 2021, Celloxide 2021P, Celloxide 2081, Celloxide 2083, Celloxide 2085, Celloxide 2000, Celloxide 3000, Cyclomer A200, Cyclomer M100, Cyclomer M101, Epolead GT-301, Epolead GT-302, Epolead GT-401, Epolead GT-403, ETHB, and Epolead HD300 (all manufactured by Daicel Corp.), and KRM-2110 and KRM-2199 (all manufactured by Adeka Corp.).

Specific examples of the aromatic epoxy resins include, but are not limited to, polyglycidyl ether of polyhydric phenol having at least one aromatic ring or alkylene oxide adduct thereof, for example, glycidyl ether of bisphenol A, bisphenol F, or an alkylene oxide-added compound thereof, and epoxy novolac resins.

Examples of commercially available products that can be preferably used as the aromatic epoxy resins can include Epicoat 825, Epicoat 825, Epicoat 827, Epicoat 828, Epicoat 828US, Epicoat 828EL, Epicoat 828XA, Epicoat 834, Epicoat 806, Epicoat 806L, Epicoat 806H, Epicoat 807, 1750, YL980, and YL983U (all manufactured by Mitsubishi Chemical Corp.), EPICLON 840, EPICLON 840-S, EPICLON 850, EPICLON 850CRP, EPICLON 850LC, EPICLON 860, EPICLON 830, EPICLON 830S, EXA-83OLVP, EPICLON 835, and EXA-835LV (all manufactured by DIC Corp.), KRM-2720, EP-4100, EP-4100F, EP-4000, EP-4080, EP-4900, EP4901, ED-505, and ED-506 (all manufactured by Adeka Corp.), Epolight M-1230, Epolight EHDG-L, Epolight 40E, Epolight 100E, Epolight 200E, Epolight 400E, Epolight 70P, Epolight 200P, Epolight 400P, Epolight 1500NP, Epolight 1600, Epolight 80MF, Epolight 100MF, Epolight 4000, Epolight 3002, and Epolight FR-1500 (all manufactured by Kyoeisha Chemical Co., Ltd.), Santoto ST0000, YD-716, YH-300, PG-202, PG-207, YD-172, YDPN638, YD-8125, YD-825DS, YD-825GSH, and ZX-1059 (all manufactured by Nippon Steel & Sumikin Chemical Co., Ltd.), RE-310S, RE-303S-H, RE-303S-L, RE-602S, RE-305, RE-305S, and RE-306 (all manufactured by Nippon Kayaku Co., Ltd.), and D. E. R. 317, D.E.R. 330, D.E.R. 331, D.E.R. 332, D.E.R. 337, D.E.R. 362, D.E.R. 364, D.E.R. 383, D.E.R. 324, D.E.R. 325, D.E.R. 732, and D.E.R. 736 (all manufactured by The DOW Chemical Company).

Examples of commercially available products that can be preferably used as the aliphatic epoxy resins include YH-300, YH-301, YH-315, YH-324, and YH-325 (all manufactured by Nippon Steel & Sumikin Chemical Co., Ltd.), and EX-212L, EX-214L, EX-216L, EX-321L, and EX-850L (all manufactured by Nagase ChemteX Corp.).

Examples of the oxetane compounds can include, but are not particularly limited to, the following compounds: 3-ethyl-3-hydroxymethyloxetane, 3-(meth)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]

benzene, [1-(3-ethyl-3-oxetanylmethoxy)ethyl]phenyl ether, isobutoxymethyl(3-ethyl-3-oxetanylmethyl) ether, isobornyloxyethyl(3-ethyl-3-oxetanylmethyl) ether, isobornyl(3-ethyl-3-oxetanylmethyl) ether, 2-ethylhexyl(3-ethyl-3-oxetanylmethyl) ether, ethyl diethylene glycol(3-ethyl-3-oxetanylmethyl) ether, dicyclopentadiene(3-ethyl-3-oxetanylmethyl) ether, dicyclopentenyloxyethyl(3-ethyl-3-oxetanylmethyl) ether, dicyclopentenyl(3-ethyl-3-oxetanylmethyl) ether, tetrahydrofurfuryl(3-ethyl-3-oxetanylmethyl) ether, tetrabromophenyl(3-ethyl-3-oxetanylmethyl) ether, 2-tetrabromophenoxyethyl(3-ethyl-3-oxetanylmethyl) ether, tribromophenyl(3-ethyl-3-oxetanylmethyl) ether, 2-tribromophenoxyethyl(3-ethyl-3-oxetanylmethyl) ether, 2-hydroxyethyl(3-ethyl-3-oxetanylmethyl) ether, 2-hydroxypropyl(3-ethyl-3-oxetanylmethyl) ether, butoxyethyl(3-ethyl-3-oxetanylmethyl) ether, pentachlorophenyl(3-ethyl-3-oxetanylmethyl) ether, pentabromophenyl(3-ethyl-3-oxetanylmethyl) ether, bornyl(3-ethyl-3-oxetanylmethyl) ether, 3,7-bis(3-oxetanyl)-5-oxa-nonane, 3,3'-(1,3-(2-methylenyl)propanediylbis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl) ether, dicyclopentenyl bis(3-ethyl-3-oxetanylmethyl) ether, triethylene glycol bis(3-ethyl-3-oxetanylmethyl) ether, tetraethylene glycol bis(3-ethyl-3-oxetanylmethyl) ether, tricyclodecanediyl dimethylene(3-ethyl-3-oxetanylmethyl) ether, trimethylolpropane tris(3-ethyl-3-oxetanylmethyl) ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl) ether, pentaerythritol tetrakis(3-ethyl-3-oxetanylmethyl) ether, polyethylene glycol bis(3-ethyl-3-oxetanylmethyl) ether, dipentaerythritol hexakis(3-ethyl-3-oxetanylmethyl) ether, dipentaerythritol pentakis(3-ethyl-3-oxetanylmethyl) ether, dipentaerythritol tetrakis(3-ethyl-3-oxetanylmethyl) ether, caprolactone-modified dipentaerythritol hexakis(3-ethyl-3-oxetanylmethyl) ether, caprolactone-modified dipentaerythritol pentakis(3-ethyl-3-oxetanylmethyl) ether, ditrimethylolpropane tetrakis(3-ethyl-3-oxetanylmethyl) ether, EO-modified bisphenol A bis(3-ethyl-3-oxetanylmethyl) ether, PO-modified bisphenol A bis(3-ethyl-3-oxetanylmethyl) ether, EO-modified hydrogenated bisphenol A bis(3-ethyl-3-oxetanylmethyl) ether, PO-modified hydrogenated bisphenol A bis(3-ethyl-3-oxetanylmethyl) ether, and EO-modified bisphenol F(3-ethyl-3-oxetanylmethyl) ether. These oxetane compounds are effective, particularly, for use in the case of requiring flexibility and are preferred.

Other specific examples of the cationically polymerizable compound include, but are not limited to, well-known compounds including: oxolane compounds such as tetrahydrofuran and 2,3-dimethyltetrahydrofuran; cyclic acetal compounds such as trioxane, 1,3-dioxolane, and 1,3,6-trioxanecyclooctane; cyclic lactone compounds such as β-propiolactone and ε-caprolactone; thiirane compounds such as ethylene sulfide and thioepichlorohydrin; thietane compounds such as 1,3-propyne sulfide and 3,3-dimethylthietane; cyclic thioether compounds such as tetrahydrothiophene derivatives; vinyl ether compounds such as ethylene glycol divinyl ether, alkyl vinyl ether, 2-chloroethylvinyl ether, 2-hydroxyethyl vinyl ether, triethylene glycol divinyl ether, 1,4-cyclohexanedimethanol divinyl ether, hydroxybutyl vinyl ether, and propylene glycol propenyl ether; spiro-o-ester compounds obtained through the reaction of an epoxy compound with lactone; ethylenic unsaturated compounds such as styrene, vinylcyclohexene, isobutylene, and polybutadiene; and silicones.

The cationically polymerizable composition of the present embodiment may be further used, if necessary, as a mixture with a radical polymerizable organic compound and an energy beam-sensitive radical polymerization initiator.

The radical polymerizable organic compound that can be used in the present embodiment is a radical polymerizable organic compound that is highly polymerized or causes cross-linking reaction by irradiation with energy beam in the presence of the energy beam-sensitive radical polymerization initiator, and is preferably a compound having at least one or more unsaturated double bonds in one molecule.

Examples of the radical polymerizable organic compound include, but are not particularly limited to, acrylate compounds, methacrylate compounds, allylurethane compounds, unsaturated polyester compounds, and styrene compounds. Among these radical polymerizable organic compounds, a compound having a (meth)acryl group is preferred because of easy synthesis, availability, and handling. Examples thereof include epoxy (meth)acrylate, urethane (meth)acrylate, polyester (meth)acrylate, polyether (meth)acrylate, and (meth)acrylic acid esters of alcohols.

In this context, the epoxy (meth)acrylate is an acrylate obtained through the reaction of, for example, an aromatic epoxy resin, an alicyclic epoxy resin, or an aliphatic epoxy resin conventionally known in the art with (meth)acrylic acid. Among these epoxy (meth)acrylates, (meth)acrylate of an aromatic epoxy resin is particularly preferred. Such (meth)acrylate is (meth)acrylate obtained through the reaction of polyglycidyl ether of polyhydric phenol having at least one aromatic nucleus or an alkylene oxide adduct thereof with (meth)acrylic acid. Examples thereof include: (meth)acrylate obtained through the reaction of (meth)acrylic acid with glycidyl ether from bisphenol A or an alkylene oxide adduct thereof reacted with epichlorohydrin; and (meth)acrylate obtained through the reaction of an epoxy novolac resin with (meth)acrylic acid.

The urethane (meth)acrylate is preferably, for example, (meth)acrylate obtained through the reaction of one or two or more hydroxy group-containing polyesters or hydroxy group-containing polyethers with hydroxy group-containing (meth)acrylic acid ester and isocyanates, or (meth)acrylate obtained through the reaction of hydroxy group-containing (meth)acrylic acid ester with isocyanates.

Peroxide or an azo compound conventionally known in the art can be used as the radical polymerization initiator. Organic peroxide is preferred from the viewpoint of much better storage stability and cold rapid curing.

Examples of the organic peroxide include, but are not limited to, diacyl peroxide, peroxy dicarbonate, peroxy ester, peroxyketal, dialkyl peroxide, hydroperoxide, and silyl peroxide. Of them, peroxy ester or diacyl peroxide is preferred because of favorable stability and reactivity. The peroxy ester has a structure represented by —C(=O)—O—O—, and the diacyl peroxide has a structure represented by —C(=O)—O—O—C(=O)—. The organic peroxide is more preferably peroxy ester or diacyl peroxide having a 1-minute half-life temperature of 80 to 170° C. and a molecular weight of 180 to 1000. Such organic peroxide provides an initiator system having much better storage stability and cold rapid curing properties.

Specific examples thereof include cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-butyl peroxypivalate, 1, 1, 3, 3-tetramethylbutyl peroxy-2-ethylhexanoate, 2,5-dimethyl-2,5-di(2-ethylhexanoylperoxy)hexane, t-hexyl peroxy-2-ethylhexanoate, t-butyl peroxy-2-ethylhexanoate, t-butyl peroxyneoheptanoate, t-amyl peroxy-2-ethylhexanoate, di-t-butyl peroxyhexahydroterephthalate, t-amyl peroxy-3,5,5-trimethylhexanoate, 3-hydroxy-1,1-dimethylbutyl peroxyneodecanoate, 1,1,3,3-tetramethylbutyl peroxy-2-ethylhexanoate, t-amyl peroxyneodecanoate, t-amyl peroxy-2-ethylhexanoate, 2,2'-azobis-2,4-dimethylvaleronitrile, 1,1'-azobis(1-acetoxy-1-phenylethane), 2,2'-azobisisobutyronitrile, 2,2'-azobis(2-methylbutyronitrile), dimethyl-2,2'-azobisisobutyronitrile, 4,4'-azobis(4-cyanovaleric acid), 1,1'-azobis(1-cyclohexanecarbonitrile), t-hexylperoxyisopropyl monocarbonate, t-butylperoxymaleic acid, t-butylperoxy-3,5,5-trimethylhexanoate, t-butyl peroxylaurate, 2,5-dimethyl-2,5-di(3-methylbenzoylperoxy)hexane, t-butylperoxy-2-ethylhexyl monocarbonate, t-hexyl peroxybenzoate, 2,5-dimethyl-2,5-di(benzoylperoxy)hexane, t-butyl peroxybenzoate, dibutyl peroxytrimethyladipate, t-amyl peroxy-normal octoate, t-amyl peroxyisononanoate, t-amyl peroxybenzoate, and lauroyl peroxide.

One of these radical polymerization initiators may be used alone, or two or more thereof may be used in combination.

The cationically polymerizable composition of the present embodiment preferably contains a silane coupling agent as one binder component in order to improve adhesion strength for recipient surface. Examples of the silane coupling agent can include, but are not limited to, epoxy silane coupling agents and acrylic silane coupling agents. These silane coupling agents are alkoxysilane derivatives each having 1 to 3 lower alkoxy groups in the molecule and may have, in the molecule, a group having reactivity with a functional group in the cationically polymerizable compound, for example, a vinyl group, a styryl group, an acryloyloxy group, a methacryloyloxy group, an epoxy group, an amino group, or a mercapto group.

The cationically polymerizable composition of the present embodiment can be supplemented, if necessary, with an antioxidant, a softening agent, a colorant (pigment or dye), an organic solvent, an ion catcher, or the like.

Examples of the antioxidant include, but are not limited to, amine antioxidants, phenol antioxidants, phosphorous acid antioxidants, and benzimidazole antioxidants.

Examples of the amine antioxidants include, but are not limited to, amine-ketone antioxidants, aromatic secondary amine, thiourea, organic thioacid, and dithiocarbamic acid antioxidants.

Examples of the amine-ketone antioxidants include, but are not limited to, 2,2,4-trimethyl-1,2-dihydroquinoline polymers, 6-ethoxy-2,2,4-trimethyl-1,2-dihydroquinoline, reaction products of diphenylamine and acetone, and reaction products of aniline and acetone.

Examples of the aromatic secondary amine include, but are not limited to: alkylated diphenylamines such as octylated diphenylamine and di-tert-butyl-diphenylamine; and 4,4'-bis(α,α'-dimethylbenzyl)diphenylamine (=4,4'-dicumyl-diphenylamine), styrenated diphenylamine, p-(p-toluenesulfonylamido)diphenylamine, N-phenyl-N'-(3-methacryloyloxy-2-hydroxypropyl)-p-phenylenediamine, N-phenyl-1-naphthylamine, N-isopropyl-N'-phenyl-p-phenylenediamine, N,N'-diphenyl-p-phenylenediamine, N,N'-di-2-naphthyl-p-phenylenediamine, N-(1,3-dimethylbutyl)-N'-phenyl-p-phenylenediamine, N-(1-methylheptyl)-N'-phenyl-p-phenylenediamine, N,N'-methylene-bis-acrylamide, and phenothiazine derivatives.

Examples of the thiourea include, but are not limited to, 1,3-bis(dimethylaminopropyl)-2-thiourea, tributylthiourea, and thiourea derivatives represented by R1R2NC(=S)NR3R4 (R1 to R4 are each selected from hydrogen, an alkyl group, an alkoxy group, an alkyl group substituted by an alkylamino group or a dialkylamino group, a cycloalkyl group, and a phenyl group).

Examples of the thiourea derivatives include, but are not limited to, 1,3-diethyl-2-thiourea, 1,3-dibutyl-2-thiourea, 1-methoxypropyl-3-oxydiethylene-2-thiourea, 1-n-butyl-3-oxydiethylene-2-thiourea, ethylenethiourea(2-mercaptoimidazoline), 1-methoxypropyl-3-butyl-2-thiourea, 1-dimethylaminopropyl-3-butyl-2-thiourea, 1-methoxypropyl-3-cyclohexyl-2-thiourea, 1-dimethylaminopropyl-3-phenyl-2-thiourea, 1-diethylaminopropyl-3-oxydiethylene-2-thiourea, 1-methoxypropyl-3,3-dibutyl-2-thiourea, 1-dimethylaminopropyl-3,3-diisopropyl-2-thiourea, 1-diethylaminopropyl-3-methyl-3-cyclohexyl-2-thiourea, and 1-methoxypropyl-3-phenyl-3-cyclohexyl-2-thiourea.

Examples of the organic thioacid include, but are not limited to, dilauryl thiodipropionate.

Examples of the dithiocarbamic acid antioxidants include, but are not limited to, nickel dibutyldithiocarbamate.

Examples of the phenol antioxidants include, but are not limited to, monophenol antioxidants, bisphenol antioxidants, and polyphenol antioxidants.

Examples of the monophenol antioxidants include, but are not limited to, 2,6-di-tert-butyl-4-methylphenol, (α-methylbenzyl)phenol, di(α-methylbenzyl)phenol, tri(α-methylbenzyl)phenol, and styrenated phenol.

Examples of the bisphenol antioxidants include, but are not limited to, 4,4'-butylidene bis(3-methyl-6-tert-butylphenol), butylation reaction products of p-cresol and dicyclopentadiene, 4,4'-thio-bis(3-methyl-6-tert-butylphenol), 2,2'-methylene-bis(4-alkyl-6-tert-butylphenol) (e.g., 2,2'-methylene-bis(4-methyl-6-tert-butylphenol) and 2,2'-methylene-bis(4-ethyl-6-tert-butylphenol)), 2,2'-methylene-bis[6-(1-methylcyclohexyl-p-cresol)], and 2,2'-dihydroxy-3,3'-di(α-methylcyclohexyl)-5,5'-dimethyldiphenyl methane.

Examples of the polyphenol antioxidants include, but are not limited to, 2,5-di-tert-alkylhydroquinones such as 2,5-di-tert-amylhydroquinone and 2,5-di-tert-butylhydroquinone.

Examples of the phosphorous acid antioxidants include, but are not limited to, tris(nonylphenyl) phosphite.

Examples of the benzimidazole antioxidants include, but are not limited to, 2-mercaptobenzimidazole, 2-mercaptobenzimidazole zinc salt, and 2-mercaptomethylbenzimidazole.

Examples of the softening agent that can be used include, but are not limited to, general softening agents including: dibasic acid esters such as DOP (dioctyl phthalate), DINP (diisononyl phthalate), DINA (diisononyl adipate), DBP (dibutyl phthalate), TOTM (tri-2-ethylhexyl trimellitate), and DIDP (diisodecyl phthalate); liquid rubbers such as liquid polyisobutylene, liquid isoprene, and liquid butene; and aromatic process oil, naphthene process oil, paraffin oil, castor oil, and tall oil.

The colorant is not limited, and, for example, any of routine pigments and disperse dyes known in the art can be used. Also, these colorants can be used in combination, if necessary.

The pigments mainly include inorganic pigments, organic pigments, moisture-resistant pigments, and the like. In the present embodiment, any of these pigments can be used. Also, these pigments may be used in combination. For example, a moisture-resistant pigment may be added into an organic pigment to prepare an aqueous colored dispersion for inkjet.

Examples of the inorganic pigments include, but are not limited to, carbon black, metal oxide, hydroxide, sulfide, ferrocyanide, and metal chloride. Particularly, carbon black is preferred for black aqueous ink compositions. Examples of carbon black obtained by a pyrolysis method include thermal black and acetylene black. Examples of carbon black obtained by an incomplete combustion method include oil furnace black, gas furnace black, lamp black, gas black, and channel black. One of these carbon blacks may be used, or two or more of the carbon blacks may be used in combination.

A black pigment is not limited and is preferably, for example, a carbon black pigment such as furnace black, lamp black, acetylene black, or channel black. Specific examples of the carbon black include, but are not limited to: Raven 760 ULTRA, Raven 780 ULTRA, Raven 790 ULTRA, Raven 1060 ULTRA, Raven 1080 ULTRA, Raven 1170, Raven 1190 ULTRA II, Raven 1200, Raven 1250, Raven 1255, Raven 1500, Raven 2000, Raven 2500 ULTRA, Raven 3500, Raven 5000 ULTRA II, Raven 5250, Raven 5750, and Raven 7000 (all manufactured by Columbian Carbon Company); Monarch 700, Monarch 800, Monarch 880, Monarch 900, Monarch 1000, Monarch 1100, Monarch 1300, Monarch 1400, Regal 1330R, Regal 1400R, Regal 1660R, and Mogul L (all manufactured by Cabot Corp.); Color Black FW1, Color Black FW2, Color Black FW2V, Color Black FW200, Color Black 5150, Color Black 5160, Color Black 5170, Printex 35, Printex U, Printex V, Printex 140U, Printex 140V, Special Black 4, Special Black 4A, Special Black 5, and Special Black 6 (all manufactured by Degussa AG); and MA7, MA8, MA100, MA600, MCF-88, No. 25, No. 33, No. 40, No. 47, No. 52, No. 900, and No. 2300 (all manufactured by Mitsubishi Chemical Corp.).

Examples of the organic pigments include, but are not limited to, soluble azo pigments, insoluble azo pigments, insoluble diazo pigments, condensed azo pigments, phthalocyanine pigments, quinacridon pigments, isoindolinone pigments, dioxazine pigments, perylene pigments, perinone pigments, thioindigo pigments, anthraquinone pigments, and quinophthalone pigments. One of these organic pigments may be used, or two or more of the organic pigments may be used in combination. The organic pigments can also be used in combination with the inorganic pigments and can also be used in combination with the moisture-resistant pigments, etc., for improvement in fluidity.

Specific examples of the organic pigments include, but are not limited to: yellow pigments such as C.I. Pigment Yellow 1, 2, 3, 12, 13, 14, 16, 17, 24, 55, 73, 74, 75, 83, 93, 94, 95, 97, 98, 108, 114, 128, 129, 138, 139, 150, 151, 154, 180, 185, 193, 199, and 202; red pigments such as C.I. Pigment Red 5, 7, 12, 48, 48:1, 57, 88, 112, 122, 123, 146, 149, 166, 168, 177, 178, 179, 184, 185, 202, 206, 207, 254, 255, 257, 260, 264, and 272; blue pigments such as C.I. Pigment Blue 1, 2, 3, 15, 15:1, 15:2, 15:3, 15:4, 15:6, 16, 22, 25, 60, 66, and 80; violet pigments such as C.I. Pigment Violet 19, 23, 29, 37, 38, and 50; orange to brown pigments such as C.I. Pigment Orange 13, 16, 68, 69, 71, and 73; green pigments such as C.I. Pigment Green 7, 36, and 54; and black pigments such as C.I. Pigment Black 1.

Examples of the moisture-resistant pigments include, but are not limited to, silica, calcium carbonate, talc, clay, barium sulfate, and white carbon. These moisture-resistant pigments are usually used in combination with the inorganic pigments or the organic pigments without being used alone.

The disperse dyes are not limited, and, for example, a disperse dye known in the art such as an azobenzene disperse dye or an anthraquinone disperse dye may be used. One or more of these disperse dyes may be used in order to adjust a hue.

Preferred examples of the disperse dyes include, but are not limited to: C.I. Disperse Yellow 9, 23, 33, 42, 49, 54, 58, 60, 64, 66, 71, 76, 79, 83, 86, 90, 93, 99, 114, 116, 119, 122, 126, 149, 160, 163, 165, 180, 183, 186, 198, 200, 211, 224, 226, 227, 231, and 237; C.I. Disperse Red 60, 73, 88, 91, 92, 111, 127, 131, 143, 145, 146, 152, 153, 154, 167, 179, 191, 192, 206, 221, 258, and 283; C.I. Disperse Orange 9, 25, 29, 30, 31, 32, 37, 38, 42, 44, 45, 53, 54, 55, 56, 61, 71, 73, 76, 80, 96, and 97; C.I. Disperse Violet 25, 27, 28, 54, 57, 60, 73, 77, 79, and 79:1; and C.I. Disperse Blue 27, 56, 60, 79:1, 87, 143, 165, 165:1, 165:2, 181, 185, 197, 202, 225, 257, 266, 267, 281, 341, 353, 354, 358, 364, 365, and 368.

Examples of the organic solvent include, but are not limited to: carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and, 2-heptanone; polyhydric alcohols and derivatives thereof such as monomethyl ether, monoethyl ether, monopropyl ether, monobutyl ether, or monophenyl ether of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

Examples of the ion catcher include, but are not limited to: alkoxy aluminums such as trismethoxy aluminum, trisethoxy aluminum, trisisopropoxy aluminum, isopropoxydiethoxy aluminum, and trisbutoxy aluminum; phenoxy aluminums such as trisphenoxy aluminum and tris-p-methylphenoxy aluminum; and organic aluminum compounds such as trisacetoxy aluminum, trisstearatoaluminum, trisbutyratoaluminum, trispropionatoaluminum, tri sacetylacetonatoaluminum, tristrifluoroacetylacetonatoaluminum, tri sethylacetoacetatoaluminum, diacetylacetonatodipivaloylmethanatoaluminum, and diisopropoxy(ethylacetoacetato)aluminum. These components can be used alone or in combination of two or more thereof.

The cationically polymerizable composition of the present embodiment may also contain a stabilizer from the viewpoint of storage stability. Examples of the stabilizer include, but are not particularly limited to: guanidine compounds such as N,N'-dimethylguanidine and N,N'-diphenylguanidine; thiazole compounds such as 2-mercaptothiazole and 2-aminothiazole; thiourea compounds such as thiourea, ethylenethiourea, N,N-dimethylthiourea, N,N'-diethylthiourea, N,N'-dibutylthiourea, trimethylthiourea, triethylthiourea, dicyclohexylthiourea, tetramethylthiourea, and tetraethylthiourea; and alkylphenyl sulfide compounds such as 4-hydroxyphenylmethyl sulfide, 4-hydroxyphenylethyl sulfide, 4-hydroxyphenylbenzyl sulfide, and 4-methoxyphenylmethyl sulfide.

Other examples of the sulfonium salt added for stabilization to the cationically polymerizable composition of the present embodiment can include, but are not particularly limited to, benzyl-4-hydroxyphenylmethylsulfonium chloride, benzyl-4-hydroxyphenylethylsulfonium chloride, benzyl-4-hydroxyphenylmethyl methyl sulfate, p-chlorobenzyl-4-hydroxyphenylmethylsulfonium chloride, p-nitrobenzyl-4-hydroxyphenylmethylsulfonium chloride, o-methylbenzyl-4-hydroxyphenylmethylsulfonium chloride, m-methylbenzyl-4-hydroxyphenylmethylsulfonium chloride, benzyl-4-methoxyphenylmethylsulfonium chloride, benzyl-3-methyl-4-hydroxyphenylmethylsulfonium chloride, benzyl-3-methyl-4-hydroxy-5-tert-butylphenylmethylsulfonium chloride, α-naphthylmethyl-4-hydroxyphenylmethylsulfonium chloride, 4-hydroxyphenyldimethyl methyl sulfate, and 4-(benzyloxycarbonyloxy)phenyldimethyl methyl sulfate. One of these sulfonium salts can be used, or two or more thereof can be used in combination. These sulfonium salts may be dissolved, for use, in appropriate solvents (e.g., propylene carbonate, Carbitol, Carbitol acetate, and butyrolactone) in advance.

(Filler)

The cationically polymerizable composition of the present embodiment contains a filler from the viewpoint of adjusting the moisture resistance or linear expansion of a cured product of the composition. The filler is an inorganic filler or an organic filler, or a mixture thereof.

Examples of the organic filler include, but are not particularly limited to: fine particles selected from the group consisting of fine silicon particles, fine acrylic particles, fine styrene particles such as styrene-divinylbenzene copolymers, and fine polyolefin particles; and a wax selected from the group consisting of carnauba wax, microcrystalline wax, modified microcrystalline wax, Fischer-Tropsch wax, and modified Fischer-Tropsch wax.

Examples of the inorganic filler include, but are not particularly limited to, inorganic fillers such as calcium carbonate, magnesium carbonate, barium sulfate, magnesium sulfate, aluminum silicate, zirconium silicate, iron oxide, titanium oxide, aluminum oxide (alumina), zinc oxide, silicon dioxide, potassium titanate, kaolin, talc, glass beads, activated sericite earth, bentonite, aluminum nitride, and silicon nitride, and preferably include silicon dioxide, talc, silica, alumina, barium sulfate, talc, clay, mica powder, aluminum hydroxide, magnesium hydroxide, calcium carbonate, magnesium carbonate, magnesium oxide, boron nitride, aluminum borate, barium titanate, strontium titanate, calcium titanate, magnesium titanate, bismuth titanate, titanium oxide, barium zirconate, and calcium zirconate. Among them, silica is preferred.

The shape of the filler according to the present embodiment is not particularly limited and can be any of defined (spherical, plate-like, needle-like, etc.) and undefined shapes. A spherical filler is preferred from the viewpoint of highly filling very small gaps.

The inorganic filler according to the present embodiment is preferably silica such as amorphous silica, ground silica, fused silica, crystalline silica, synthetic silica, or hollow silica, more preferably fused silica. The silica is preferably spherical. One of these inorganic fillers may be used, or two or more thereof may be used in combination. Examples of commercially available spherical fused silica include "SOC1" and "SOC2" both manufactured by Admatechs Co., Ltd.

The average particle size of the inorganic filler according to the present embodiment is not particularly limited. The upper limit of the average particle size of the inorganic filler is preferably 5 μm or smaller, more preferably 3 μm or smaller, further preferably 1 μm or smaller, still further preferably 0.7 μm or smaller, even further preferably 0.5 μm or smaller, particularly preferably 0.4 μm or smaller, still particularly preferably 0.3 μm or smaller, from the viewpoint of forming micro wiring on an insulating layer. On the other hand, the lower limit of the average particle size of the inorganic filler is preferably 0.01 μm or larger, more preferably 0.03 μm or larger, further preferably 0.05 μm or larger, still further preferably 0.07 μm or larger, particularly preferably 0.1 μm or larger, from the viewpoint of preventing reduction in handleability caused by elevated viscosity of resin composition varnish prepared from the epoxy resin composition. The average particle size of the inorganic filler can be measured by a laser diffraction-scattering method based on the Mie-Streuung theory. Specifically, the average particle size can be determined by creating the volume-based particle size distribution of the inorganic filler using a laser diffraction particle size distribution measurement apparatus, and using a median diameter thereof as the average particle size. The inorganic filler is ultrasonically dispersed in water, and this dispersion can be preferably used as a measurement sample. LA-500, 750, 950, or the like manufactured by HORIBA, Ltd. can be used as the laser diffraction particle size distribution measurement apparatus.

When the cationically polymerizable composition contains an inorganic filler, the content thereof differs depending on properties required for the cationically polymerizable composition and is preferably 5 to 95% by mass, more preferably 10 to 90% by mass, further preferably 15 to 85% by mass, still further preferably 20 to 80% by mass, with respect to 100% by mass of nonvolatile components in the cationically polymerizable composition. When the content of the inorganic filler is 5% by mass or larger, a cured product tends to have a more favorable coefficient of thermal expansion. When the content is 95% by mass or smaller, a cured product tends to have adequate hardness and tends to secure adequate peeling strength.

[Underfill and Method for Producing Same]

Methods for producing the underfill according to the present embodiment and a cured product thereof employ the cationically polymerizable composition of the present embodiment. Therefore, the methods for producing the underfill according to the present embodiment and a cured product thereof produce an underfill and a cured product thereof that are excellent in cold curing properties and storage stability. Specifically, the underfill of the present embodiment contains the cationically polymerizable composition of the present embodiment. The connecting structure according to the present embodiment is obtained by the methods for producing the underfill according to the present embodiment and a cured product thereof. Therefore, the connecting structure according to the present embodiment can be a connecting structure having excellent impact resistance and moisture resistance and high reliability.

The methods for producing the underfill of the present embodiment and a cured product thereof are not particularly limited by curing and molding methods or curing and molding conditions, and various methods and conditions known in the art can be adopted. Preferably, curing is carried out in a hot oven first at 100 to 130° C. for 0.5 hours or longer and subsequently at 150 to 175° C. for 0.5 hours or longer. The heating at 100 to 130° C. for 0.5 hours or longer tends to be able to more effectively suppress voids generated after curing. The heating at 150 to 175° C. for 0.5 hours or longer tends to produce adequate curing properties.

[Thermally Cationically Polymerizable Composition]

The thermally cationically polymerizable composition of the present embodiment contains a binder component and the onium salt of the present embodiment.

The binder component contained in the thermally cationically polymerizable composition of the present embodiment plays a role in improving film-forming properties. Examples of the binder component can include, but are not limited to, phenoxy resins such as bisphenol A-type phenoxy resins, bisphenol F-type phenoxy resins, bisphenol A-bisphenol F mixed-type phenoxy resins, bisphenol A-bisphenol S mixed-type phenoxy resins, fluorene ring-containing phenoxy resins, and caprolactone-modified bisphenol A-type phenoxy resins.

The thermally cationically polymerizable composition of the present embodiment can contain an organic boron compound. The content of the organic boron compound differs depending on the type of the organic boron compound and is preferably 0.05 to 10 parts by mass, more preferably 0.5 to 10 parts by mass, with respect to 100 parts by mass of the binder component from the viewpoint of sufficiently securing the adhesive strength and conductive particle capture efficiency of a polymerized product of the thermally cationically polymerizable composition, from the viewpoint of sufficiently suppressing uplift generation at an adhesive interface, and from the viewpoint of securing the adequate film-forming properties of the thermally cationically polymerizable composition.

Examples of the cationically polymerizable compound that can be contained as the binder component constituting the thermally cationically polymerizable composition of the present embodiment include, but are not limited to, epoxy compounds, oxetane compounds, vinyl ether compounds, cyclic sulfide compounds, cyclic amine compounds, and cyclic organic silicon compounds. Among them, an epoxy compound can be preferably used from the viewpoint of the balance between curing properties and storage stability.

The thermally cationically polymerizable composition of the present embodiment described above can be molded into a film shape by a routine method and thereby usually used as a 10 to 50 μm thick insulating adhesive film. Such a film containing conductive particles can be preferably used as an anisotropically conductive adhesive film. Specifically, the anisotropically conductive adhesive film of the present embodiment has the thermally cationically polymerizable composition of the present embodiment and conductive particles. The anisotropically conductive adhesive film of the present embodiment thus constituted is placed between circuit boards and heated under pressure applied using a pressing tool so that the resin in the adhesive flows favorably and preferably fill the space between electrodes formed on the circuit boards while a portion of the conductive particles is caught between the electrodes facing each other to achieve electrical connection. Thus, the anisotropically conductive adhesive film of the present embodiment function as a film-shaped anisotropically conductive adhesive that maintains, by heating and application of pressure, fluidity that permits flowing into the space between electrodes on the circuit boards, and the electrical connection between the connected electrodes facing each other in a joined body.

The thermally cationically polymerizable composition of the present embodiment can be supplemented with conductive particles for use in anisotropically conductive adhesives known in the art in order to function as an anisotropically conductive adhesive. Examples thereof include particles of metals such as nickel, cobalt, silver, copper, gold, and palladium, and metal-coated resin particles, which have a particle size of 1 to 50 μm. Two or more types of these particles can be used in combination.

In the present embodiment, a dispersion method conventionally known in the art can be used, without particular limitations, as a method for dispersing the conductive particles. Examples of the method for dispersing the conductive particles into the binder resin, include, but are not limited to: a method which involves adding the conductive particles into the binder resin and then dispersing the conductive particles therein by kneading using a planetary mixer or the like; a method which involves uniformly dispersing the conductive particles into water or an organic solvent using a homogenizer or the like, then adding the dispersion into the binder resin, and dispersing the conductive particles therein by kneading using a planetary mixer or the like; and a method which involves diluting the binder resin with water or an organic solvent, etc., then adding the conductive particles to the dilution, and dispersing the conductive particles therein by kneading using a planetary mixer or the like.

The anisotropically conductive adhesive film of the present embodiment can be preferably used in a method for producing a connecting structure in which a terminal of a first electronic component is anisotropically conductively connected to a terminal of a second electronic component. Specifically, the method for producing a connecting structure according to the present embodiment is a method for producing a connecting structure having a configuration in which a terminal of a first electronic component is anisotropically conductively connected to a terminal of a second electronic component, the method including: (A) temporarily affixing the anisotropically conductive adhesive film of the present embodiment onto the terminal of the first electronic component; (B) temporarily disposing the second electronic component onto the anisotropically conductive adhesive film such that the terminal of the second electronic component is opposed to the corresponding terminal of the first electronic component; and (C) anisotropically conductively connecting the terminal of the first electronic component to the terminal of the second electronic component by heating using a heating unit with pressure applied to the second electronic component using a pressing unit. The method for producing a connecting structure according to the present embodiment thus constituted can produce a connecting structure having high positional accuracy. Hereinafter, the steps (A), (B), and (C) in the method for producing a connecting structure according to the present embodiment will be described in detail.

Step (A)

First, the anisotropically conductive adhesive film of the present embodiment is temporarily affixed onto the terminal of the first electronic component. In this context, the term "temporarily affix" means a process of: adjusting the temperature of the anisotropically conductive adhesive film to a predetermined temperature at which the anisotropically conductive adhesive film of the present embodiment exhibits fluidity and is not thermally cured; in this state, peeling off the anisotropically conductive adhesive film from a base film; and affixing the anisotropically conductive adhesive film onto a substrate or the like as the first electronic component mentioned later. The predetermined temperature is preferably set to the range of, for example, 30° C. to 120° C. in response to needs for lower temperatures. Examples of the first electronic component include, but are not limited to, glass circuit boards, rigid circuit boards, and flexible circuit boards. Examples of the terminals thereof include, but are not limited to, metal (e.g., copper, nickel, gold, and solder)

pads and bumps. An operation conventionally known in the art can be applied to the operation of temporarily affixing the anisotropically conductive adhesive film. The operation of temporarily affixing the anisotropically conductive adhesive film is not limited, and, for example, the film can be pressed using a pressure bonder having a hard head made of a metal or ceramic or an elastic head made of rubber or the like, or if necessary, with heating using this pressing bonder or another heating unit (e.g., a surface plate equipped with a heating apparatus) so as not to cause main polymerization.

Step (B)

Next, the second electronic component is temporarily disposed onto the anisotropically conductive adhesive film of the present embodiment such that the terminal of the second electronic component is opposed to the corresponding terminal of the first electronic component. In this context, the term "temporarily dispose" means a process of placing the electronic component (second electronic component) other than the temporarily affixed electronic component (first electronic component) onto the anisotropically conductive material. In this temporarily disposed state, the first electronic component is not yet anisotropically conductively connected to the second electronic component. Examples of the second electronic component include, but are not limited to, flexible circuit boards and IC chips. Examples of the terminals thereof include, but are not limited to, metal (e.g., copper, nickel, gold, and solder) pads and bumps. The operation of temporarily disposing the second electronic component is not particularly limited and can be carried out by an approach conventionally known in the art.

Step (C)

Next, the terminal of the first electronic component is anisotropically conductively connected to the terminal of the second electronic component by heating using a heating unit with pressure applied to the second electronic component using a pressing unit such as a pressing bonder. This can yield a connecting structure in which the terminal of the first electronic component is anisotropically conductively connected to the terminal of the second electronic component via the anisotropically conductive adhesive film of the present embodiment. The pressing unit such as a pressing bonder may be used as the heating unit in one embodiment, or other various heating units known in the art may be used in another embodiment. The temperature of the heating is not particularly limited and can be appropriately selected according to the purpose. The temperature is preferably 140° C. to 200° C. The pressure for the pressing is not particularly limited and can be appropriately selected according to the purpose. The pressure is preferably 0.1 MPa to 80 MPa. The time of the heating and the pressing is not particularly limited and can be appropriately selected according to the purpose. Examples of the time include 0.5 seconds to 120 seconds.

The connecting structure of the present embodiment is obtained by the method for producing a connecting structure according to the present embodiment. Therefore, the connecting structure of the present embodiment can produce anisotropically conductive connection with improved connection reliability.

The film-shaped connecting material of the present embodiment contains a cationically polymerizable compound, a binder component, and compounds B, wherein the compounds B contained are two or more types. In this context, the cationically polymerizable compound and the binder component are the same as those mentioned above.

<Cation Scavenger>

The cation scavenger can have any structure as long as the cation scavenger reacts with cation species generated by the pyrolysis of the cation-generating agent. The cation scavenger is preferably one or more cation scavengers selected from the group consisting of a thiourea compound, a 4-alkylthiophenol compound, and a 4-hydroxyphenyl-dialkylsulfonium salt.

Specific examples of the cation scavenger will be shown below. Examples of the thiourea compound include, but are not limited to, ethylenethiourea, N,N'-dibutylthiourea, and trimethylthiourea. Examples of the 4-alkylthiophenol compound include, but are not limited to, 4-methylthiophenol, 4-ethylthiophenol, and 4-butylthiophenol. Examples of the 4-hydroxyphenyl-dialkylsulfonium salt include, but are not limited to, 4-hydroxyphenyldimethylsulfonium methyl sulfate and 4-hydroxyphenyl-dibutylsulfonium methyl sulfate. Alternatively, an onium salt such as sulfonium salt, ammonium salt, or imidazole salt may be used and is preferred, particularly, for ion liquids, because of easy mixing.

The content of the cation scavenger in the film-shaped connecting material of the present embodiment is preferably 0.1 to 20 parts by mass with respect to 100 parts by mass of the cation-generating agent. The content of the cation scavenger is more preferably 0.5 to 10 parts by mass with respect to 100 parts by mass of the cation-generating agent. When the content of the cation scavenger is 0.1 parts by mass or larger, adequate storage stability tends to be able to be secured. When the content is 20 parts by mass or smaller, adequate curing properties tend to be able to be secured.

<Method for Producing Film-Shaped Connecting Material>

The film-shaped connecting material of the present embodiment may be a single-layer film or may be a film in which a plurality of films are layered. The method for producing the film-shaped connecting material of the present embodiment is not limited, and the film-shaped connecting material of the present embodiment can be produced, for example, by mixing in advance a cation-generating agent, an organic binder, and, if necessary, a cation scavenger and conductive particles in a solvent to prepare a coating solution, then applying the coating solution onto a separator by applicator coating or the like, and evaporating the solvent in an oven.

In the case of layering a plurality of films, a lamination method is preferred. Examples of the lamination method include, but are not limited to, a lamination method using a heat roll. For the lamination using a heat roll, the temperature of the heat roll is preferably a temperature lower than the temperature at which the cation-generating agent generates cation species. The temperature is preferably a temperature at least 10° C., more preferably at least 20° C., lower than the cation generation temperature.

Examples of the separator include, but are not limited to, polyethylene, polypropylene, polystyrene, polyester, PET, PEN, nylon, vinyl chloride, and polyvinyl alcohol films. Examples of a preferred resin for protector films include polypropylene and PET. The separator has preferably undergone surface treatment such as fluorine treatment, Si treatment, or alkyd treatment. The film thickness of the separator is preferably 20 μm or larger and 100 μm or smaller.

The film-shaped connecting material of the present embodiment is slit into a desired width, if necessary, and rewound in a reel form.

The film-shaped connecting material of the present embodiment can be suitably used for the purpose of connection of a liquid crystal display with TCP, TCP with FPC, or FPC with a print wiring substrate; flip chip packaging for directly implementing an IC chip onto a substrate, connection of solar cell electrodes, or mechanical connection without electrical connection.

<Method for Producing Connecting Structure and Connecting Structure>

The method for producing a connecting structure according to the present embodiment includes the step of interposing the film-shaped connecting material of the present embodiment between a pair of opposed circuit boards, followed by heating and application of pressure. Examples of the connection method using the film-shaped connecting material of the present embodiment include a connection method which involves: preparing a circuit board such as a glass substrate with a circuit and an electrode formed by ITO wiring or metal wiring, and a circuit member such as an IC chip with an electrode formed at a position to be paired with the electrode of the circuit board; affixing the film-shaped connecting material of the present embodiment to a position at which the circuit member is to be located on the circuit board; and next positioning the respective electrodes of the circuit board and the circuit member in register so as to be paired with each other, followed by thermal pressure bonding. Specifically, the connecting structure of the present embodiment is obtained by connecting a pair of opposed circuit boards via the film-shaped connecting material of the present embodiment. The connecting structure of the present embodiment thus constituted is prevented from generating warpage or voids and provides reliability. The method for producing a connecting structure according to the present embodiment thus constituted can preferably produce the connecting structure of the present embodiment.

The film-shaped connecting material, when affixed, can be heated under applied pressure in order to peel off the separator. The conditions for heating under applied pressure preferably involve applying, for example, heat at a temperature of 30° C. or higher and 80° C. or lower and a pressure of 0.1 MPa or larger and 1 MPa or smaller for 0.5 seconds or longer and 3 seconds or shorter.

The thermal pressure bonding for the connection is preferably carried out by heating in a temperature range of 120° C. or higher and 180° C. or lower (more preferably 130° C. or higher and 170° C. or lower, most preferably 140° C. or higher and 160° C. or lower) and application of pressure ranging from 0.1 MPa or larger and 50 MPa or smaller (more preferably 0.5 MPa or larger and 40 MPa or smaller) for 3 seconds or longer and 15 seconds or shorter (more preferably 4 seconds or longer and 12 seconds or shorter) against the circuit member area.

The opposed substrates to be connected are preferably connected with the difference between their temperatures set to 120° C. or less, more preferably 100° C. or less, further preferably 70° C. or less. The difference between the respective temperatures of the substrates can be measured by placing a thermocouple onto each of the opposed substrates to be connected.

Higher connection reliability tends to be obtained by keeping the desired temperature range, pressure range, affixing or thermal pressure bonding time, and difference between the substrate temperatures mentioned above. In addition, this approach is advantageous for connecting low heat-resistant substrates. As a result, there is a tendency to be able to provide electrical connection of circuit boards that can suppress substrate warpage and advantageously shortens the engineering time.

EXAMPLES

Hereinafter, specific embodiments for carrying out the present embodiment will be described with reference to Examples, Comparative Examples, and Reference Examples. However, these examples are given merely for more specifically illustrating the contents of the present embodiment and do not limit the present embodiment by any means. In Examples and Comparative Examples, "part" and "%" are based on mass, unless otherwise specified.

<Structural Determination and Quantitative Determination of Compounds A and B>

In all of Examples, Comparative Examples, and Reference Examples, the compounds A and B were structurally determined by 1H-NMR (JNM-GX400, manufactured by JEOL Ltd.) and LC-MS (UPLC manufactured by Waters Corp.+Synapt G2 manufactured by Waters Corp.). The ratio of the mass of the compound B to the total mass of the compound A and the compound B and the masses of the compound A and the compound B were measured using UPLC (manufactured by Waters Corp.) and calculated from the area ratio of each observed peak. The results of analyzing the structure of the compound B obtained in each example according to these procedures are shown in each table in formats corresponding to $R_7$ to $R_{10}$ in the general formula (2) mentioned above. $R_7$ is a phenyl group having a structure in which one hydrogen atom in the benzene ring is replaced with a predetermined functional group $R_7'$. This $R_7'$ is shown alone in each table. In each table, "$R_1$ of compound A"="$R_7$ of compound B", "$R_2$ of compound A"="$R_8$ of compound B", "$R_3$ of compound A"="$R_9$ of compound B", and "$R_6$ of compound A"="$R_{10}$ of compound B". In the general formula (1), X was S, m was 1, and n was 1. The aforementioned mass ratio of each example is also shown in each table (simply indicated as "Mass ratio" in all tables; unit: %).

The results of LC-MS obtained using a sample of Example 1 mentioned later are shown in FIGS. 1 to 4. FIG. 1 shows a spectrum indicating the LC analysis results. The results of analyzing peaks 1, 3, and 6 in FIG. 1 by MS are shown in FIGS. 2, 3, and 4, respectively. FIG. 2 corresponds to compound B, and FIGS. 3 and 4 correspond to compound A. The detailed measurement conditions for LC-MS were as follows: a mixture of the compounds A and B obtained in Example 1 was prepared as a sample into a 10 mg/mL solution in AcCN and diluted 20-fold with water, and a centrifugal supernatant of the resulting solution was subjected to the LC-MS measurement.

(1) LC

Apparatus: UPLC manufactured by Waters Corp.
Column: Supelco, Ascentis Express RP-Amide (2.1 mm I.D.×50 mm)
Column temperature: 40° C.
Detection: PDA 210-400 nm
Flow rate: 0.2 mL/min
Mobile phase: A=water (0.1% HCOOH); B=acetonitrile
Gradient:

| Time (min) | A (%) | B (%) |
|---|---|---|
| 0 | 100 | 0 |
| 10 | 0 | 100 |
| 15 | 0 | 100 |
| 16 | 100 | 0 |
| 25 | 95 | 0 |

Injection volume: 1 μL
(2) MS
Apparatus: Synapt G2 manufactured by Waters Corp.
Ionization: ESI+
Scan range: m/z50 to 1200

Examples 1 to 39 and Reference Examples 1, 2, and A

[Evaluation]

The compounds produced in Examples 1 to 39 and Reference Examples 1, 2, and A mentioned later were evaluated as follows:

(1) Cold Curing Properties 1.0 part by mass of the compound produced in each example was uniformly mixed with 100 parts by mass of AER 2603 (manufactured by Asahi Kasei E-materials Corp.). The mixture (composition) thus obtained was used as a sample and subjected to differential scanning calorimetry (DSC) to measure an exothermic peak. The measurement was conducted using a differential scanning calorimeter (differential scanning calorimetry system "EXSTAR 6000" manufactured by SII Nanotechnology Inc.) by heating the sample in an amount of 10 mg from 40° C. to 300° C. at a heating rate of 10° C./min under a nitrogen stream. The temperature at which the exothermic peak was thus measured was evaluated as described below. Specifically, a sample rated as "A" or "B" was determined to have cold curing properties.

"A": lower than 95° C.
"B": 95° C. or higher and lower than 115° C.
"C": 115° C. or higher and lower than 135° C.
"D": 135° C. or higher (2) Amount of Curing Agent The compound produced in each example was uniformly mixed with 100 parts by mass of AER 2603 (manufactured by Asahi Kasei E-materials Corp.). The amount of the compound of each example mixed was set to 0.1, 0.2, 0.4, 0.5, 1.0, 1.2, 1.5, 2.0, 2.5, and 3.0 parts by mass to prepare mixtures. The gross heating value of each prepared mixture was measured by differential scanning calorimetry (DSC). The gross heating value is increased with increases in sulfonium salt. The amount of the curing agent that offered the maximum gross heating value was defined as the "minimum amount of the curing agent". The measurement was conducted using a differential scanning calorimeter (differential scanning calorimetry system "EXSTAR 6000" manufactured by SII Nanotechnology Inc.) by heating the sample in an amount of 10 mg from 40° C. to 300° C. at a heating rate of 10° C./min under a nitrogen stream. A sample rated as "A" or "B" was determined to have adequate curing performance with a small amount of the curing agent.

"A": smaller than 0.4 parts by mass
"B": 0.4 parts by mass or larger and smaller than 1.0 part by mass
"C": 1.0 part by mass or larger and smaller than 2.0 parts by mass
"D": 2.0 parts by mass or larger (3) Storage Stability The composition prepared in the evaluation of (2) Cold curing properties was stored at 30° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as "A" or "B" was determined to have adequate storage stability.

"A": less than 2-fold increase in the viscosity after storage
"B": 2-fold or more and less than 5-fold increase in the viscosity after storage
"C": 5-fold or more and less than 10-fold increase in the viscosity after storage
"D": 10-fold or more increase in the viscosity after storage, or gelled Example 1

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.80 parts by mass of compound 1. The ratio of the mass of the compound B to the total mass of the compound B and the compound A was 0.970. The yield with respect to 4-methoxythioanisole was 80.0%. The mass of the compound B was 7.57 g, and the mass of the compound A was 0.23 g.

Example 2

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of compound 2. The ratio of the mass of the compound B to the total mass of the compound B and the compound A was 0.972. The yield with respect to 4-methylthiophenol was 82%. The mass of the compound B was 7.66 g, and the mass of the compound A was 0.22 g.

Example 3

1.25 parts by mass of 4-methylthiotoluene, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.17 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.08 parts by mass of compound 3. The ratio of the mass of the compound B to the total mass of the compound B and the compound A was 0.971. The yield with respect to 4-methylthiotoluene was 75%. The mass of the compound B was 6.87 g, and the mass of the compound A was 0.21 g.

Example 4

1.53 parts by mass of 4-methylthioacetophenone, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.42 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.49 parts by mass of compound 4. The ratio of the mass of the compound B to the total mass of the compound B and the compound A was 0.969. The yield with respect to 4-methylthioacetophenone was 77%. The mass of the compound B was 7.26 g, and the mass of the compound A was 0.23 g.

Example 5

1.69 parts by mass of 4-acetoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.57 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.81 parts by mass of compound 5. The ratio of the mass of the compound B to the total mass of the compound B and the compound A was 0.967. The yield with respect to 4-acetoxythioanisole was 79%. The mass of the compound B was 7.55 g, and the mass of the compound A was 0.26 g.

Example 6

1.99 parts by mass of 4-methyl carbonate thioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.84 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.64 parts by mass of compound 6. The ratio of the mass of the compound B to the total mass of the compound B and the compound A was 0.974. The yield with respect to 4-methyl carbonate thioanisole was 75%. The mass of the compound B was 7.44 g, and the mass of the compound B was 0.20 g.

Example 7

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.70 parts by mass of compound 7. The ratio of the mass of the compound B to the total mass of the compound B and the compound A was 0.962. The yield with respect to 4-fluorothioanisole was 80%. The mass of the compound B was 7.41 g, and the mass of the compound A was 0.29 g.

Example 8

1.39 parts by mass of 4-methylthioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.30 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.09 parts by mass of compound 8. The ratio of the mass of the compound B to the total mass of the compound B and the compound A was 0.973. The yield with respect to 4-methylthioanisole was 74%. The mass of the compound B was 6.90 g, and the mass of the compound A was 0.19 g.

Example 9

1.43 parts by mass of thioanisole 4-fluoride, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 1.56 parts by mass of lithium trifluoromethanesulfonate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 3.24 parts by mass of compound 9. The ratio of the mass of the compound B to the total mass of the compound B and the compound A was 0.965. The yield with respect to thioanisole 4-fluoride was 75%. The mass of the compound B was 3.13 g, and the mass of the compound A was 0.11 g.

Example 10

1.60 parts by mass of 4-chlorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 1.56 parts by mass of lithium trifluoromethanesulfonate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 3.19 parts by mass of compound 10. The ratio of the mass of the compound B to the total mass of the compound B and the compound A was 0.972. The yield with respect to 4-chlorothioanisole was 71%. The mass of the compound B was 3.10 g, and the mass of the compound A was 0.09 g.

Example 11

2.04 parts by mass of 4-bromothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.88 parts by mass of the obtained precipitate, 1.56 parts by mass of lithium trifluoromethanesulfonate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 4.05 parts by mass of compound 11. The ratio of the mass of the compound B to the total mass of the compound B and the compound A was 0.970. The yield with respect to 4-bromothioanisole was 82%. The mass of the compound B was 3.93 g, and the mass of the compound A was 0.12 g.

Example 12

1.55 parts by mass of 4-methoxythioanisole, 1.95 parts by mass of silver borofluoride, 1.41 parts by mass of α-chloro-o-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.41 parts by mass of compound 12. The ratio of the mass of the compound B to the total mass of the compound B and the compound A was 0.974. The yield with respect to 4-methoxythioanisole was 79%. The mass of the compound B was 7.22 g, and the mass of the compound A was 0.19 g.

Example 13

1.55 parts by mass of 4-methoxythioanisole, 1.95 parts by mass of silver borofluoride, 1.41 parts by mass of α-chloro-p-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.60 parts by mass of compound 13. The ratio of the mass of the compound B to the total mass of the compound B and the compound A was 0.962. The yield with respect to 4-methoxythioanisole was 81%. The mass of the compound B was 7.31 g, and the mass of the compound A was 0.29 g.

Example 14

1.55 parts by mass of 4-methoxythioanisole, 1.95 parts by mass of silver borofluoride, 1.41 parts by mass of α-chloro-m-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.50 parts by mass of compound 14. The ratio of the mass of the compound B to the total mass of the compound B and the compound A was 0.968. The yield with respect to 4-methoxythioanisole was 80%. The mass of the compound B was 7.26 g, and the mass of the compound A was 0.24 g.

Example 15

1.55 parts by mass of 4-methoxythioanisole, 1.95 parts by mass of silver borofluoride, 0.91 parts by mass of 1-chloro-2-butene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 2.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.66 parts by mass of compound 15. The ratio of the mass of the compound B to the total mass of the compound B and the compound A was 0.972. The yield with respect to 4-methoxythioanisole was 75%. The mass of the compound B was 6.47 g, and the mass of the compound A was 0.19 g.

Example 16

1.55 parts by mass of 4-methoxythioanisole, 1.95 parts by mass of silver borofluoride, 2.26 parts by mass of 9-chloromethylanthracene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 4.32 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.50 parts by mass of compound 16. The ratio of the mass of the compound B to the total mass of the compound B and the compound A was 0.968. The yield with respect to 4-methoxythioanisole was 83%. The mass of the compound B was 8.23 g, and the mass of the compound A was 0.27 g.

Example 17

1.55 parts by mass of 4-methoxythioanisole, 1.95 parts by mass of silver borofluoride, 2.03 parts by mass of 4-(chloromethyl) biphenyl, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the product was washed. The solvent was distilled off under reduced pressure from the organic layer to obtain 8.10 parts by mass of compound 17. The ratio of the mass of the compound B to the total mass of the compound B and the compound A was 0.974. The yield with respect to 4-methoxythioanisole was 81%. The mass of the compound B was 7.89 g, and the mass of the compound A was 0.21 g.

Example 18

1.55 parts by mass of 4-methoxythioanisole, 1.95 parts by mass of silver borofluoride, 2.03 parts by mass of chlorodiphenylmethane, and 13.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 4.22 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.40 parts by mass of compound 18. The ratio of the mass of the compound B to the total mass of the compound B and the compound A was 0.982. The yield with respect to 4-methoxythioanisole was 74%. The mass of the compound B was 7.27 g, and the mass of the compound A was 0.13 g.

Example 19

1.55 parts by mass of 4-methoxythioanisole, 1.95 parts by mass of silver borofluoride, 1.77 parts by mass of 2-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.31 parts by mass of compound 19. The ratio of the mass of the compound B to the total mass of the compound B and the compound A was 0.968. The yield with respect to 4-methoxythioanisole was 75%.

Example 20

1.55 parts by mass of 4-methoxythioanisole, 1.95 parts by mass of silver borofluoride, 1.57 parts by mass of p-methoxybenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.06 parts by mass of compound 20. The ratio of the mass of the compound B to the total mass of the compound B and the compound A was 0.965. The yield with respect to 4-methoxythioanisole was 74%. The mass of the compound B was 6.81 g, and the mass of the compound A was 0.25 g.

Example 21

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 3.98 parts by mass of lithium tetrakis(p-fluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 4.87 parts by mass of compound 21. The ratio of the mass of the compound B to the total mass of the compound B and the compound A was 0.975. The yield with respect to 4-methoxythioanisole was 73%. The mass of the compound B was 4.75 g, and the mass of the compound A was 0.12 g.

Example 22

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 3.82 parts by mass of lithium tetrakis(p-methyl-phenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 4.69 parts by mass of compound 22. The ratio of the mass of the compound B to the total mass of the compound B and the compound A was 0.974. The yield with respect to 4-methoxythioanisole was 72%. The mass of the compound B was 4.57 g, and the mass of the compound A was 0.12 g.

Example 23

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.44 parts by mass of the obtained precipitate, 1.56 parts by mass of lithium trifluoromethanesulfonate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 3.87 parts by mass of compound 23. The ratio of the mass of the compound B to the total mass of the compound B and the compound A was 0.965. The yield with respect to 4-methoxythioanisole was 87%. The mass of the compound B was 3.73 g, and the mass of the compound A was 0.14 g.

Example 24

1.68 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.57 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.91 parts by mass of compound 24. The ratio of the mass of the compound B to the total mass of the compound B and the compound A was 0.952. The yield with respect to 4-methoxythioanisole was 80.0%. The mass of the compound B was 7.53 g, and the mass of the compound A was 0.38 g.

Example 25

1.82 parts by mass of 4-(n-propylthio)phenyl ether, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.69 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.32 parts by mass of compound 25. The ratio of the mass of the compound B to the total mass of the compound B and the compound A was 0.963. The yield with respect to 4-(n-propylthio)phenyl ether was 80.3%. The mass of the compound B was 8.01 g, and the mass of the compound A was 0.31 g.

Example 26

1.82 parts by mass of 4-(iso-propylthio)phenyl ether, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.69 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.32 parts by mass of compound 26. The ratio of the mass of the compound B to the total mass of the compound B and the compound A was 0.962. The yield with respect to 4-(iso-propylthio)phenyl ether was 80.3%. The mass of the compound B was 8.00 g, and the mass of the compound A was 0.32 g.

Example 27

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.82 parts by mass of compound 27. The ratio of the mass of the compound B to the total mass of the compound B and the compound A was 0.985. The yield with respect to 4-methoxythioanisole was 70.0%. The mass of the compound B was 6.72 g, and the mass of the compound A was 0.10 g.

Example 28

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.99 parts by mass of compound 28. The ratio of the mass of the compound B to the total mass of the compound B and the compound A was 0.900. The yield with respect to 4-methoxythioanisole was 82%. The mass of the compound B was 7.19 g, and the mass of the compound A was 0.80 g.

Example 29

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.28 parts by mass of compound 29. The ratio of the mass of the compound B to the total mass of the compound B and the compound A was 0.550. The yield with respect to 4-methoxythioanisole was 85%. The mass of the compound B was 4.55 g, and the mass of the compound A was 3.73 g.

Example 30

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.72 parts by mass of compound 30. The ratio of the mass of the compound B to the total mass of the compound B and the compound A was 0.985. The yield with respect to 4-methylthiophenol was 70%. The mass of the compound B was 6.62 g, and the mass of the compound A was 0.10 g.

Example 31

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of compound 31. The ratio of the mass of the compound B to the total mass of the compound B and the compound A was 0.900. The yield with respect to 4-methylthiophenol was 82%. The mass of the compound B was 7.09 g, and the mass of the compound A was 0.79 g.

Example 32

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.16 parts by mass of compound 32. The ratio of the mass of the compound B to the total mass of the compound B and the compound A was 0.550. The yield with respect to 4-methylthiophenol was 85%. The mass of the compound B was 4.49 g, and the mass of the compound A was 3.67 g.

Example 33

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.74 parts by mass of compound 33. The ratio of the mass of the compound B to the total mass of the compound B and the compound A was 0.985. The yield with respect to 4-fluorothioanisole was 70%. The mass of the compound B was 6.64 g, and the mass of the compound A was 0.10 g.

Example 34

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.89 parts by mass of compound 34. The ratio of the mass of the compound B to the total mass of the compound B and the compound A was 0.900. The yield with respect to 4-fluorothioanisole was 82%. The mass of the compound B was 7.10 g, and the mass of the compound A was 0.79 g.

Example 35

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.18 parts by mass of compound 35. The ratio of the mass of the compound B to the total mass of the compound B and the compound A was 0.550. The yield with respect to 4-fluorothioanisole was 85%. The mass of the compound B was 4.50 g, and the mass of the compound A was 3.68 g.

Example 36

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.09 parts by mass of lithium tetrakis(monofluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.80 parts by mass of compound 36. The ratio of the mass of the compound B to the total mass of the compound B and the compound A was 0.930. The yield with respect to 4-methoxythioanisole was 81.0%. The mass of the compound B was 7.57 g, and the mass of the compound A was 0.51 g.

Example 37

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.09 parts by mass of lithium tetrakis(monofluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.52 parts by mass of compound 37. The ratio of the mass of the compound B to the total mass of the compound B and the compound A was 0.940. The yield with respect to 4-methoxythioanisole was 82.0%. The mass of the compound B was 7.07 g, and the mass of the compound A was 0.45 g.

Example 38

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.09 parts by mass of lithium tetrakis(monofluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.77 parts by mass of compound 38. The ratio of the mass of the compound B to the total mass of the compound B and the compound A was 0.935. The yield with respect to 4-methoxythioanisole was 83.0%. The mass of the compound B was 7.26 g, and the mass of the compound A was 0.51 g.

Reference Example A 1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of compound 39. The ratio of the mass of the compound B to the total mass of the compound B and the compound A was adjusted to 1.0 by separation and purification by gel column chromatography.

Example 39

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of compound 40. The ratio of the mass of the compound B to the total mass of the compound B and the compound A was adjusted to 0.10 by separation and purification by gel column chromatography.

Reference Example 1

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether to obtain 3.90 parts by mass of compound 41. The ratio of the mass of the compound B to the total mass of the compound B and the compound A was 0.997. The yield with respect to 4-methoxythioanisole was 10.0%. The mass of the compound B was 0.38883 g, and the mass of the compound A was 0.00117 g.

Reference Example 2

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.65 parts by mass of compound 42. The ratio of the mass of the compound B to the total mass of the compound B and the compound A was 0.450. The yield with respect to 4-methylthiophenol was 90%. The mass of the compound B was 3.89 g. The mass of the compound A was 4.76 g.

These results are shown in Tables 1 to 8. The sulfonium salts of each Example and Reference Example were confirmed to have excellent balance among cold curing properties, the amount of the curing agent, and storage stability. Particularly, the sulfonium salts of Examples 1 to 39 and Reference Example A were confirmed to be superior in balance among cold curing properties, the amount of the curing agent, and storage stability.

TABLE 1

| Segment | Example 1 | Example 2 | Example 3 | Example 4 |
|---|---|---|---|---|
| R10 | $B^-\!\!-\!\!\left(\!\!\begin{array}{c}C_6F_5\end{array}\!\!\right)_4$ | $B^-\!\!-\!\!\left(\!\!\begin{array}{c}C_6F_5\end{array}\!\!\right)_4$ | $B^-\!\!-\!\!\left(\!\!\begin{array}{c}C_6F_5\end{array}\!\!\right)_4$ | $B^-\!\!-\!\!\left(\!\!\begin{array}{c}C_6F_5\end{array}\!\!\right)_4$ |

TABLE 1-continued

| | | | | |
|---|---|---|---|---|
| R7' | —O—CH₃ | —OH | —H | 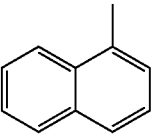 |
| R8 | —CH₃ | —CH₃ | —CH₃ | —CH₃ |
| R9 | 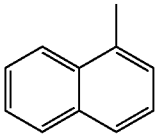 | 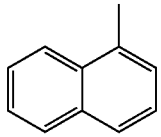 | 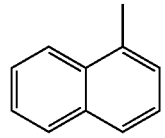 | 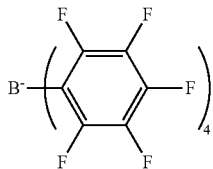 |
| Mass ratio | 97.0 | 97.2 | 97.1 | 96.9 |
| Cold curing properties | A | A | A | A |
| Amount of curing agent | A | A | A | A |
| Storage stability | A | A | A | A |

| Segment | Example 5 | Example 6 | Example 7 | Example 8 |
|---|---|---|---|---|
| R10 | 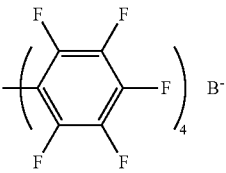 | 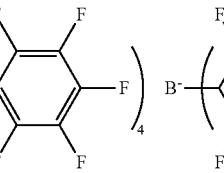 | 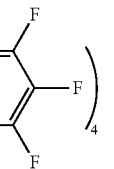 | 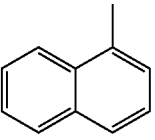 |
| R7' | 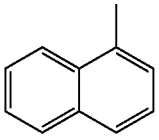 | 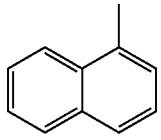 | —F | —CH₃ |
| R8 | —CH₃ | —CH₃ | —CH₃ | —CH₃ |
| R9 | 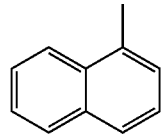 | 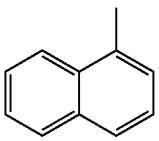 | 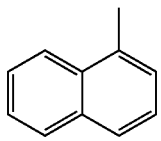 | 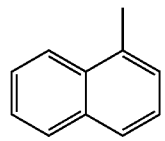 |
| Mass ratio | 96.7 | 97.4 | 96.2 | 97.3 |
| Cold curing properties | A | A | A | A |
| Amount of curing agent | A | A | A | A |
| Storage stability | A | A | A | A |

| Segment | Example 9 | Example 10 | Example 11 |
|---|---|---|---|
| R10 | CF₃SO₃⁻ | CF₃SO₃⁻ | CF₃SO₃⁻ |
| R7' | —F | —Cl | —Br |
| R8 | —CH₃ | —CH₃ | —CH₃ |
| R9 | (1-naphthyl) | (1-naphthyl) | (1-naphthyl) |
| Mass ratio | 96.5 | 97.2 | 97.0 |
| Cold curing properties | B | B | B |

TABLE 1-continued

|  | | | |
|---|---|---|---|
| Amount of curing agent | A | A | A |
| Storage stability | A | A | A |

TABLE 2

| Segment | Example 12 | Example 13 | Example 14 | Example 15 | Example 16 |
|---|---|---|---|---|---|
| R10 | B⁻−(C₆F₅)₄ | B⁻−(C₆F₅)₄ | B⁻−(C₆F₅)₄ | B⁻−(C₆F₅)₄ | B⁻−(C₆F₅)₄ |
| R7' | —O—CH₃ | —O—CH₃ | —O—CH₃ | —O—CH₃ | —O—CH₃ |
| R8 | —CH₃ | —CH₃ | —CH₃ | —CH₃ | —CH₃ |
| R9 | o-tolyl (2-methylphenyl) | p-tolyl (4-methylphenyl) | m-tolyl (3-methylphenyl) | —CH=CH— (vinyl) | 9-anthracenyl |
| Mass ratio | 97.4 | 96.2 | 96.8 | 97.2 | 96.8 |
| Cold curing properties | A | A | A | A | A |
| Amount of curing agent | B | B | B | B | B |
| Storage stability | A | A | A | A | A |

| Segment | Example 17 | Example 18 | Example 19 | Example 20 |
|---|---|---|---|---|
| R10 | B⁻−(C₆F₅)₄ | B⁻−(C₆F₅)₄ | B⁻−(C₆F₅)₄ | B⁻−(C₆F₅)₄ |
| R7' | —O—CH₃ | —O—CH₃ | —O—CH₃ | —O—CH₃ |
| R8 | —CH₃ | —CH₃ | —CH₃ | —CH₃ |
| R9 | 4-biphenylyl | diphenylmethyl (—CH(C₆H₅)₂) | 2-naphthyl | 4-methoxyphenyl |
| Mass ratio | 97.4 | 98.2 | 96.8 | 96.5 |
| Cold curing properties | A | A | A | A |

TABLE 2-continued

| Amount of curing agent | B | B | B | B |
|---|---|---|---|---|
| Storage stability | A | A | A | A |

TABLE 3

| Segment | Example 21 | Example 22 | Example 23 |
|---|---|---|---|
| R10 | B⁻−(C₆H₄−F)₄ | B⁻−(C₆H₄−CH₃)₄ | $CF_3SO_3^-$ |
| R7' | —O—CH₃ | —O—CH₃ | —O—CH₃ |
| R8 | —CH₃ | —CH₃ | —CH₃ |
| R9 | naphthyl | naphthyl | naphthyl |
| Mass ratio | 97.5 | 97.4 | 96.5 |
| Cold curing properties | B | B | B |
| Amount of curing agent | A | A | A |
| Storage stability | A | A | A |

TABLE 4

| Segment | Example 24 | Example 25 | Example 26 |
|---|---|---|---|
| R10 | B⁻−(C₆F₅)₄ | B⁻−(C₆F₅)₄ | B⁻−(C₆F₅)₄ |
| R7' | —O—CH₃ | —O—CH₃ | —O—CH₃ |
| R8 | —CH₂CH₃ | —CH₂CH₂CH₃ | —CH(CH₃)₂ |
| R9 | naphthyl | naphthyl | naphthyl |
| Mass ratio | 95.2 | 96.5 | 96.2 |
| Cold curing properties | A | A | A |
| Amount of curing agent | A | A | A |
| Storage stability | B | B | B |

TABLE 5

| Segment | Example 27 | Example 28 | Example 29 | Example 30 | Example 31 |
|---|---|---|---|---|---|
| R10 | 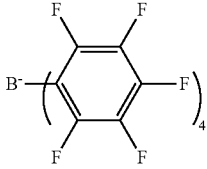 | 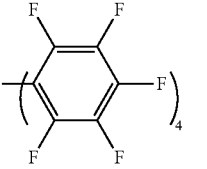 | 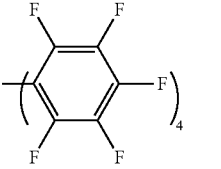 | 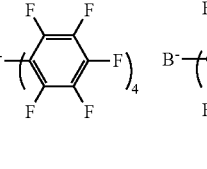 | 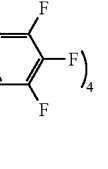 |
| R7' | —O—$CH_3$ | —O—$CH_3$ | —O—$CH_3$ | —OH | —OH |
| R8 | —$CH_3$ | —$CH_3$ | —$CH_3$ | —$CH_3$ | —$CH_3$ |
| R9 | 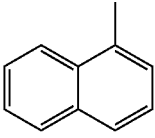 | 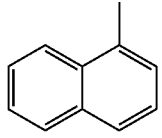 | 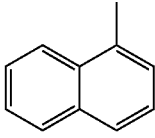 | 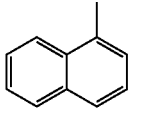 | 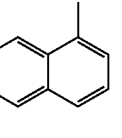 |
| Mass ratio | 98.4 | 90.0 | 55.0 | 98.4 | 90.0 |
| Cold curing properties | A | A | A | A | A |
| Amount of curing agent | B | A | A | B | A |
| Storage stability | A | A | B | A | A |

| Segment | Example 32 | Example 33 | Example 34 | Example 35 |
|---|---|---|---|---|
| R10 | 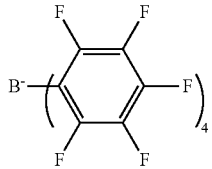 | 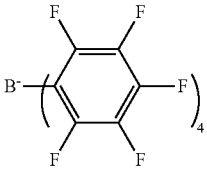 | 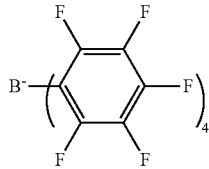 | 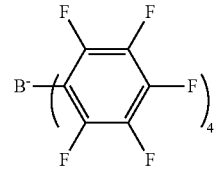 |
| R7' | —OH | —F | —F | —F |
| R8 | —$CH_3$ | —$CH_3$ | —$CH_3$ | —$CH_3$ |
| R9 | 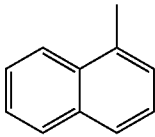 | 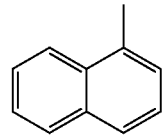 | 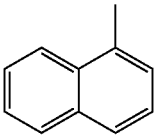 | 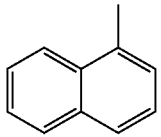 |
| Mass ratio | 55.0 | 98.4 | 90.0 | 55.0 |
| Cold curing properties | A | A | A | A |
| Amount of curing agent | A | B | A | A |
| Storage stability | B | A | A | B |

TABLE 6

| Segment | Example 36 | Example 37 | Example 38 |
|---|---|---|---|
| R10 | $B^-\!\!-\!\!(\text{C}_6\text{H}_4\text{-F})_4$ (para-F phenyl) | $B^-\!\!-\!\!(\text{2,4-difluorophenyl})_4$ | $B^-\!\!-\!\!(\text{2,6-difluoro-4-F phenyl})_4$ |
| R7' | —O—CH$_3$ | —O—CH$_3$ | —O—CH$_3$ |
| R8 | —CH$_3$ | —CH$_3$ | —CH$_3$ |
| R9 | 1-methylnaphthalenyl | 1-methylnaphthalenyl | 1-methylnaphthalenyl |
| Mass ratio | 93.0 | 94.0 | 93.5 |
| Cold curing properties | B | B | B |
| Amount of curing agent | B | B | B |
| Storage stability | B | B | B |

TABLE 7

| Segment | Reference Example A | Example 39 |
|---|---|---|
| R10 | $B^-\!\!-\!\!(\text{C}_6\text{F}_5)_4$ | $B^-\!\!-\!\!(\text{C}_6\text{F}_5)_4$ |
| R7' | —O—CH$_3$ | —O—CH$_3$ |
| R8 | —CH$_3$ | —CH$_3$ |
| R9 | 1-methylnaphthalenyl | 1-methylnaphthalenyl |
| Mass ratio | 100.0 | 10.0 |
| Cold curing properties | B | B |
| Amount of curing agent | B | B |
| Storage stability | B | B |

TABLE 8

| Segment | Reference Example 1 | Reference Example 2 |
|---|---|---|
| R10 | $B^-\!\!-\!\!(\text{C}_6\text{F}_5)_4$ | $B^-\!\!-\!\!(\text{C}_6\text{F}_5)_4$ |
| R7' | —O—CH$_3$ | —OH |
| R8 | —CH$_3$ | —CH$_3$ |
| R9 | 1-methylnaphthalenyl | 1-methylnaphthalenyl |
| Mass ratio | 99.7 | 45.0 |
| Cold curing properties | C | A |
| Amount of curing agent | D | C |
| Storage stability | A | D |

Production Example 1

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.80 parts by mass of thermal cationic polymerization initiator 1. The ratio of the mass of the compound B to the total mass of the compound B and the compound A was 0.970. The yield with respect to 4-methoxythioanisole was 80.0%. The mass of the compound B was 7.57 g, and the mass of the compound A was 0.23 g.

Production Example 2

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of thermal cationic polymerization initiator 2. The ratio of the mass of the compound B to the total mass of the compound B and the compound A was 0.972. The yield with respect to 4-methylthiophenol was 82%. The mass of the compound B was 7.66 g, and the mass of the compound A was 0.22 g.

Production Example 3

1.25 parts by mass of 4-methylthiotoluene, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.17 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.08 parts by mass of thermal cationic polymerization initiator 3. The ratio of the mass of the compound B to the total mass of the compound B and the compound A was 0.971. The yield with respect to 4-methylthiotoluene was 75%. The mass of the compound B was 6.87 g, and the mass of the compound A was 0.21 g.

Production Example 4

1.53 parts by mass of 4-methylthioacetophenone, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.42 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.49 parts by mass of thermal cationic polymerization initiator 4. The ratio of the mass of the compound B to the total mass of the compound B and the compound A was 0.969. The yield with respect to 4-methylthioacetophenone was 77%. The mass of the compound B was 7.26 g, and the mass of the compound A was 0.23 g.

Production Example 5

1.69 parts by mass of 4-acetoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.57 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.81 parts by mass of thermal cationic polymerization initiator 5. The ratio of the mass of the compound B to the total mass of the compound B and the compound A was 0.967. The yield with respect to 4-acetoxythioanisole was 79%. The mass of the compound B was 7.55 g, and the mass of the compound A was 0.26 g.

Production Example 6

1.99 parts by mass of 4-methyl carbonate thioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.84 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.64 parts by mass of thermal cationic polymerization initiator 6. The ratio of the mass of the compound B to the total mass of the compound B and the compound A was 0.974. The yield with respect to 4-methyl carbonate thioanisole was 75%. The mass of the compound B was 7.44 g, and the mass of the compound A was 0.20 g.

Production Example 7

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.70 parts by mass of thermal cationic polymerization initiator 7. The ratio of the mass of the compound B to the total mass of the compound B and the compound A was 0.962. The yield with respect to 4-fluorothioanisole was 80%. The mass of the compound B was 7.41 g, and the mass of the compound A was 0.29 g.

Production Example 8

1.39 parts by mass of 4-methylthioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.30 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.09 parts by mass of thermal cationic polymerization initiator 8. The ratio of the mass of the compound B to the total mass of the compound B and the compound A was 0.973. The yield with respect to 4-methylthioanisole was 74%. The mass of the compound B was 6.90 g, and the mass of the compound A was 0.19 g.

Production Example 9

1.55 parts by mass of 4-methoxythioanisole, 1.95 parts by mass of silver borofluoride, 1.41 parts by mass of α-chloro-o-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.41 parts by mass of thermal cationic polymerization initiator 9. The ratio of the mass of the compound B to the total mass of the compound B and the compound A was 0.974. The yield with respect to 4-methoxythioanisole was 79%. The mass of the compound B was 7.22 g, and the mass of the compound A was 0.19 g.

Production Example 10

1.55 parts by mass of 4-methoxythioanisole, 1.95 parts by mass of silver borofluoride, 1.41 parts by mass of α-chloro-p-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.60 parts by mass of thermal cationic polymerization initiator 10. The ratio of the mass of the compound B to the total mass of the compound B and the compound A was 0.962. The yield with respect to 4-methoxythioanisole was 81%. The mass of the compound B was 7.31 g, and the mass of the compound A was 0.29 g.

Production Example 11

1.55 parts by mass of 4-methoxythioanisole, 1.95 parts by mass of silver borofluoride, 1.41 parts by mass of α-chloro-m-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.50 parts by mass of thermal cationic polymerization initiator 11. The ratio of the mass of the compound B to the total mass of the compound B and the compound A was 0.968. The yield with respect to 4-methoxythioanisole was 80%. The mass of the compound B was 7.26 g, and the mass of the compound A was 0.24 g.

Production Example 12

1.55 parts by mass of 4-methoxythioanisole, 1.95 parts by mass of silver borofluoride, 0.91 parts by mass of 1-chloro-2-butene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 2.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.66 parts by mass of thermal cationic polymerization initiator 12. The ratio of the mass of the compound B to the total mass of the compound B and the compound A was 0.972. The yield with respect to 4-methoxythioanisole was 75%. The mass of the compound B was 6.47 g, and the mass of the compound A was 0.19 g.

Production Example 13

1.55 parts by mass of 4-methoxythioanisole, 1.95 parts by mass of silver borofluoride, 2.26 parts by mass of 9-chloromethylanthracene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 4.32 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.50 parts by mass of thermal cationic polymerization initiator 13. The ratio of the mass of the compound B to the total mass of the compound B and the compound A was 0.968. The yield with respect to 4-methoxythioanisole was 83%. The mass of the compound B was 8.23 g, and the mass of the compound A was 0.27 g.

Production Example 14

1.55 parts by mass of 4-methoxythioanisole, 1.95 parts by mass of silver borofluoride, 2.03 parts by mass of 4-(chloromethyl)biphenyl, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the product was washed. The solvent was distilled off under reduced pressure from the organic layer to obtain 8.10 parts by mass of thermal cationic polymerization initiator 14. The ratio of the mass of the compound B to the total mass of the compound B and the compound A was 0.974. The yield with respect to 4-methoxythioanisole was 81%. The mass of the compound B was 7.89 g, and the mass of the compound A was 0.21 g.

Production Example 15

1.55 parts by mass of 4-methoxythioanisole, 1.95 parts by mass of silver borofluoride, 1.77 parts by mass of 2-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.31 parts by mass of thermal cationic polymerization initiator 15. The ratio of the mass of the compound B to the total mass of the compound B and the compound A was 0.968. The yield with respect to 4-methoxythioanisole was 75%.

Production Example 16

1.55 parts by mass of 4-methoxythioanisole, 1.95 parts by mass of silver borofluoride, 1.57 parts by mass of p-methoxybenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.06 parts by mass of thermal cationic polymerization initiator 16. The ratio of the mass of the compound B to the total mass of the compound B and the compound A was 0.965. The yield with respect to 4-methoxythioanisole was 74%. The mass of the compound B was 6.81 g, and the mass of the compound A was 0.25 g.

Production Example 17

1.55 parts by mass of 4-methoxythioanisole, 1.95 parts by mass of silver borofluoride, 1.56 parts by mass of p-chlorobenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.13 parts by mass of thermal cationic polymerization initiator 17. The ratio of the mass of the compound B to the total mass of the compound B and the compound A was 0.934. The yield with respect to 4-methoxythioanisole was 64%. The mass of the compound B was 5.73 g, and the mass of the compound A was 0.40 g.

Production Example 18

1.55 parts by mass of 4-methoxythioanisole, 1.95 parts by mass of silver borofluoride, 1.60 parts by mass of 2,6-dichlorobenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.24 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.95 parts by mass of thermal cationic polymerization initiator 18. The ratio of the mass of the compound B to the total mass of the compound B and the compound A was 0.921. The yield with respect to 4-methoxythioanisole was 70%. The mass of the compound B was 6.40 g, and the mass of the compound A was 0.55 g.

Production Example 19

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane. 6.82 parts by mass of thermal cationic polymerization initiator 19 were obtained. The ratio of the mass of the compound B to the total mass of the compound B and the compound A was 0.984. The yield with respect to 4-methoxythioanisole was 70.0%. The mass of the compound B was 6.72 g, and the mass of the compound A was 0.10 g.

Production Example 20

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.99 parts by mass of thermal cationic polymerization initiator 20. The ratio of the mass of the compound B to the total mass of the compound B and the compound A was 0.900. The yield with respect to 4-methoxythioanisole was 82%. The mass of the compound B was 7.19 g, and the mass of the compound A was 0.80 g.

Production Example 21

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.28 parts by mass of thermal cationic polymerization initiator 21. The ratio of the mass of the compound B to the total mass of the compound B and the compound A was 0.550. The yield with respect to 4-methoxythioanisole was 85%. The mass of the compound B was 4.55 g, and the mass of the compound A was 3.73 g.

Production Example 22

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.72 parts by mass of thermal cationic polymerization initiator 22. The ratio of the mass of the compound B to the total mass of the compound B and the compound A was 0.984. The yield with respect to 4-methylthiophenol was 70%. The mass of the compound B was 6.62 g, and the mass of the compound A was 0.10 g.

Production Example 23

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of thermal cationic polymerization initiator 23. The ratio of the mass of the compound B to the total mass of the compound B and the compound A was 0.900. The yield with respect to 4-methylthiophenol was 82%. The mass of the compound B was 7.09 g, and the mass of the compound A was 0.79 g.

Production Example 24

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.16 parts by mass of thermal cationic polymerization initiator 24. The ratio of the mass of the compound B to the total mass of the compound B and the compound A was 0.550. The yield with respect to 4-methylthiophenol was 85%. The mass of the compound B was 4.49 g, and the mass of the compound A was 3.67 g.

Production Example 25

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.74 parts by mass of thermal cationic polymerization initiator 25. The ratio of the mass of the compound B to the total mass of the compound B and the compound A was 0.984. The yield with respect to 4-fluorothioanisole was 70%. The mass of the compound B was 6.64 g, and the mass of the compound A was 0.10 g.

Production Example 26

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.89 parts by mass of thermal cationic polymerization initiator 26. The ratio of the mass of the compound B to the total mass of the compound B and the compound A was 0.900. The yield with respect to 4-fluorothioanisole was 82%. The mass of the compound B was 7.10 g, and the mass of the compound A was 0.79 g.

Production Example 27

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.18 parts by mass of thermal cationic polymerization initiator 27. The ratio of the mass of the compound B to the total mass of the compound B and the compound A was 0.550. The yield with respect to 4-fluorothioanisole was 85%. The mass of the compound B was 4.50 g, and the mass of the compound A was 3.68 g.

Production Example 28

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether to obtain 3.90 parts by mass of thermal cationic polymerization initiator 28. The ratio of the mass of the compound B to the total mass of the compound B and the compound A was 0.997. The yield with respect to 4-methoxythioanisole was 10.0%. The mass of the compound B was 0.38883 g. The mass of the compound A was 0.00117 g.

Production Example 29

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.78 parts by mass of thermal cationic polymerization initiator 29. The ratio of the mass of the compound B to the total mass of the compound B and the compound A was 0.440. The yield with respect to 4-methoxythioanisole was 90.1%. The mass of the compound B was 3.86 g. The mass of the compound A was 4.92 g.

Production Example 30

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether to obtain 1.15 parts by mass of thermal cationic polymerization initiator 30. The ratio of the mass of the compound B to the total mass of the compound B and the compound A was 0.998. The yield with respect to 4-methylthiophenol was 12%. The mass of the compound B was 1.1477 g, and the mass of the compound A was 0.0023 g.

Production Example 31

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.65 parts by mass of thermal cationic polymerization initiator 31. The ratio of the mass of the compound B to the total mass of the compound B and the compound A was 0.450. The yield with respect to 4-methylthiophenol was 90%. The mass of the compound B was 3.89 g. The mass of the compound A was 4.76 g.

Tables 9 to 12 show the structure of the compound B in the thermal cationic polymerization initiators of Production Examples 1 to 31 thus obtained, and the mass ratio of the compound B to the compounds A and B.

TABLE 9

| Segment | Production Example 1 | Production Example 2 | Production Example 3 | Production Example 4 |
|---|---|---|---|---|
| R10 | 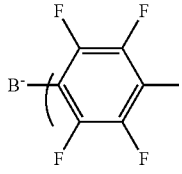 | 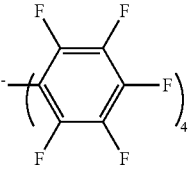 | 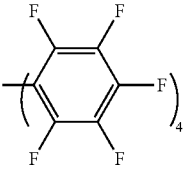 | 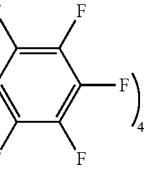 |
| R7' | —O—CH$_3$ | —OH | —H |  |
| R8 | —CH$_3$ | —CH$_3$ | —CH$_3$ | —CH$_3$ |
| R9 | 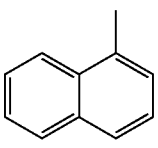 | 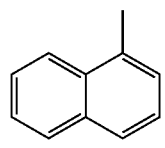 | 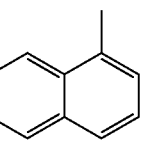 | 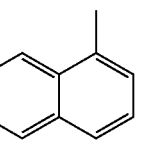 |
| Mass ratio | 97.0 | 97.2 | 97.1 | 96.9 |

| Segment | Production Example 5 | Production Example 6 | Production Example 7 | Production Example 8 |
|---|---|---|---|---|
| R10 | 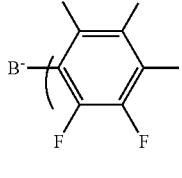 | 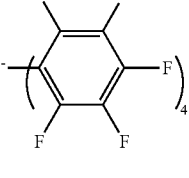 | 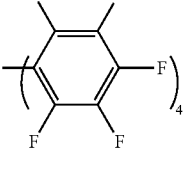 | 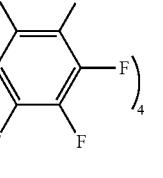 |
| R7' | 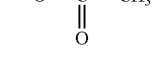 | 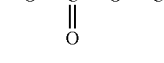 | —F | —CH$_3$ |
| R8 | —CH$_3$ | —CH$_3$ | —CH$_3$ | —CH$_3$ |

TABLE 9-continued

| Segment | | | | |
|---|---|---|---|---|
| R9 | 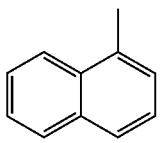 | 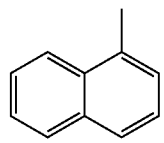 | 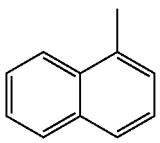 | 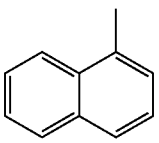 |
| Mass ratio | 96.7 | 97.4 | 96.2 | 97.3 |

TABLE 10

| Segment | Production Example 9 | Production Example 10 | Production Example 11 | Production Example 12 | Production Example 13 |
|---|---|---|---|---|---|
| R10 | 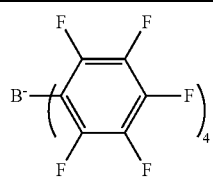 | 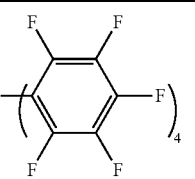 | 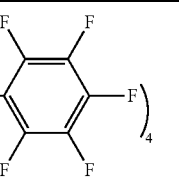 | 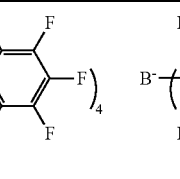 | 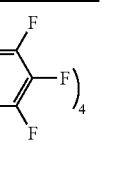 |
| R7' | —O—CH$_3$ | —O—CH$_3$ | —O—CH$_3$ | —O—CH$_3$ | —O—CH$_3$ |
| R8 | —CH$_3$ | —CH$_3$ | —CH$_3$ | —CH$_3$ | —CH$_3$ |
| R9 | 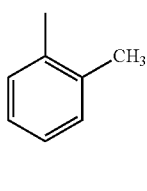 | 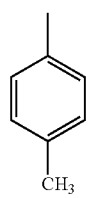 | 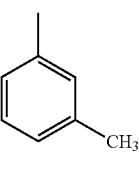 |  | 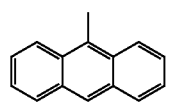 |
| Mass ratio | 97.4 | 96.2 | 96.8 | 97.2 | 96.8 |

| Segment | Production Example 14 | Production Example 15 | Production Example 16 | Production Example 17 | Production Example 18 |
|---|---|---|---|---|---|
| R10 | 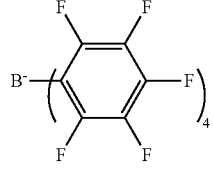 | 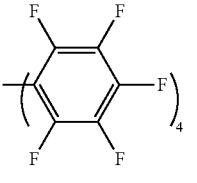 | 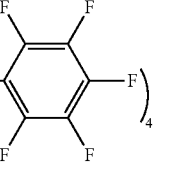 | 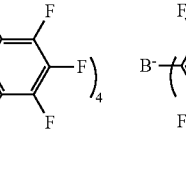 | 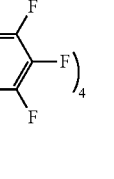 |
| R7' | —O—CH$_3$ | —O—CH$_3$ | —O—CH$_3$ | —O—CH$_3$ | —O—CH$_3$ |
| R8 | —CH$_3$ | —CH$_3$ | —CH$_3$ | —CH$_3$ | —CH$_3$ |
| R9 | 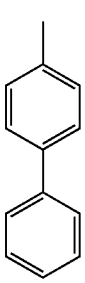 | 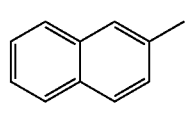 | 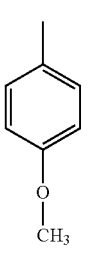 | 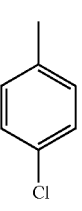 | 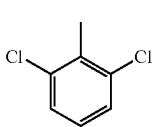 |
| Mass ratio | 97.4 | 96.8 | 96.5 | 93.4 | 92.1 |

TABLE 11

| Segment | Production Example 19 | Production Example 20 | Production Example 21 | Production Example 22 | Production Example 23 |
|---|---|---|---|---|---|
| R10 | $B^-(C_6F_5)_4$ | $B^-(C_6F_5)_4$ | $B^-(C_6F_5)_4$ | $B^-(C_6F_5)_4$ | $B^-(C_6F_5)_4$ |
| R7' | —O—CH$_3$ | —O—CH$_3$ | —O—CH$_3$ | —OH | —OH |
| R8 | —CH$_3$ | —CH$_3$ | —CH$_3$ | —CH$_3$ | —CH$_3$ |
| R9 | 1-naphthyl | 1-naphthyl | 1-naphthyl | 1-naphthyl | 1-naphthyl |
| Mass ratio | 98.4 | 90.0 | 55.0 | 98.4 | 90.0 |

| Segment | Production Example 24 | Production Example 25 | Production Example 26 | Production Example 27 |
|---|---|---|---|---|
| R10 | $B^-(C_6F_5)_4$ | $B^-(C_6F_5)_4$ | $B^-(C_6F_5)_4$ | $B^-(C_6F_5)_4$ |
| R7' | —OH | —F | —F | —F |
| R8 | —CH$_3$ | —CH$_3$ | —CH$_3$ | —CH$_3$ |
| R9 | 1-naphthyl | 1-naphthyl | 1-naphthyl | 1-naphthyl |
| Mass ratio | 55.0 | 98.4 | 90.0 | 55.0 |

TABLE 12

| Segment | Production Example 28 | Production Example 29 | Production Example 30 | Production Example 31 |
|---|---|---|---|---|
| R10 | $B^-(C_6F_5)_4$ | $B^-(C_6F_5)_4$ | $B^-(C_6F_5)_4$ | $B^-(C_6F_5)_4$ |
| R7' | —O—CH$_3$ | —O—CH$_3$ | —OH | —OH |
| R8 | —CH$_3$ | —CH$_3$ | —CH$_3$ | —CH$_3$ |

TABLE 12-continued

| Segment | Production Example 28 | Production Example 29 | Production Example 30 | Production Example 31 |
|---|---|---|---|---|
| R9 |  | 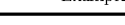 |  |  |
| Mass ratio | 99.7 | 44.0 | 99.8 | 45.0 |

Examples 40 to 66, Reference Examples 3 to 6, and Comparative Example 1

The thermal cationic polymerization initiator of each example, a liquid epoxy resin (EP828, manufactured by Mitsubishi Chemical Corp.), a silane coupling agent (KBE403, manufactured by Shin-Etsu Chemical Co., Ltd.), and conductive particles (Ni/Au-plated resin particles (3.2 μm), manufactured by Shinihon Chemicals Corp.) were uniformly mixed at the mixing ratio shown in Tables 13 and 14 to obtain thermally cationically polymerizable compositions of Examples 40 to 66 and Reference Examples 3 to 6. As for Comparative Example 1, a thermally cationically polymerizable composition was obtained in the same way as in Reference Example 3 except that SI-60 (containing antimony hexafluoride) manufactured by Sanshin Chemical Industry Co., Ltd. was used as thermal cationic polymerization initiator 32.

[Preparation of Flip Chip-type Semiconductor Apparatus]

A 10 mm×10 mm×0.725 mm silicon chip with copper bumps was flip chip-packaged onto a 42.5 mm thick×42.5 mm×1.0 mm BT resin substrate such that the gap size was approximately 50 μm. Next, the thermally polymerizable compositions of Examples 1 to 27 and Comparative Examples 1 to 5 were each allowed to be interposed between the chip and the substrate on a hot plate of 110° C., and then cured under conditions involving 120° C. for 0.5 hours and then 165° C. for 3 hours to prepare a flip chip-type semiconductor apparatus for testing. Each obtained semiconductor apparatus for testing was subjected to cold curing property evaluation, storage stability evaluation, moisture resistance test, and thermal shock test by methods given below. The results are shown in Tables 13 and 14.

[Each Performance Evaluation]

(1) Cold Curing Properties

The gel time was measured for the evaluation of cold curing properties. 1.0 part by mass of the compound produced in each example was uniformly mixed with 100 parts by mass of AER 2603 (manufactured by Asahi Kasei E-materials Corp.). The sample for evaluation was added dropwise at a size of approximately 5 mmϕ onto a hot plate of 100±2° C. The time required for the sample to become no longer stringy was measured using a stopwatch. Specifically, a sample rated as "A" or "B" was determined to have cold curing properties.

A: shorter than 180 seconds
B: 180 seconds or longer and shorter than 300 seconds
C: 300 seconds or longer (2) Storage Stability 1.0 part by mass of the thermal cationic polymerization initiator produced in each example was uniformly mixed with 100 parts by mass of AER 2603 (manufactured by Asahi Kasei E-materials Corp.). The prepared composition was stored at 30° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as "A" or "B" was determined to have adequate storage stability.

A: less than 2-fold increase in the viscosity after storage
B: 2-fold or more and less than 5-fold increase in the viscosity after storage
C: 5-fold or more and less than 10-fold increase in the viscosity after storage (3) Moisture Resistance Test The semiconductor apparatus for testing obtained by the aforementioned method was placed at 130° C. and 2.1 atm for 1008 hours in an 85% humidity environment in a pressure cooker and then examined for the presence or absence of conduction by the current test to determine the rate of failure (%).

(4) Thermal Shock Resistance Test

The semiconductor apparatus for testing obtained by the aforementioned method was placed for 192 hours under conditions involving 30° C. and 65% RH and passed 5 times through an IR reflow oven set to the maximum temperature 265° C. Then, cracks were examined after 1000 cycles each involving −55° C. for 10 minutes and 125° C. for 10 minutes to determine the proportion of chips observed to have cracks (%).

TABLE 13

| Segment | Ex. 40 | Ex. 41 | Ex. 42 | Ex. 43 | Ex. 44 | Ex. 45 | Ex. 46 | Ex. 47 | Ex. 48 | Ex. 49 | Ex. 50 | Ex. 51 | Ex. 52 | Ex. 53 | Ex. 54 | Ex. 55 | Ex. 56 |
|---|---|---|---|---|---|---|---|---|---|---|---|---|---|---|---|---|---|
| Thermal cationic polymerization initiator 1 | 3 | | | | | | | | | | | | | | | | |
| Thermal cationic polymerization initiator 2 | | 3 | | | | | | | | | | | | | | | |

TABLE 13-continued

| Segment | Ex. 40 | Ex. 41 | Ex. 42 | Ex. 43 | Ex. 44 | Ex. 45 | Ex. 46 | Ex. 47 | Ex. 48 | Ex. 49 | Ex. 50 | Ex. 51 | Ex. 52 | Ex. 53 | Ex. 54 | Ex. 55 | Ex. 56 |
|---|---|---|---|---|---|---|---|---|---|---|---|---|---|---|---|---|---|
| Thermal cationic polymerization initiator 3 | | 3 | | | | | | | | | | | | | | | |
| Thermal cationic polymerization initiator 4 | | | 3 | | | | | | | | | | | | | | |
| Thermal cationic polymerization initiator 5 | | | | 3 | | | | | | | | | | | | | |
| Thermal cationic polymerization initiator 6 | | | | | 3 | | | | | | | | | | | | |
| Thermal cationic polymerization initiator 7 | | | | | | 3 | | | | | | | | | | | |
| Thermal cationic polymerization initiator 8 | | | | | | | 3 | | | | | | | | | | |
| Thermal cationic polymerization initiator 9 | | | | | | | | 3 | | | | | | | | | |
| Thermal cationic polymerization initiator 10 | | | | | | | | | 3 | | | | | | | | |
| Thermal cationic polymerization initiator 11 | | | | | | | | | | 3 | | | | | | | |
| Thermal cationic polymerization initiator 12 | | | | | | | | | | | 3 | | | | | | |
| Thermal cationic polymerization initiator 13 | | | | | | | | | | | | 3 | | | | | |
| Thermal cationic polymerization initiator 14 | | | | | | | | | | | | | 3 | | | | |
| Thermal cationic polymerization initiator 15 | | | | | | | | | | | | | | 3 | | | |
| Thermal cationic polymerization initiator 16 | | | | | | | | | | | | | | | 3 | | |
| Thermal cationic polymerization initiator 17 | | | | | | | | | | | | | | | | | 3 |
| Thermal cationic polymerization initiator 18 | | | | | | | | | | | | | | | | | |
| Thermal cationic polymerization initiator 19 | | | | | | | | | | | | | | | | | |
| Thermal cationic polymerization initiator 20 | | | | | | | | | | | | | | | | | |
| Thermal cationic polymerization initiator 21 | | | | | | | | | | | | | | | | | |
| Thermal cationic polymerization initiator 22 | | | | | | | | | | | | | | | | | |
| Thermal cationic polymerization initiator 23 | | | | | | | | | | | | | | | | | |
| Thermal cationic polymerization initiator 24 | | | | | | | | | | | | | | | | | |
| Thermal cationic polymerization initiator 25 | | | | | | | | | | | | | | | | | |
| Thermal cationic polymerization initiator 26 | | | | | | | | | | | | | | | | | |
| Thermal cationic polymerization initiator 27 | | | | | | | | | | | | | | | | | |

TABLE 13-continued

| Segment | Ex. 40 | Ex. 41 | Ex. 42 | Ex. 43 | Ex. 44 | Ex. 45 | Ex. 46 | Ex. 47 | Ex. 48 | Ex. 49 | Ex. 50 | Ex. 51 | Ex. 52 | Ex. 53 | Ex. 54 | Ex. 55 | Ex. 56 |
|---|---|---|---|---|---|---|---|---|---|---|---|---|---|---|---|---|---|
| Thermal cationic polymerization initiator 28 | | | | | | | | | | | | | | | | | |
| Thermal cationic polymerization initiator 29 | | | | | | | | | | | | | | | | | |
| Thermal cationic polymerization initiator 30 | | | | | | | | | | | | | | | | | |
| Thermal cationic polymerization initiator 31 | | | | | | | | | | | | | | | | | |
| Thermal cationic polymerization initiator SI-60 (manufactured by Sanshin Chemical Industry Co., Ltd.) | | | | | | | | | | | | | | | | | |
| Liquid epoxy resin (AER 2603, Asahi Kasei E-materials Corp.) | 40 | 40 | 40 | 40 | 40 | 40 | 40 | 40 | 40 | 40 | 40 | 40 | 40 | 40 | 40 | 40 | 40 |
| Highly pure synthetic spherical silica (SO-C1, Admatechs Co., Ltd.) | 120 | 120 | 120 | 120 | 120 | 120 | 120 | 120 | 120 | 120 | 120 | 120 | 120 | 120 | 120 | 120 | 120 |
| Cold curing properties | A | A | A | A | A | A | A | A | A | A | A | A | A | A | A | A | A |
| Storage stability | A | A | A | A | B | B | B | A | A | A | A | A | A | A | A | A | A |
| Thermal shock resistance, rate of failure (%) | 0 | 0 | 0 | 0 | 0 | 0 | 0 | 0 | 0 | 0 | 0 | 0 | 0 | 0 | 0 | 0 | 0 |
| Moisture resistance, rate of failure (%) | 0 | 0 | 0 | 0 | 0 | 0 | 0 | 0 | 0 | 0 | 0 | 0 | 0 | 0 | 0 | 0 | 0 |

TABLE 14

| Segment | Ex. 57 | Ex. 58 | Ex. 59 | Ex. 60 | Ex. 61 | Ex. 62 | Ex. 63 | Ex. 64 | Ex. 65 | Ex. 66 | Reference Example 3 | Reference Example 4 | Reference Example 5 | Reference Example 6 | Comp. Ex. 1 |
|---|---|---|---|---|---|---|---|---|---|---|---|---|---|---|---|
| Thermal cationic polymerization initiator 1 | | | | | | | | | | | | | | | |
| Thermal cationic polymerization initiator 2 | | | | | | | | | | | | | | | |
| Thermal cationic polymerization initiator 3 | | | | | | | | | | | | | | | |
| Thermal cationic polymerization initiator 4 | | | | | | | | | | | | | | | |
| Thermal cationic polymerization initiator 5 | | | | | | | | | | | | | | | |
| Thermal cationic polymerization initiator 6 | | | | | | | | | | | | | | | |
| Thermal cationic polymerization initiator 7 | | | | | | | | | | | | | | | |
| Thermal cationic polymerization initiator 8 | | | | | | | | | | | | | | | |
| Thermal cationic polymerization initiator 9 | | | | | | | | | | | | | | | |
| Thermal cationic polymerization initiator 10 | | | | | | | | | | | | | | | |

TABLE 14-continued

| Segment | Ex. 57 | Ex. 58 | Ex. 59 | Ex. 60 | Ex. 61 | Ex. 62 | Ex. 63 | Ex. 64 | Ex. 65 | Ex. 66 | Reference Example 3 | Reference Example 4 | Reference Example 5 | Reference Example 6 | Comp. Ex. 1 |
|---|---|---|---|---|---|---|---|---|---|---|---|---|---|---|---|
| Thermal cationic polymerization initiator 11 | | | | | | | | | | | | | | | |
| Thermal cationic polymerization initiator 12 | | | | | | | | | | | | | | | |
| Thermal cationic polymerization initiator 13 | | | | | | | | | | | | | | | |
| Thermal cationic polymerization initiator 14 | | | | | | | | | | | | | | | |
| Thermal cationic polymerization initiator 15 | | | | | | | | | | | | | | | |
| Thermal cationic polymerization initiator 16 | | | | | | | | | | | | | | | |
| Thermal cationic polymerization initiator 17 | | | | | | | | | | | | | | | |
| Thermal cationic polymerization initiator 18 | 3 | | | | | | | | | | | | | | |
| Thermal cationic polymerization initiator 19 | | 3 | | | | | | | | | | | | | |
| Thermal cationic polymerization initiator 20 | | | 3 | | | | | | | | | | | | |
| Thermal cationic polymerization initiator 21 | | | | 3 | | | | | | | | | | | |
| Thermal cationic polymerization initiator 22 | | | | | 3 | | | | | | | | | | |
| Thermal cationic polymerization initiator 23 | | | | | | 3 | | | | | | | | | |
| Thermal cationic polymerization initiator 24 | | | | | | | 3 | | | | | | | | |
| Thermal cationic polymerization initiator 25 | | | | | | | | 3 | | | | | | | |
| Thermal cationic polymerization initiator 26 | | | | | | | | | 3 | | | | | | |
| Thermal cationic polymerization initiator 27 | | | | | | | | | | 3 | | | | | |
| Thermal cationic polymerization initiator 28 | | | | | | | | | | | 3 | | | | |
| Thermal cationic polymerization initiator 29 | | | | | | | | | | | | 3 | | | |
| Thermal cationic polymerization initiator 30 | | | | | | | | | | | | | 3 | | |
| Thermal cationic polymerization initiator 31 | | | | | | | | | | | | | | 3 | |
| Thermal cationic polymerization initiator SI-60 (manufactured by Sanshin Chemical Industry Co., Ltd.) | | | | | | | | | | | | | | | 3 |
| Liquid epoxy resin (AER 2603, Asahi Kasei E-materials Corp.) | 40 | 40 | 40 | 40 | 40 | 40 | 40 | 40 | 40 | 40 | 40 | 40 | 40 | 40 | 40 |

TABLE 14-continued

| Segment | Ex. 57 | Ex. 58 | Ex. 59 | Ex. 60 | Ex. 61 | Ex. 62 | Ex. 63 | Ex. 64 | Ex. 65 | Ex. 66 | Reference Example 3 | Reference Example 4 | Reference Example 5 | Reference Example 6 | Comp. Ex. 1 |
|---|---|---|---|---|---|---|---|---|---|---|---|---|---|---|---|
| Highly pure synthetic spherical silica (SO-C1, Admatechs Co., Ltd.) | 120 | 120 | 120 | 120 | 120 | 120 | 120 | 120 | 120 | 120 | 120 | 120 | 120 | 120 | 120 |
| Cold curing properties | A | A | A | A | A | A | A | A | A | A | B | A | B | A | C |
| Storage stability | A | A | A | A | A | A | A | A | A | A | A | C | A | C | B |
| Thermal shock resistance, rate of failure (%) | 0 | 0 | 0 | 0 | 0 | 0 | 0 | 0 | 0 | 0 | 10 | 20 | 15 | 20 | 25 |
| Moisture resistance, rate of failure (%) | 0 | 0 | 0 | 0 | 0 | 0 | 0 | 0 | 0 | 0 | 15 | 25 | 20 | 25 | 25 |

Production Example 32

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.80 parts by mass of thermal cationic polymerization initiator 2-1. The ratio of the mass of the compound B to the total mass of the compound B and the compound A was 0.970. The yield with respect to 4-methoxythioanisole was 80.0%. The mass of the compound B was 7.57 g, and the mass of the compound A was 0.23 g.

Production Example 33

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of thermal cationic polymerization initiator 2-2. The ratio of the mass of the compound B to the total mass of the compound B and the compound A was 0.972. The yield with respect to 4-methylthiophenol was 82%. The mass of the compound B was 7.66 g, and the mass of the compound A was 0.22 g.

Production Example 34

1.25 parts by mass of 4-methylthiotoluene, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.17 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.08 parts by mass of thermal cationic polymerization initiator 2-3. The ratio of the mass of the compound B to the total mass of the compound B and the compound A was 0.971. The yield with respect to 4-methylthiotoluene was 75%. The mass of the compound B was 6.87 g, and the mass of the compound A was 0.21 g.

Production Example 35

1.53 parts by mass of 4-methylthioacetophenone, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.42 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.49 parts by mass of thermal cationic polymerization initiator 2-4. The ratio of the mass of the compound B to the total mass of the compound B and the compound A was 0.969. The yield with respect to 4-methylthioacetophenone was 77%. The mass of the compound B was 7.26 g, and the mass of the compound A was 0.23 g.

Production Example 36

1.69 parts by mass of 4-acetoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.57 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.81 parts by mass of thermal cationic polymerization initiator 2-5. The ratio of the mass of the compound B to the total mass of the compound B and the compound A was 0.967. The yield with respect to 4-acetoxythioanisole was 79%. The mass of the compound B was 7.55 g, and the mass of the compound A was 0.26 g.

Production Example 37

1.99 parts by mass of 4-methyl carbonate thioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.84 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.64 parts by mass of thermal cationic polymerization initiator 2-6. The ratio of the mass of the compound B to the total mass of the compound B and the compound A was 0.974. The yield with respect to 4-methyl carbonate thioanisole was 75%. The mass of the compound B was 7.44 g, and the mass of the compound A was 0.20 g.

Production Example 38

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.70 parts by mass of thermal cationic polymerization initiator 2-7. The ratio of the mass of the compound B to the total mass of the compound B and the compound A was 0.962. The yield with respect to 4-fluorothioanisole was 80%. The mass of the compound B was 7.41 g, and the mass of the compound A was 0.29 g.

Production Example 39

1.39 parts by mass of 4-methylthioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.30 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.09 parts by mass of thermal cationic polymerization initiator 2-8. The ratio of the mass of the compound B to the total mass of the compound B and the compound A was 0.973. The yield with respect to 4-methylthioanisole was 74%. The mass of the compound B was 6.90 g, and the mass of the compound A was 0.19 g.

Production Example 40

1.55 parts by mass of 4-methoxythioanisole, 1.95 parts by mass of silver borofluoride, 1.41 parts by mass of α-chloro-o-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.41 parts by mass of thermal cationic polymerization initiator 2-9. The ratio of the mass of the compound B to the total mass of the compound B and the compound A was 0.974. The yield with respect to 4-methoxythioanisole was 79%. The mass of the compound B was 7.22 g, and the mass of the compound A was 0.19 g.

Production Example 41

1.55 parts by mass of 4-methoxythioanisole, 1.95 parts by mass of silver borofluoride, 1.41 parts by mass of α-chloro-p-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.60 parts by mass of thermal cationic polymerization initiator 2-10. The ratio of the mass of the compound B to the total mass of the compound B and the compound A was 0.962. The yield with respect to 4-methoxythioanisole was 81%. The mass of the compound B was 7.31 g, and the mass of the compound A was 0.29 g.

Production Example 42

1.55 parts by mass of 4-methoxythioanisole, 1.95 parts by mass of silver borofluoride, 1.41 parts by mass of α-chloro-m-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.50 parts by mass of thermal cationic polymerization initiator 2-11. The ratio of the mass of the compound B to the total mass of the compound B and the compound A was 0.968. The yield with respect to 4-methoxythioanisole was 80%. The mass of the compound B was 7.26 g, and the mass of the compound A was 0.24 g.

Production Example 43

1.55 parts by mass of 4-methoxythioanisole, 1.95 parts by mass of silver borofluoride, 0.91 parts by mass of 1-chloro-2-butene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 2.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.66 parts by mass of thermal cationic polymerization initiator 2-12. The ratio of the mass of the compound B to the total mass of the compound B and the compound A was 0.972. The yield with respect to 4-methoxythioanisole was 75%. The mass of the compound B was 6.47 g, and the mass of the compound A was 0.19 g.

Production Example 44

1.55 parts by mass of 4-methoxythioanisole, 1.95 parts by mass of silver borofluoride, 2.26 parts by mass of 9-chloromethylanthracene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 4.32 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.50 parts by mass of thermal cationic polymerization initiator 2-13. The ratio of the mass of the compound B to the total mass of the compound B and the compound A was 0.968. The yield with respect to 4-methoxythioanisole was 83%. The mass of the compound B was 8.23 g, and the mass of the compound A was 0.27 g.

Production Example 45

1.55 parts by mass of 4-methoxythioanisole, 1.95 parts by mass of silver borofluoride, 2.03 parts by mass of 4-(chloromethyl) biphenyl, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.67 parts by mass of the obtained precipitate, 6.86 parts by mass of lithium tetrakis(pentafluorophenyl) borate, and 10.0 parts by mass of acetone were uniformly mixed and reacted at 25° C. for 24 hours. 10.0 parts by mass of distilled water were added to the reaction solution to wash the product. The solvent was distilled off under reduced pressure from the organic layer to wash the product. The solvent was distilled off under reduced pressure from the organic layer to obtain 8.10 parts by mass of thermal cationic polymerization initiator 2-14. The ratio of the mass of the compound B to the total mass of the compound B and the compound A was 0.974. The yield with respect to 4-methoxythioanisole was 81%. The mass of the compound B was 7.89 g, and the mass of the compound A was 0.21 g.

Production Example 46

1.55 parts by mass of 4-methoxythioanisole, 1.95 parts by mass of silver borofluoride, 1.77 parts by mass of 2-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.31 parts by mass of thermal cationic polymerization initiator 2-15. The ratio of the mass of the compound B to the total mass of the compound B and the compound A was 0.968. The yield with respect to 4-methoxythioanisole was 75%.

Production Example 47

1.55 parts by mass of 4-methoxythioanisole, 1.95 parts by mass of silver borofluoride, 1.57 parts by mass of p-methoxybenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.06 parts by mass of thermal cationic polymerization initiator 2-16. The ratio of the mass of the compound B to the total mass of the compound B and the compound A was 0.965. The yield with respect to 4-methoxythioanisole was 74%. The mass of the compound B was 6.81 g, and the mass of the compound A was 0.25 g.

Production Example 48

1.55 parts by mass of 4-methoxythioanisole, 1.95 parts by mass of silver borofluoride, 1.56 parts by mass of p-chlorobenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.13 parts by mass of thermal cationic polymerization initiator 2-17. The ratio of the mass of the compound B to the total mass of the compound B and the compound A was 0.934. The yield with respect to 4-methoxythioanisole was 64%. The mass of the compound B was 5.73 g, and the mass of the compound A was 0.40 g.

Production Example 49

1.55 parts by mass of 4-methoxythioanisole, 1.95 parts by mass of silver borofluoride, 1.60 parts by mass of 2,6-dichlorobenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.24 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 6.95 parts by mass of thermal cationic polymerization initiator 2-18. The ratio of the mass of the compound B to the total mass of the compound B and the compound A was 0.921. The yield with respect to 4-methoxythioanisole was 70%. The mass of the compound B was 6.40 g, and the mass of the compound A was 0.55 g.

Production Example 50

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.82 parts by mass of thermal cationic polymerization initiator 2-19. The ratio of the mass of the compound B to the total mass of the compound B and the compound A was 0.984. The yield with respect to 4-methoxythioanisole was 70.0%. The mass of the compound B was 6.72 g, and the mass of the compound A was 0.10 g.

Production Example 51

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.99 parts by mass of thermal cationic polymerization initiator 2-20. The ratio of the mass of the compound B to the total mass of the compound B and the compound A was 0.900. The yield with respect to 4-methoxythioanisole was 82%. The mass of the compound B was 7.19 g, and the mass of the compound A was 0.80 g.

Production Example 52

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.28 parts by mass of thermal cationic polymerization initiator 2-21. The ratio of the mass of the compound B to the total mass of the compound B and the compound A was 0.550. The yield with respect to 4-methoxythioanisole was 85%. The mass of the compound B was 4.55 g, and the mass of the compound A was 3.73 g.

Production Example 53

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.72 parts by mass of thermal cationic polymerization initiator 2-22. The ratio of the mass of the compound B to the total mass of the compound B and the compound A was 0.984. The yield with respect to 4-methylthiophenol was 70%. The mass of the compound B was 6.62 g, and the mass of the compound A was 0.10 g.

Production Example 54

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 35° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of thermal cationic polymerization initiator 2-23. The ratio of the mass of the compound B to the total mass of the compound B and the compound A was 0.900. The yield with respect to 4-methylthiophenol was 82%. The mass of the compound B was 7.09 g, and the mass of the compound A was 0.79 g.

Production Example 55

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.16 parts by mass of thermal cationic polymerization initiator 2-24. The ratio of the mass of the compound B to the total mass of the compound B and the compound A was 0.550. The yield with respect to 4-methylthiophenol was 85%. The mass of the compound B was 4.49 g, and the mass of the compound A was 3.67 g.

Production Example 56

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from 10.0 parts by mass of diethyl ether and 10.0 parts by mass of hexane to obtain 6.74 parts by mass of thermal cationic polymerization initiator 2-25. The ratio of the mass of the compound B to the total mass of the compound B and the compound A was 0.984. The yield with respect to 4-fluorothioanisole was 70%. The mass of the compound B was 6.64 g, and the mass of the compound A was 0.10 g.

Production Example 57

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.89 parts by mass of thermal cationic polymerization initiator 2-26. The ratio of the mass of the compound B to the total mass of the compound B and the compound A was 0.900. The yield with respect to 4-fluorothioanisole was 82%. The mass of the compound B was 7.10 g, and the mass of the compound A was 0.79 g.

Production Example 58

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.18 parts by mass of thermal cationic polymerization initiator 2-27. The ratio of the mass of the compound B to the total mass of the compound B and the compound A was 0.550. The yield with respect to 4-fluorothioanisole was 85%. The mass of the compound B was 4.50 g, and the mass of the compound A was 3.68 g.

Production Example 59

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether to obtain 3.90 parts by mass of thermal cationic polymerization initiator 2-28. The ratio of the mass of the compound B to the total mass of the compound B and the compound A was 0.997. The yield with respect to 4-methoxythioanisole was 10.0%. The mass of the compound B was 0.38883 g. The mass of the compound A was 0.00117 g.

Production Example 60

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.78 parts by mass of thermal cationic polymerization initiator 2-29. The ratio of the mass of the compound B to the total mass of the compound B and the compound A was 0.440. The yield with respect to 4-methoxythioanisole was 90.1%. The mass of the compound B was 3.86 g. The mass of the compound A was 4.92 g.

Production Example 61

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether to obtain 1.15 parts by mass of thermal cationic polymerization initiator 2-30. The ratio of the mass of the compound B to the total mass of the compound B and the compound A was 0.998. The yield with respect to 4-methylthiophenol was 12%. The mass of the compound B was 1.1477 g. The mass of the compound A was 0.0023 g.

Production Example 62

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.65 parts by mass of thermal cationic polymerization initiator 2-31. The ratio of the mass of the compound B to the total mass of the compound B and the compound A was 0.450. The yield with respect to 4-methylthiophenol was 90%. The mass of the compound B was 3.89 g. The mass of the compound A was 4.76 g.

Tables 15 to 18 show the structure of the compound B in the thermal cationic polymerization agents of Production Examples 32 to 62 thus obtained, and the mass ratio of the compound B to the compounds A and B.

TABLE 15

| Segment | Production Example 32 | Production Example 33 | Production Example 34 | Production Example 35 |
|---|---|---|---|---|
| R10 | B⁻−(C₆F₄−F)₄ | B⁻−(C₆F₄−F)₄ | B⁻−(C₆F₄−F)₄ | B⁻−(C₆F₄−F)₄ |
| R7' | —O—CH₃ | —OH | —H | —C(=O)—H |

TABLE 15-continued

| Segment | | | | |
|---|---|---|---|---|
| R8 | —CH₃ | —CH₃ | —CH₃ | —CH₃ |
| R9 | 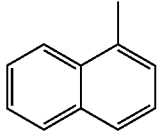 | 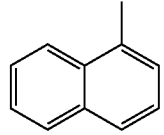 | 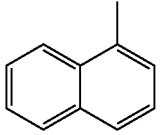 | 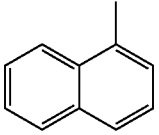 |
| Mass ratio | 97.0 | 97.2 | 97.1 | 96.9 |

| Segment | Production Example 36 | Production Example 37 | Production Example 38 | Production Example 39 |
|---|---|---|---|---|
| R10 | 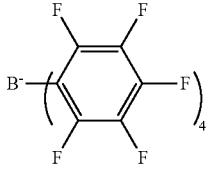 | 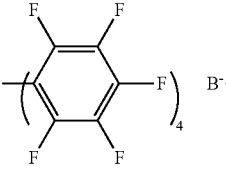 | 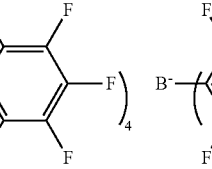 | 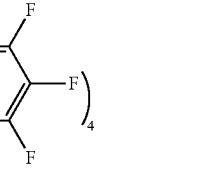 |
| R7' | —O—C(=O)—CH₃ | —O—C(=O)—O—CH₃ | —F | —CH₃ |
| R8 | —CH₃ | —CH₃ | —CH₃ | —CH₃ |
| R9 | 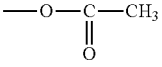 | 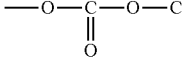 | 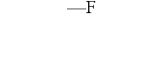 | 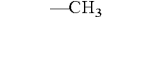 |
| Mass ratio | 96.7 | 97.4 | 96.2 | 97.3 |

TABLE 16

| Segment | Production Example 40 | Production Example 41 | Production Example 42 | Production Example 43 | Production Example 44 |
|---|---|---|---|---|---|
| R10 | 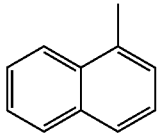 | 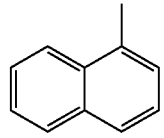 | 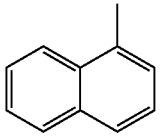 | 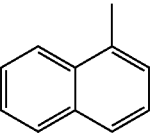 | 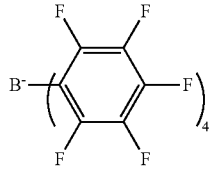 |
| R7' | —O—CH₃ | —O—CH₃ | —O—CH₃ | —O—CH₃ | —O—CH₃ |
| R8 | —CH₃ | —CH₃ | —CH₃ | —CH₃ | —CH₃ |
| R9 | 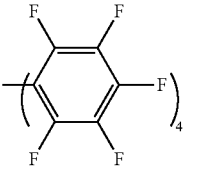 | 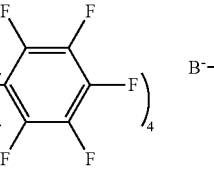 | 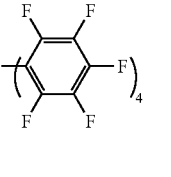 | 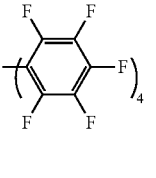 |  |
| Mass ratio | 97.4 | 96.2 | 96.8 | 97.2 | 96.8 |

TABLE 16-continued

| Segment | Production Example 45 | Production Example 46 | Production Example 47 | Production Example 48 | Production Example 49 |
|---|---|---|---|---|---|
| R10 | $B^-$—(C$_6$F$_5$)$_4$ | $B^-$—(C$_6$F$_5$)$_4$ | $B^-$—(C$_6$F$_5$)$_4$ | $B^-$—(C$_6$F$_5$)$_4$ | $B^-$—(C$_6$F$_5$)$_4$ |
| R7' | —O—CH$_3$ | —O—CH$_3$ | —O—CH$_3$ | —O—CH$_3$ | —O—CH$_3$ |
| R8 | —CH$_3$ | —CH$_3$ | —CH$_3$ | —CH$_3$ | —CH$_3$ |
| R9 | 4-biphenylyl | 2-naphthyl | 4-methoxyphenyl | 4-chlorophenyl | 2,6-dichlorophenyl |
| Mass ratio | 97.4 | 96.8 | 96.5 | 93.4 | 92.1 |

TABLE 17

| Segment | Production Example 50 | Production Example 51 | Production Example 52 | Production Example 53 | Production Example 54 |
|---|---|---|---|---|---|
| R10 | $B^-$—(C$_6$F$_5$)$_4$ | $B^-$—(C$_6$F$_5$)$_4$ | $B^-$—(C$_6$F$_5$)$_4$ | $B^-$—(C$_6$F$_5$)$_4$ | $B^-$—(C$_6$F$_5$)$_4$ |
| R7' | —O—CH$_3$ | —O—CH$_3$ | —O—CH$_3$ | —OH | —OH |
| R8 | —CH$_3$ | —CH$_3$ | —CH$_3$ | —CH$_3$ | —CH$_3$ |
| R9 | 1-naphthyl | 1-naphthyl | 1-naphthyl | 1-naphthyl | 1-naphthyl |
| Mass ratio | 98.4 | 90.0 | 55.0 | 98.4 | 90.0 |

| Segment | Production Example 55 | Production Example 56 | Production Example 57 | Production Example 58 |
|---|---|---|---|---|
| R10 | $B^-$—(C$_6$F$_5$)$_4$ | $B^-$—(C$_6$F$_5$)$_4$ | $B^-$—(C$_6$F$_5$)$_4$ | $B^-$—(C$_6$F$_5$)$_4$ |
| R7' | —OH | —F | —F | —F |
| R8 | —CH$_3$ | —CH$_3$ | —CH$_3$ | —CH$_3$ |

TABLE 17-continued

| R9 | 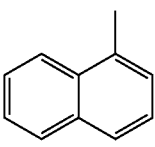 | 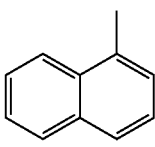 | 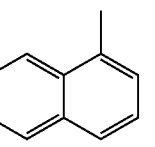 | 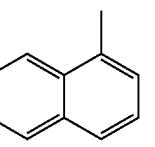 |
|---|---|---|---|---|
| Mass ratio | 55.0 | 98.4 | 90.0 | 55.0 |

TABLE 18

| Segment | Production Example 59 | Production Example 60 | Production Example 61 | Production Example 62 |
|---|---|---|---|---|
| R10 | 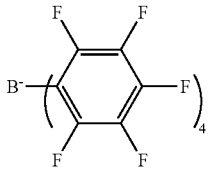 | 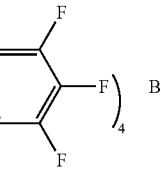 | 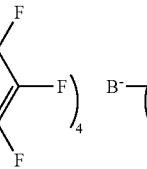 | 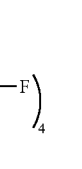 |
| R7' | —O—CH$_3$ | —O—CH$_3$ | —OH | —OH |
| R8 | —CH$_3$ | —CH$_3$ | —CH$_3$ | —CH$_3$ |
| R9 | 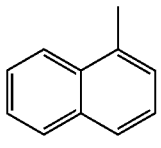 | 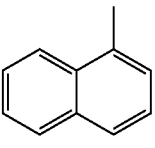 | 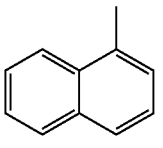 | 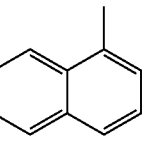 |
| Mass ratio | 99.7 | 44.0 | 99.8 | 45.0 |

Examples 67 to 93 and Reference Examples 7 to 10

The thermal cationic polymerization initiator of each example, a phenoxy resin (YP-50, manufactured by Nippon Steel Sumikin Chemical Co., Ltd.), a liquid epoxy resin (EP828, manufactured by Mitsubishi Chemical Corp.), a silane coupling agent (KBE403, manufactured by Shin-Etsu Chemical Co., Ltd.), and conductive particles (Ni/Au-plated resin particles (3.2 μm), manufactured by Shinihon Chemicals Corp.) were uniformly mixed at the mixing ratio shown in Tables 19 and 20 to prepare a thermally cationically polymerizable composition (anisotropically conductive adhesive composition) of each example. The numerical value of each component in Tables 19 and 20 represents part by mass. This composition was applied onto a 50 μm thick peel-off polyethylene terephthalate film subjected to surface peel-off treatment using a bar coater and heated in an oven preheated to 40° C. to convert the anisotropically conductive adhesive composition to a 20 μm thick anisotropically conductive adhesive film. A peel-off polyester film (cover film) was further laminated onto exposed surfaces of the anisotropically conductive adhesive film to obtain a laminate.

The peel-off polyester film (cover film) was peeled off from the anisotropically conductive adhesive film with both surfaces flanked by the peel-off polyester films. The exposed anisotropically conductive adhesive film was temporarily affixed to a 1.1 mm thick alkali glass substrate using a heat pressure bonder under conditions involving a heating temperature of 70° C., a pressure of 0.5 MPa, and 2 seconds.

The peel-off polyester film was peeled off from the surface of the temporarily affixed anisotropically conductive adhesive film. An IC chip with gold-plated bumps formed thereon (1.8 mm×20 mm×0.5 mm(t); gold-plated bump 30 μm×85 μm×15 μm(h)) was placed on the exposed anisotropically conductive adhesive film such that the bump-formed surface was positioned on the anisotropically conductive adhesive film side. A 50 μm thick Teflon® film was further placed thereon. Heat and pressure were applied thereonto using a heat pressure bonder under conditions involving 170° C., 60 MPa, and 5 seconds. In this way, a connecting structure having a structure in which the IC chip was anisotropically conductively connected with the alkali glass substrate via the anisotropically conductive adhesive film was obtained.

The connecting structure of each example thus obtained was subjected to appearance (uplift) evaluation, adhesive strength measurement, conductive particle capture efficiency measurement, and storage stability evaluation as described below. The obtained results are shown in Tables 19 and 20.

<Appearance (Uplift) Evaluation>

The interface of the connecting structure after attachment was visually observed from the alkali glass side to evaluate the degree of uplift generation according to criteria given below. A sample rated as A or B is desired.

A: no uplift was observed.

B: uplift generation was observed in a portion of the connecting structure.

C: uplift was observed in the whole surface of the connecting structure.

<Adhesive Strength Measurement>

The adhesive strength of the IC chip in the connecting structure was measured at a tool speed of 0.2 mm/sec using an adhesive strength tester (die shear tester SERIES 4000, manufactured by Nordson Corporation/DAGE). The adhesive strength is desirably 30 kg or higher.

<Conductive Particle Capture Efficiency Measurement>

The numbers of conductive particles present on the bumps (connection area per bump=2550 μm$^2$) of the pressure-bonded IC chip were counted under a microscope, and the average thereof was used as the number of captured particles. The number of captured particles was divided by the total number of conductive particles present per 2550 μm$^2$ of the anisotropically conductive adhesive film before anisotropically conductive connection, and the resulting value was used as conductive particle capture efficiency. This numerical value is desirably at least 17%, preferably 20% or more.

<Storage Stability>

1.0 part by mass of the thermal cationic polymerization initiator produced in each example was uniformly mixed with 100 parts by mass of AER 2603 (manufactured by Asahi Kasei E-materials Corp.). The composition thus prepared was stored at 30° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as "A" or "B" was determined to have adequate storage stability.

A: less than 2-fold increase in the viscosity after storage
B: 2-fold or more and less than 5-fold increase in the viscosity after storage
C: 5-fold or more and less than 10-fold increase in the viscosity after storage

TABLE 19

| Segment | Ex. 67 | Ex. 68 | Ex. 69 | Ex. 70 | Ex. 71 | Ex. 72 | Ex. 73 | Ex. 74 | Ex. 75 | Ex. 76 | Ex. 77 | Ex. 78 | Ex. 79 | Ex. 80 | Ex. 81 | Ex. 82 | Ex. 83 |
|---|---|---|---|---|---|---|---|---|---|---|---|---|---|---|---|---|---|
| Thermal cationic polymerization initiator 2-1 | 10 | | | | | | | | | | | | | | | | |
| Thermal cationic polymerization initiator 2-2 | | 10 | | | | | | | | | | | | | | | |
| Thermal cationic polymerization initiator 2-3 | | | 10 | | | | | | | | | | | | | | |
| Thermal cationic polymerization initiator 2-4 | | | | 10 | | | | | | | | | | | | | |
| Thermal cationic polymerization initiator 2-5 | | | | | 10 | | | | | | | | | | | | |
| Thermal cationic polymerization initiator 2-6 | | | | | | 10 | | | | | | | | | | | |
| Thermal cationic polymerization initiator 2-7 | | | | | | | 10 | | | | | | | | | | |
| Thermal cationic polymerization initiator 2-8 | | | | | | | | 10 | | | | | | | | | |
| Thermal cationic polymerization initiator 2-9 | | | | | | | | | 10 | | | | | | | | |
| Thermal cationic polymerization initiator 2-10 | | | | | | | | | | 10 | | | | | | | |
| Thermal cationic polymerization initiator 2-11 | | | | | | | | | | | 10 | | | | | | |
| Thermal cationic polymerization initiator 2-12 | | | | | | | | | | | | 10 | | | | | |
| Thermal cationic polymerization initiator 2-13 | | | | | | | | | | | | | 10 | | | | |
| Thermal cationic polymerization initiator 2-14 | | | | | | | | | | | | | | 10 | | | |
| Thermal cationic polymerization initiator 2-15 | | | | | | | | | | | | | | | 10 | | |
| Thermal cationic polymerization initiator 2-16 | | | | | | | | | | | | | | | | | 10 |

TABLE 19-continued

| Segment | Ex. 67 | Ex. 68 | Ex. 69 | Ex. 70 | Ex. 71 | Ex. 72 | Ex. 73 | Ex. 74 | Ex. 75 | Ex. 76 | Ex. 77 | Ex. 78 | Ex. 79 | Ex. 80 | Ex. 81 | Ex. 82 | Ex. 83 |
|---|---|---|---|---|---|---|---|---|---|---|---|---|---|---|---|---|---|
| Thermal cationic polymerization initiator 2-17 | | | | | | | | | | | | | | | | | 10 |
| Thermal cationic polymerization initiator 2-18 | | | | | | | | | | | | | | | | | |
| Thermal cationic polymerization initiator 2-19 | | | | | | | | | | | | | | | | | |
| Thermal cationic polymerization initiator 2-20 | | | | | | | | | | | | | | | | | |
| Thermal cationic polymerization initiator 2-21 | | | | | | | | | | | | | | | | | |
| Thermal cationic polymerization initiator 2-22 | | | | | | | | | | | | | | | | | |
| Thermal cationic polymerization initiator 2-23 | | | | | | | | | | | | | | | | | |
| Thermal cationic polymerization initiator 2-24 | | | | | | | | | | | | | | | | | |
| Thermal cationic polymerization initiator 2-25 | | | | | | | | | | | | | | | | | |
| Thermal cationic polymerization initiator 2-26 | | | | | | | | | | | | | | | | | |
| Thermal cationic polymerization initiator 2-27 | | | | | | | | | | | | | | | | | |
| Thermal cationic polymerization initiator 2-28 | | | | | | | | | | | | | | | | | |
| Thermal cationic polymerization initiator 2-29 | | | | | | | | | | | | | | | | | |
| Thermal cationic polymerization initiator 2-30 | | | | | | | | | | | | | | | | | |
| Thermal cationic polymerization initiator 2-31 | | | | | | | | | | | | | | | | | |
| Phenoxy resin (YP-50, Nippon Steel & Sumikin Chemical Co., Ltd.) | 50 | 50 | 50 | 50 | 50 | 50 | 50 | 50 | 50 | 50 | 50 | 50 | 50 | 50 | 50 | 50 | 50 |
| Liquid epoxy resin (EP828, Mitsubishi Chemical Corp.) | 35 | 35 | 35 | 35 | 35 | 35 | 35 | 35 | 35 | 35 | 35 | 35 | 35 | 35 | 35 | 35 | 35 |
| Silane coupling agent (KBE403, Shin-Etsu Chemical Co., Ltd.) | 5 | 5 | 5 | 5 | 5 | 5 | 5 | 5 | 5 | 5 | 5 | 5 | 5 | 5 | 5 | 5 | 5 |
| Conductive particles (Ni/Au-plated resin particles (3.2 μm)) (Shinihon Chemicals Corp.) | 20 | 20 | 20 | 20 | 20 | 20 | 20 | 20 | 20 | 20 | 20 | 20 | 20 | 20 | 20 | 20 | 20 |
| Appearance evaluation | A | A | A | A | A | A | A | A | B | B | B | B | B | B | B | B | B |
| Adhesive strength (kg) | 93.2 | 91.5 | 89.5 | 96.2 | 94.2 | 93.5 | 90.2 | 94.2 | 82.3 | 75.3 | 84.2 | 78.2 | 74.6 | 71.1 | 72.3 | 71.5 | 75.2 |
| Conductive particle capture efficiency (%) | 24.1 | 22.2 | 23.1 | 23.3 | 20.9 | 20.8 | 20.5 | 21.5 | 18.3 | 19.2 | 18.5 | 18.7 | 19.3 | 18.6 | 19.4 | 19.2 | 18.5 |
| Storage stability | A | A | A | A | B | B | B | A | A | A | A | A | A | A | A | A | A |

TABLE 20

| Segment | Example 84 | Example 85 | Example 86 | Example 87 | Example 88 | Example 89 | Example 90 | Example 91 |
|---|---|---|---|---|---|---|---|---|
| Thermal cationic polymerization initiator 2-1 | | | | | | | | |

TABLE 20-continued

| | | | | | | | | |
|---|---|---|---|---|---|---|---|---|
| Thermal cationic polymerization initiator 2-2 | | | | | | | | |
| Thermal cationic polymerization initiator 2-3 | | | | | | | | |
| Thermal cationic polymerization initiator 2-4 | | | | | | | | |
| Thermal cationic polymerization initiator 2-5 | | | | | | | | |
| Thermal cationic polymerization initiator 2-6 | | | | | | | | |
| Thermal cationic polymerization initiator 2-7 | | | | | | | | |
| Thermal cationic polymerization initiator 2-8 | | | | | | | | |
| Thermal cationic polymerization initiator 2-9 | | | | | | | | |
| Thermal cationic polymerization initiator 2-10 | | | | | | | | |
| Thermal cationic polymerization initiator 2-11 | | | | | | | | |
| Thermal cationic polymerization initiator 2-12 | | | | | | | | |
| Thermal cationic polymerization initiator 2-13 | | | | | | | | |
| Thermal cationic polymerization initiator 2-14 | | | | | | | | |
| Thermal cationic polymerization initiator 2-15 | | | | | | | | |
| Thermal cationic polymerization initiator 2-16 | | | | | | | | |
| Thermal cationic polymerization initiator 2-17 | | | | | | | | |
| Thermal cationic polymerization initiator 2-18 | 10 | | | | | | | |
| Thermal cationic polymerization initiator 2-19 | | 10 | | | | | | |
| Thermal cationic polymerization initiator 2-20 | | | 10 | | | | | |
| Thermal cationic polymerization initiator 2-21 | | | | 10 | | | | |
| Thermal cationic polymerization initiator 2-22 | | | | | 10 | | | |
| Thermal cationic polymerization initiator 2-23 | | | | | | 10 | | |
| Thermal cationic polymerization initiator 2-24 | | | | | | | 10 | |
| Thermal cationic polymerization initiator 2-25 | | | | | | | | 10 |
| Thermal cationic polymerization initiator 2-26 | | | | | | | | |
| Thermal cationic polymerization initiator 2-27 | | | | | | | | |
| Thermal cationic polymerization | | | | | | | | |

TABLE 20-continued

| | | | | | | | | |
|---|---|---|---|---|---|---|---|---|
| initiator 2-28 Thermal cationic polymerization initiator 2-29 Thermal cationic polymerization initiator 2-30 Thermal cationic polymerization initiator 2-31 | | | | | | | | |
| Phenoxy resin (YP-50, Nippon Steel & Sumikin Chemical Co., Ltd.) | 50 | 50 | 50 | 50 | 50 | 50 | 50 | 50 |
| Liquid epoxy resin (EP828, Mitsubishi Chemical Corp.) | 35 | 35 | 35 | 35 | 35 | 35 | 35 | 35 |
| Silane coupling agent (KBE403, Shin-Etsu Chemical Co., Ltd.) | 5 | 5 | 5 | 5 | 5 | 5 | 5 | 5 |
| Conductive particles (Ni/Au-plated resin particles (3.2 μm)) (Shinihon Chemicals Corp.) | 20 | 20 | 20 | 20 | 20 | 20 | 20 | 20 |
| Appearance evaluation | B | A | A | A | A | A | A | A |
| Adhesive strength (kg) | 73.5 | 86.3 | 86.8 | 87.5 | 89.2 | 88.5 | 88.2 | 87.3 |
| Conductive particle capture efficiency (%) | 18.1 | 23.4 | 22.4 | 23.6 | 23.5 | 23.0 | 23.6 | 22.5 |
| Storage stability | A | A | A | A | A | A | A | A |

| Segment | Example 92 | Example 93 | Reference Example 7 | Reference Example 8 | Reference Example 9 | Reference Example 10 |
|---|---|---|---|---|---|---|
| Thermal cationic polymerization initiator 2-1 | | | | | | |
| Thermal cationic polymerization initiator 2-2 | | | | | | |
| Thermal cationic polymerization initiator 2-3 | | | | | | |
| Thermal cationic polymerization initiator 2-4 | | | | | | |
| Thermal cationic polymerization initiator 2-5 | | | | | | |
| Thermal cationic polymerization initiator 2-6 | | | | | | |
| Thermal cationic polymerization initiator 2-7 | | | | | | |
| Thermal cationic polymerization initiator 2-8 | | | | | | |
| Thermal cationic polymerization initiator 2-9 | | | | | | |
| Thermal cationic polymerization initiator 2-10 | | | | | | |
| Thermal cationic polymerization initiator 2-11 | | | | | | |
| Thermal cationic polymerization initiator 2-12 | | | | | | |
| Thermal cationic polymerization initiator 2-13 | | | | | | |
| Thermal cationic polymerization initiator 2-14 | | | | | | |

TABLE 20-continued

| | | | | | | |
|---|---|---|---|---|---|---|
| Thermal cationic polymerization initiator 2-15 | | | | | | |
| Thermal cationic polymerization initiator 2-16 | | | | | | |
| Thermal cationic polymerization initiator 2-17 | | | | | | |
| Thermal cationic polymerization initiator 2-18 | | | | | | |
| Thermal cationic polymerization initiator 2-19 | | | | | | |
| Thermal cationic polymerization initiator 2-20 | | | | | | |
| Thermal cationic polymerization initiator 2-21 | | | | | | |
| Thermal cationic polymerization initiator 2-22 | | | | | | |
| Thermal cationic polymerization initiator 2-23 | | | | | | |
| Thermal cationic polymerization initiator 2-24 | | | | | | |
| Thermal cationic polymerization initiator 2-25 | | | | | | |
| Thermal cationic polymerization initiator 2-26 | 10 | | | | | |
| Thermal cationic polymerization initiator 2-27 | | 10 | | | | |
| Thermal cationic polymerization initiator 2-28 | | | 10 | | | |
| Thermal cationic polymerization initiator 2-29 | | | | 10 | | |
| Thermal cationic polymerization initiator 2-30 | | | | | 10 | |
| Thermal cationic polymerization initiator 2-31 | | | | | | 10 |
| Phenoxy resin (YP-50, Nippon Steel & Sumikin Chemical Co., Ltd.) | 50 | 50 | 50 | 50 | 50 | 50 |
| Liquid epoxy resin (EP828, Mitsubishi Chemical Corp.) | 35 | 35 | 35 | 35 | 35 | 35 |
| Silane coupling agent (KBE403, Shin-Etsu Chemical Co., Ltd.) | 5 | 5 | 5 | 5 | 5 | 5 |
| Conductive particles (Ni/Au-plated resin particles (3.2 μm)) (Shinihon Chemicals Corp.) | 20 | 20 | 20 | 20 | 20 | 20 |
| Appearance evaluation | A | A | C | C | C | C |
| Adhesive strength (kg) | 82.1 | 90.2 | 20.1 | 19.8 | 18.3 | 19.1 |
| Conductive particle capture efficiency (%) | 23.5 | 21.2 | 16.3 | 16.4 | 16.2 | 16.5 |
| Storage stability | A | A | C | A | C | A |

[Cation-generating Agent 1]

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.80 parts by mass of cation-generating agent 1. The ratio of the mass of the compound A to the total mass of the compound A and the compound B was 0.030. The yield with respect to 4-methoxythioanisole was 80.0%. The mass of the compound A was 0.23 g, and the mass of the compound B was 7.57 g.

[Cation-generating Agent 2]

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.88 parts by mass of cation-generating agent 2. The ratio of the mass of the compound A to the total mass of the compound A and the compound B was 0.028. The yield with respect to 4-methylthiophenol was 82%. The mass of the compound A was 0.22 g, and the mass of the compound B was 7.66 g.

[Cation-generating Agent 3]

1.69 parts by mass of 4-acetoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.57 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.81 parts by mass of cation-generating agent 3. The ratio of the mass of the compound A to the total mass of the compound A and the compound B was 0.033. The yield with respect to 4-acetoxythioanisole was 79%. The mass of the compound A was 0.26 g, and the mass of the compound B was 7.55 g.

[Cation-generating Agent 4]

1.43 parts by mass of 4-fluorothioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.33 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.70 parts by mass of cation-generating agent 4. The ratio of the mass of the compound A to the total mass of the compound A and the compound B was 0.038. The yield with respect to 4-fluorothioanisole was 80%. The mass of the compound A was 0.29 g, and the mass of the compound B was 7.41 g.

[Cation-generating Agent 5]

1.39 parts by mass of 4-methylthioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.30 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.09 parts by mass of cation-generating agent 5. The ratio of the mass of the compound A to the total mass of the compound A and the compound B was 0.027. The yield with respect to 4-methylthioanisole was 74%. The mass of the compound A was 0.19 g, and the mass of the compound B was 6.90 g.

[Cation-generating Agent 6]

1.55 parts by mass of 4-methoxythioanisole, 1.95 parts by mass of silver borofluoride, 1.41 parts by mass of α-chloro-o-xylene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.46 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.41 parts by mass of cation-generating agent 6. The ratio of the mass of the compound A to the total mass of the compound A and the compound B was 0.026. The yield with respect to 4-methoxylthioanisole was 79%. The mass of the compound A was 0.19 g, and the mass of the compound B was 7.22 g.

[Cation-generating Agent 7]

1.55 parts by mass of 4-methoxythioanisole, 1.95 parts by mass of silver borofluoride, 1.57 parts by mass of p-methoxybenzyl chloride, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.26 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 7.06 parts by mass of cation-generating agent 7. The ratio of the mass of the compound A to the total mass of the compound A and the compound B was 0.035. The yield with respect to 4-methoxythioanisole was 74%. The mass of the compound A was 0.25 g, and the mass of the compound B was 6.81 g.

[Cation-generating Agent 8]

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.28 parts by mass of cation-generating agent 8. The ratio of the mass of the compound A to the total mass of the compound A and the compound B was 0.450. The yield with respect to 4-methoxythioanisole was 85%. The mass of the compound A was 3.73 g, and the mass of the compound B was 4.55 g.

[Cation-generating Agent 9]

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 45° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.31 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.16 parts by mass of cation-generating agent 9. The ratio of the mass of the compound A to the total mass of the compound A and the compound B was 0.450. The yield with respect to 4-methylthiophenol was 85%. The mass of the compound A was 3.67 g, and the mass of the compound B was 4.49 g.

[Cation-generating Agent 10]

1.55 parts by mass of 4-methoxythioanisole, 1.95 parts by mass of silver borofluoride, 1.77 parts by mass of 1-chloromethyl naphthalene, and 10.0 parts by mass of acetone were uniformly mixed and reacted at 25° C. for 24 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.43 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer, and the residue was recrystallized from diethyl ether three times to obtain 5.70 parts by mass of cation-generating agent 10. As a result of analysis, only the compound B was contained therein.

[Cation-generating Agent 11]

1.41 parts by mass of 4-methylthiophenol, 1.95 parts by mass of silver borofluoride, 1.77 parts by mass of 1-chloromethyl naphthalene, and 10.0 parts by mass of acetone were uniformly mixed and reacted at 25° C. for 72 hours. After removal of silver chloride, the reaction solution was transferred to a rotary evaporator, and the solvent was distilled off. The obtained residue was reprecipitated with 10.0 parts by mass of acetone and 10.0 parts by mass of hexane. 3.48 parts by mass of the obtained precipitate, 6.86 parts by mass of lithium tetrakis(pentafluorophenyl) borate, and 10 parts by mass of acetone were uniformly mixed and reacted at 25° C. for 24 hours. 10.0 parts by mass of distilled water were added to the reaction solution to wash the product. The solvent was distilled off under reduced pressure from the organic layer to obtain 8.65 parts by mass of cation-generating agent 11. The ratio of the mass of the compound A to the total mass of the compound A and the compound B was 0.550. The yield with respect to 4-methylthiophenol was 90%. The mass of the compound A was 4.76 g. The mass of the compound B was 3.89 g.

Example 94

47 g of a bisphenol A-type liquid epoxy resin, 3 g of 3-ethyl-3{[(3-ethyloxetan-3-yl)methoxy]methyl}oxetane, and 50 g of a phenoxy resin having an average molecular weight of 25,000 were dissolved in methyl ethyl ketone to obtain a solution having a solid content of 50%.

100 parts by mass of the cation-generating agent 1 (ratio of compound A: 0.030) and 5 parts by mass of 4-hydroxyphenyldimethylsulfonium methyl sulfate were mixed and dissolved in methyl ethyl ketone to prepare 50 parts by mass of a solution. An organic binder resin component and the mixture of the cation-generating agent 1 and 4-hydroxyphenyldimethylsulfonium methyl sulfate were mixed at a solid mass ratio of 100:2. Conductive particles containing a 0.2 μm thick nickel layer on the surface of particles with a benzoguanamine resin core and having an average particle size of 10.1 μm were further mixed therewith at 8% by volume with respect to the total volume of the organic binder, and dispersed to obtain a dispersion. Then, the dispersion was applied onto a 50 μm thick polyethylene terephthalate film and dried by blowing air of 40° C. to obtain film-shaped connecting material 1 having a film thickness of 20 μm.

Example 95

Film-shaped connecting material 2 was obtained in the same way as in Example 94 except that the cation-generating agent 2 (ratio of compound A: 0.028) was used instead of the cation-generating agent 1 of Example 94.

Example 96

Film-shaped connecting material 3 was obtained in the same way as in Example 94 except that the cation-generating agent 3 (ratio of compound A: 0.033) was used instead of the cation-generating agent 1 of Example 94.

Example 97

Film-shaped connecting material 4 was obtained in the same way as in Example 94 except that the cation-generating agent 4 (ratio of compound A: 0.038) was used instead of the cation-generating agent 1 of Example 94.

Example 98

Film-shaped connecting material 5 was obtained in the same way as in Example 94 except that the cation-generating agent 5 (ratio of compound A: 0.027) was used instead of the cation-generating agent 1 of Example 94.

Example 99

Film-shaped connecting material 6 was obtained in the same way as in Example 94 except that the cation-generating agent 6 (ratio of compound A: 0.026) was used instead of the cation-generating agent 1 of Example 94.

Example 100

Film-shaped connecting material 7 was obtained in the same way as in Example 94 except that the cation-generating agent 7 (ratio of compound A: 0.035) was used instead of the cation-generating agent 1 of Example 94.

Example 101

Film-shaped connecting material 8 was obtained in the same way as in Example 95 except that the cation-generating agent 8 (ratio of compound A: 0.450) was used instead of the cation-generating agent 1 of Example 95.

Example 102

Film-shaped connecting material 9 was obtained in the same way as in Example 94 except that the cation-generating agent 9 (ratio of compound A: 0.450) was used instead of the cation-generating agent 1 of Example 94.

Example 103

Film-shaped connecting material 10 was obtained in the same way as in Example 95 except that the cation-generating agent 11 (ratio of compound A: 0.550) was used instead of the cation-generating agent 1 of Example 95.

Example 104

Film-shaped connecting material 11 was obtained (ratio of compound A: 0.240) in the same way as in Example 94 except that 50 parts by mass of the cation-generating agent 1 (ratio of compound A: 0.030) and the cation-generating agent 9 (ratio of compound A: 0.450) were used instead of 100 parts by mass of the cation-generating agent 1 (ratio of compound A: 0.030) of Example 94.

Example 105

Film-shaped connecting material 12 was obtained (ratio of compound A: 0.165) in the same way as in Example 94 except that 70 parts by mass of the cation-generating agent 10 (ratio of compound A: 0) and the cation-generating agent 11 (ratio of compound A: 0.550) were used instead of 100 parts by mass of the cation-generating agent 1 (ratio of compound A: 0.030) of Example 94.

Comparative Example 2

Film-shaped connecting material 13 was obtained in the same way as in Example 94 except that the cation-generating agent 10 (ratio of compound A: 0) was used instead of the cation-generating agent 1 of Example 94.

(Method for Preparing Substrate for Evaluation)

A film-shaped connecting material having a width of 3 mm and a length of 40 mm was temporarily affixed to a central portion on a 150 μm thick non-alkali glass substrate (surface resistance: 300 Ω/sq, width: 30 mm, length: 45 mm) with a thin indium oxide film formed on the whole surface. Pressure was applied thereto at 50° C. at 0.3 MPa for 3 seconds using a 3.5 mm wide pressure bonding head. Then, the base film of polyethylene terephthalate was peeled off. A 3.0 Tim wide tin/silver (98/2)-solder plated copper foil (100 μm thick, plate thickness: 10 μm, length: 40 mm) was temporarily connected to the exposed surface. Then, pressure was applied thereto at 150° C. at 1.0 MPa for 5 seconds using a 3.5 mm wide pressure bonding head for pressure bonding. After the pressure bonding, the substrate was left at 25° C. for 1 hour to obtain a substrate for evaluation.

(Warpage Measurement)

The warpage of the copper foil portion (long side portion) was measured (measurement length: 15.1 mm) from the glass surface side of the non-alkali glass substrate mentioned above using a stylus-type surface roughness tester (SE-3H, manufactured by Kosaka Laboratory Ltd.). Specifically, the displacement between the measurement start site and the central site was used as warpage. A sample having warpage of smaller than 20 μm was rated as "o"; a sample having warpage of 20 μm or larger and smaller than 25 μm was rated as "Δ"; and a sample having warpage of 25 μm or larger was rated as "x".

(Connection Reliability Test)

Ten substrates for evaluation prepared in the same way were subjected to the cooling/heating cycle test (100 cycles each involving −40° C. for 30 minutes and 100° C. for 30 minutes) and visually evaluated for the presence or absence of delamination or glass cracks. In this test, the case where no substrates having delamination or crack(s) were observed was rated as "o"; and the case where even one substrate having delamination or crack(s) was observed was rated as "x".

(Measurement of Amount of Void)

Voids in the connected portion (the back side of the copper foil) were observed from the glass surface side of the non-alkali glass substrate mentioned above using a microscope (VHX-2000 manufactured by Keyence Corp.). Voids having a major axis of 2 μm or larger were measured, and the void areas were integrated. The total void area with respect to the connection area was used as a void ratio. A sample having a void ratio of 5% or less was rated as "o"; a sample having a void ratio of 5% or more and less than 10% was rated as "Δ"; and a sample having a void ratio of 10% or more was rated as "x".

(Epoxy Reaction Rate Measurement)

The epoxy reaction rate was determined by measuring an epoxy group absorbance ratio by the FT-IR method. First, a 3 mm wide and 20 mm long anisotropically conductive adhesive film formed on a film base material was sandwiched between 30 μm thick Teflon tapes and pressure-bonded at 150° C. at 0.3 MPa for 5 seconds using a 3.5 mm wide heat pressure head to prepare a sample. The FT-IR measurement was conducted both before and after pressure bonding. The epoxy group reaction rate was calculated from the absorbance ratio between before and after pressure bonding. Methyl group absorption intensity was used as an internal standard for a method for calculating the epoxy group absorbance ratio. The reaction rate was calculated according to the following expression:

$$\text{Reaction rate (\%)} = (1-((a/b)/(A/B))) \times 100$$

A: epoxy group absorption intensity before pressure bonding

B: methyl group absorption intensity before pressure bonding
a: epoxy group absorption intensity after pressure bonding
b: methyl group absorption intensity after pressure bonding In terms of the epoxy reaction rate under conditions involving 150° C. and 5 seconds
○: 90% or more
Δ: 80% or more and less than 90%
x: less than 70%

The results of thus evaluating the samples of Examples 94 to 105 and Comparative Example 2 obtained as described above are shown in Table 21. As is evident from Table 21, the connecting structures according to Examples generate few voids and low warpage, cause less reduction in peeling strength, and exhibit favorable connection reliability.

as avoid ratio. A sample having a void ratio of 5% or less was rated as "○"; a sample having a void ratio of 5% or more and less than 10% was rated as "Δ"; and a sample having a void ratio of 10% or more was rated as "x". A sample rated as "○" was determined to be favorable with a sufficiently small amount of voids. The results are shown in Table 22.

(3) Qualitative and Quantitative Determination of Ethyl Acetate

Ethyl acetate contained in the thermal cationic polymerization initiator according to each example was identified by GC-MS (GCMS-TQ8040, manufactured by Shimadzu Corp.) and quantitatively determined by GC (GC-2025, manufactured by Shimadzu Corp.) using an internal calibration curve.

TABLE 21

|  | Example 94 | Example 95 | Example 96 | Example 97 | Example 98 | Example 99 | Example 100 | Example 101 | Example 102 | Example 103 | Example 104 | Example 105 | Comparative Example 2 |
|---|---|---|---|---|---|---|---|---|---|---|---|---|---|
| Warpage evaluation | ○ | Δ | Δ | ○ | ○ | ○ | ○ | Δ | Δ | Δ | ○ | ○ | Δ |
| Connection reliability | ○ | ○ | ○ | ○ | ○ | ○ | ○ | ○ | ○ | ○ | ○ | ○ | x |
| Void evaluation | ○ | ○ | ○ | ○ | ○ | ○ | ○ | ○ | ○ | ○ | ○ | ○ | Δ |
| Epoxy reaction rate | ○ | ○ | ○ | ○ | ○ | Δ | ○ | ○ | ○ | ○ | ○ | ○ | ○ |

Examples 106 and 107 and Reference Examples 11 and 12

(1) Curing Properties 1.0 part by mass of the thermal cationic polymerization initiator produced in Production Example 1 was uniformly mixed with 100 parts by mass of AER 2603 (manufactured by Asahi Kasei E-materials Corp.). 1.0 g of the mixture (composition) thus obtained was heated at 80° C. for 30 minutes to prepare a cured product according to Example 106. The thermal cationic polymerization initiators used in Example 107 and Reference Examples 11 and 12 were prepared, for example, by appropriately mixing ethyl acetate at an ethyl acetate content of 5000 ppm, 2 ppm, and 15000 ppm, respectively, with the thermal cationic polymerization initiator produced in Production Example 1. These thermal cationic polymerization initiators were each used in the same way as above to prepare cured products according to Example 107 and Reference Examples 11 and 12. The cured products were evaluated on the basis of surface texture as follows: a sample rated as "A" was determined to have favorable curing properties. The results are shown in Table 22.

"A": not sticky
"B": sticky
"C": liquid (2) Amount of Void

Voids on the surface of each cured product were observed using a microscope (VHX-2000 manufactured by Keyence Corp.) targeting the cured products prepared in the evaluation of curing properties mentioned above. Voids having a major axis of 2 μm or larger were measured, and the void areas were integrated. The total void area per mm$^2$ was used

TABLE 22

| Segment | Example 106 | Example 107 | Reference Example 11 | Reference Example 12 |
|---|---|---|---|---|
| Ethyl acetate content/ppm | 1000 | 5000 | 2 | 15000 |
| Curing properties | A | A | B | A |
| Void | ○ | ○ | ○ | x |

Examples 108 and 109 and Reference Examples 13 and 14

(1) Curing Properties 1.0 part by mass of a thermal cationic polymerization initiator obtained by removing ethyl acetate from the thermal cationic polymerization initiator produced in Production Example 1 and mixing 1000 ppm of AgCl with the resulting product was uniformly mixed with 100 parts by mass of AER 2603 (manufactured by Asahi Kasei E-materials Corp.). 1.0 g of the mixture (composition) thus obtained was heated at 80° C. for 30 minutes to prepare a cured product according to Example 108. The thermal cationic polymerization initiators used in Example 109 and Reference Examples 13 and 14 were prepared, for example, by appropriately mixing AgCl at an AgCl content of 5000 ppm, 2 ppm, and 15000 ppm, respectively, with the thermal cationic polymerization initiator produced in Production Example 1. These thermal cationic polymerization initiators were each used in the same way as above to prepare cured products according to Example 109 and Reference Examples 13 and 14. The cured products were evaluated on the basis of surface texture as follows: a sample rated as "A" was determined to have favorable curing properties.

"A": not sticky

"B": sticky

"C": liquid (2) Storage Stability

The composition prepared in the evaluation of curing properties mentioned above was stored at 25° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as "A" or "B" was determined to have adequate storage stability.

"A": less than 2-fold increase in the viscosity after storage

"B": 2-fold or more and less than 5-fold increase in the viscosity after storage "C": 5-fold or more and less than 10-fold increase in the viscosity after storage "D": 10-fold or more increase in the viscosity after storage, or gelled (3) Qualitative and Quantitative Determination of Silver Chloride Silver chloride contained in the thermal cationic polymerization initiator according to each example was qualitatively determined by XRD (SmartLab 3, manufactured by Rigaku Corp.) and quantitatively determined by ICP-MS (Agilent 7900, manufactured by Agilent Technologies, Inc.).

TABLE 23

| Segment | Example 108 | Example 109 | Reference Example 13 | Reference Example 14 |
|---|---|---|---|---|
| AgCl content/ppm | 1000 | 5000 | 2 | 15000 |
| Curing properties | A | A | A | C |
| Storage stability | A | A | B | A |

Examples 110 and 111 and Reference Examples 15 and 16

(1) Curing Properties 1.0 part by mass of a thermal cationic polymerization initiator, which was obtained by removing ethyl acetate from the thermal cationic polymerization initiator produced in Production Example 1 and adding thereto 1000 ppm of 4-(methylthio) phenol, was uniformly mixed with 100 parts by mass of AER 2603 (manufactured by Asahi Kasei E-materials Corp.). 1.0 g of the mixture (composition) thus obtained was heated at 80° C. for 30 minutes to prepare a cured product according to Example 110. The thermal cationic polymerization initiators used in Example 111 and Reference Examples 15 and 16 were prepared, for example, by appropriately mixing 4-(methylthio)phenol at a 4-(methylthio)phenol content of 3000 ppm, 2 ppm, and 6000 ppm, respectively, with the thermal cationic polymerization initiator produced in Production Example 1. These thermal cationic polymerization initiators were each used in the same way as above to prepare cured products according to Example 111 and Reference Examples 15 and 16. The cured products were evaluated on the basis of surface texture as follows: a sample rated as "A" was determined to have favorable curing properties.

"A": not sticky

"B": sticky

"C": liquid (2) Storage Stability

The composition prepared in the evaluation of curing properties mentioned above was stored at 25° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as or "B" was determined to have adequate storage stability.

"A": less than 2-fold increase in the viscosity after storage

"B": 2-fold or more and less than 5-fold increase in the viscosity after storage "C": 5-fold or more and less than 10-fold increase in the viscosity after storage "D": 10-fold or more increase in the viscosity after storage, or gelled (3) Qualitative and Quantitative Determination of 4-(Methylthio)Phenol 4-(Methylthio)phenol contained in the thermal cationic polymerization initiator according to each example was identified by GC-MS and quantitatively determined by GC using an internal calibration curve.

TABLE 24

| Segment | Example 110 | Example 111 | Reference Example 15 | Reference Example 16 |
|---|---|---|---|---|
| 4-(Methylthio)phenol content/ppm | 1000 | 3000 | 2 | 6000 |
| Curing properties | A | A | A | C |
| Storage stability | A | A | B | A |

Examples 112 and 113 and Reference Examples 17 and 18

(1) Curing Properties 1.0 part by mass of a thermal cationic polymerization initiator, which was obtained by removing ethyl acetate from the thermal cationic polymerization initiator produced in Production Example 1 and adding thereto 1000 ppm of naphthalenemethanol, was uniformly mixed with 100 parts by mass of AER 2603 (manufactured by Asahi Kasei E-materials Corp.). 1.0 g of the mixture (composition) thus obtained was heated at 80° C. for 30 minutes to prepare a cured product according to Example 112. The thermal cationic polymerization initiators used in Example 113 and Reference Examples 17 and 18 were prepared, for example, by mixing naphthalenemethanol at a naphthalenemethanol content of 5000 ppm, 2 ppm, and 6000 ppm, respectively, with the thermal cationic polymerization initiator produced in Production Example 1. These thermal cationic polymerization initiators were each used in the same way as above to prepare cured products according to Example 113 and Reference Examples 17 and 18. The cured products were evaluated on the basis of surface texture as follows: a sample rated as "A" was determined to have favorable curing properties.

"A": not sticky
"B": sticky
"C": liquid (2) Storage Stability

The composition prepared in the evaluation of curing properties mentioned above was stored at 25° C. for 1 week. The viscosity of the composition of each example was measured both before and after storage to determine the fold increase in the viscosity. The storage stability of the composition of each example was evaluated on the basis of the fold increase in the viscosity according to criteria given below. The viscosity was measured at 25° C. using a BM-type viscometer. A sample rated as "A" or "B" was determined to have adequate storage stability.

"A": less than 2-fold increase in the viscosity after storage
"B": 2-fold or more and less than 5-fold increase in the viscosity after storage
"C": 5-fold or more and less than 10-fold increase in the viscosity after storage
"D": 10-fold or more increase in the viscosity after storage, or gelled (3) Qualitative and Quantitative Determination of Naphthalenemethanol Naphthalenemethanol contained in the thermal cationic polymerization initiator according to each example was identified by GC-MS and quantitatively determined by GC using an internal calibration curve.

TABLE 25

| Segment | Example 112 | Example 113 | Reference Example 17 | Reference Example 18 |
|---|---|---|---|---|
| Naphthalenemethanol content/ppm | 1000 | 5000 | 2 | 6000 |
| Curing properties | A | A | B | A |
| Storage stability | A | A | A | C |

The present application is based on Japanese Patent Application No. 2013-198802 filed on Sep. 25, 2013, Japanese Patent Application No. 2013-251153 filed on Dec. 4, 2013, Japanese Patent Application No. 2014-017774 filed on Jan. 31, 2014, and Japanese Patent Application No. 2014-017780 filed on Jan. 31, 2014, the contents of which are incorporated herein by reference in their entirety.

The invention claimed is:

1. A composition comprising:
an onium salt comprising a compound A represented by the general formula (1):

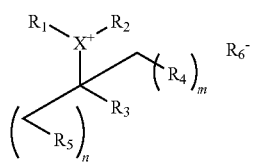

(1)

wherein $R_1$ and $R_2$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an alkyl group, an aralkyl group, an aryloxycarbonyl-group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfmyl group, an arylsulfmyl group, an alkylsulfonyl group, an arylsulfonyl group, a hydroxy(poly)alkyleneoxy group, an optionally substituted amino group, a cyano group, and a nitro group, and are the same or different from each other;

$R_3$, $R_4$, and $R_5$ each represent a group selected from the group consisting of an aryloxy group, an arylcarbonyl group, an aralkylcarbonyl group, an aryloxycarbonyl group, an aralkyl group, an aralkyloxycarbonyl group, an alkylcarbonyloxy group, an arylcarbonyloxy group, an aralkylcarbonyloxy group, an aryloxycarbonyloxy group, an aralkyloxycarbonyloxy group, an arylthiocarbonyl group, an arylthio group, an aryl group, an alkylsulfmyl group, an arylsulfinyl group, and an arylsulfonyl group;

X is sulfur;
n represents an integer of 0 to 3;
m represents an integer of 1 to 4;
n and m satisfy n+m<4; and
$R_6$ represents an atomic group capable of forming a monovalent anion; and
wherein the $R_6$ is one group selected from the group consisting of $SbY_6^-$, $PY_6^-$, $AsY_6^-$, $BY_4^-$, and $CY_3SO_3^-$ (wherein Y represents at least one selected from the group consisting of a hydrogen atom, an alkyl group, Cl, Br, and I), or is represented by the following general formula (3):

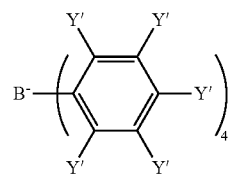

(3)

wherein each Y' represents a hydrogen atom, a halogen atom, or an alkyl group, and at least one of the Y' is a halogen atom;

an onium salt comprising a compound B represented by the general formula (2):

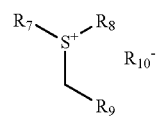

(2)

wherein $R_7$ and $R_8$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an aralkyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other;

$R_9$ represents a group selected from the group consisting of an aryloxy group, an arylcarbonyl group, an aralkylcarbonyl group, an aryloxycarbonyl group, an aralkyl group, an aralkyloxycarbonyl group, an alkylcarbonyloxy group, an arylcarbonyloxy group, an aralkylcarbonyloxy group, an aryloxycarbonyloxy group, an aralkyloxycarbonyloxy group, an arylthiocarbonyl group, an arylthio group, an aryl group, an alkylsulfinyl group, an arylsulfinyl group, and an arylsulfonyl group;

$R_{10}$ represents an atomic group capable of forming a monovalent anion; and wherein the $R_{10}$ is one group selected from the group consisting of $SbY_6^-$, $PY_6^-$, $AsY_6^-$, $BY_4^-$, and $CY_3SO_3^-$ (wherein the Y represents at least one selected from the group consisting of a hydrogen atom, an alkyl group, Cl, Br, and I), or is represented by the following general formula (3):

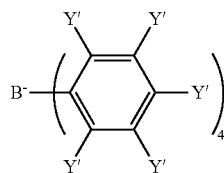

(3)

wherein each Y' represents a hydrogen atom, a halogen atom, or an alkyl group, and at least one of the Y' is a halogen atom.

2. The composition according to claim 1, wherein a ratio of the compound B to a total mass of the compound A and the compound B is 0.005 or more and 0.995 or less.

3. The composition according to claim 1, further comprising 5 ppm or higher and 10000 ppm or lower of a solvent having a boiling point of 0° C. to 200° C.

4. The composition according to claim 1, further comprising 5 ppm to 5000 ppm of a silver compound.

5. The composition according to claim 1, further comprising 5 ppm to 5000 ppm of a compound D represented by the following general formula (4):

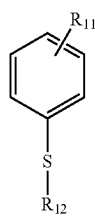

(4)

wherein $R_{11}$ and $R_{12}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an aralkyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other.

6. The composition according to claim 1, further comprising 5 ppm to 5000 ppm of a compound C represented by the following general formula (5):

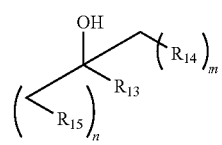

(5)

wherein $R_{13}$, $R_{14}$, and $R_{15}$ each represent a group selected from the group consisting of hydrogen, an alkyl group, a hydroxy group, a carboxyl group, an alkoxy group, an aryloxy group, an alkylcarbonyl group, an arylcarbonyl group, an aralkylcarbonyl group, an alkoxycarbonyl group, an aryloxycarbonyl group, an aralkyl group, an aralkyloxycarbonyl group, an alkylcarbonyloxy group, an arylcarbonyloxy group, an aralkylcarbonyloxy group, an alkoxycarbonyloxy group, an aryloxycarbonyloxy group, an aralkyloxycarbonyloxy group, an arylthiocarbonyl group, an arylthio group, an alkylthio group, an aryl group, a heterocyclic hydrocarbon group, an alkylsulfinyl group, an arylsulfinyl group, an alkylsulfonyl group, an arylsulfonyl group, a hydroxy(poly)alkyleneoxy group, an optionally substituted amino group, a cyano group, and a nitro group, and are the same or different from each other; n represents an integer of 0 to 3; m represents an integer of 1 to 4; and n and m satisfy n+m≤4.

7. A cation-generating agent comprising the composition according to claim 1.

* * * * *